United States Patent
Melchor

(10) Patent No.: US 11,850,160 B2
(45) Date of Patent: Dec. 26, 2023

(54) EXPANDABLE LORDOTIC INTERVERTEBRAL FUSION CAGE

(71) Applicant: Medos International Sarl, Le Locle (CH)

(72) Inventor: Jonathan Melchor, Providence, RI (US)

(73) Assignee: Medos International Sarl

( * ) Notice: Subject to any disclaimer, the term of this patent is extended or adjusted under 35 U.S.C. 154(b) by 87 days.

(21) Appl. No.: 17/213,867

(22) Filed: Mar. 26, 2021

(65) Prior Publication Data

US 2022/0304823 A1 Sep. 29, 2022

(51) Int. Cl.
*A61F 2/44* (2006.01)

(52) U.S. Cl.
CPC .......... *A61F 2/4425* (2013.01); *A61F 2/4455* (2013.01); *A61F 2002/443* (2013.01)

(58) Field of Classification Search
CPC ........ A61F 2250/0004–001; A61F 2250/0048; A61F 2/4455–2/447
See application file for complete search history.

(56) References Cited

U.S. PATENT DOCUMENTS

| | | | |
|---|---|---|---|
| 1,802,560 A | 4/1931 | Kerwin | |
| 1,924,695 A | 8/1933 | Olson | |
| 1,965,653 A | 7/1934 | Kennedy | |
| 2,077,804 A | 4/1937 | Morrison | |
| 2,115,250 A | 4/1938 | Bruson | |
| 2,121,193 A | 6/1938 | Hanicke | |
| 2,170,111 A | 8/1939 | Bruson | |
| 2,173,655 A | 9/1939 | Neracher et al. | |
| 2,229,024 A | 1/1941 | Bruson | |
| 2,243,717 A | 5/1941 | Moreira | |
| 2,381,050 A | 8/1945 | Hardinge | |
| 2,388,056 A | 10/1945 | Hendriks | |
| 2,485,531 A | 10/1949 | William et al. | |
| 2,489,870 A | 11/1949 | Dzus | |
| 2,570,465 A | 10/1951 | Lundholm | |
| 2,677,369 A | 5/1954 | Knowles | |
| 2,706,701 A | 4/1955 | Hans et al. | |
| 2,710,277 A | 6/1955 | Shelanski et al. | |
| 2,826,532 A | 3/1958 | Hosmer | |
| 2,900,305 A | 8/1959 | Siggia | |

(Continued)

FOREIGN PATENT DOCUMENTS

| | | |
|---|---|---|
| AU | 2006279558 A1 | 2/2007 |
| AU | 2005314079 B2 | 7/2012 |

(Continued)

OTHER PUBLICATIONS

Medco Forum, "Percutaneous Lumbar Fixation Via PERPOS PLS System Interventional Spine", Sep. 2008, vol. 15, No. 37.

(Continued)

*Primary Examiner* — Julianna N Harvey
*Assistant Examiner* — Angel Roberto Mora-Velazquez
(74) *Attorney, Agent, or Firm* — BakerHostetler

(57) ABSTRACT

An intervertebral fusion cage includes first and second endplate members, first and second ramp members, and an actuator. The first and second ramp members and first and second endplate members have complementary ramp surfaces that engage to expand the height of the fusion cage and to impart a lordotic profile to the fusion cage.

20 Claims, 12 Drawing Sheets

(56) References Cited

U.S. PATENT DOCUMENTS

| | | |
|---|---|---|
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Johnson |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,175,555 A | 11/1979 | Herbert |
| 4,205,399 A | 6/1980 | Jamiolkowski et al. |
| 4,208,511 A | 6/1980 | Jamiolkowski et al. |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | McCarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,538,612 A | 9/1985 | Patrick, Jr. |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,646,741 A | 3/1987 | Smith |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,706,670 A | 11/1987 | Andersen et al. |
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,834,757 A | 5/1989 | Brantigan |
| 4,838,282 A | 6/1989 | Strasser et al. |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,889,119 A | 12/1989 | Jamiolkowski et al. |
| 4,892,550 A | 1/1990 | Huebsch |
| 4,896,662 A | 1/1990 | Noble |
| 4,898,186 A | 2/1990 | Ikada et al. |
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |
| 4,940,467 A | 7/1990 | Tronzo |
| 4,941,466 A | 7/1990 | Romano |
| 4,946,378 A | 8/1990 | Hirayama et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Baumgart |
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |

(56) References Cited

U.S. PATENT DOCUMENTS

| | | |
|---|---|---|
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muehling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |

(56) References Cited

U.S. PATENT DOCUMENTS

| | | |
|---|---|---|
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Braanemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,556 A | 2/1997 | Pisharodi |
| 5,601,561 A | 2/1997 | Terry et al. |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,609,636 A | 3/1997 | Kohrs et al. |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,788,703 A | 8/1998 | Mittelmeier et al. |
| 5,792,044 A | 8/1998 | Foley et al. |
| 5,797,909 A | 8/1998 | Michelson |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,859,150 A | 1/1999 | Jamiolkowski et al. |
| 5,860,973 A | 1/1999 | Michelson |
| 5,860,977 A | 1/1999 | Zucherman et al. |

(56) References Cited

U.S. PATENT DOCUMENTS

| | | |
|---|---|---|
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,221 A | 3/1999 | Gelbard |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Tienboon |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,635 A | 9/1999 | Foley et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,976,187 A | 11/1999 | Richelsoph |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Schonhoffer |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,049,026 A | 4/2000 | Muschler |
| 6,053,922 A | 4/2000 | Krause et al. |
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,038 A | 8/2000 | Michelson |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Spinosa |
| 6,162,234 A | 12/2000 | Freedland et al. |
| 6,162,236 A | 12/2000 | Osada |
| 6,162,252 A | 12/2000 | Kuras et al. |

(56) References Cited

U.S. PATENT DOCUMENTS

| | | | |
|---|---|---|---|
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,342,074 B1 | 1/2002 | Simpson |
| 6,346,092 B1 | 2/2002 | Boris |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Ambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |

(56) References Cited

U.S. PATENT DOCUMENTS

| | | |
|---|---|---|
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Ambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Kraus |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |

(56) References Cited

U.S. PATENT DOCUMENTS

| | | |
|---|---|---|
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Mark |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,824,565 B2 | 11/2004 | Muhanna et al. |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Ambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,060,073 B2 | 6/2006 | Frey et al. |
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |

(56) References Cited

U.S. PATENT DOCUMENTS

| | | |
|---|---|---|
| 7,087,053 B2 | 8/2006 | Vanney |
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,125,424 B2 | 10/2006 | Banick et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,175,625 B2 | 2/2007 | Culbert |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,482 B2 | 6/2007 | Messerli et al. |
| 7,226,483 B2 | 6/2007 | Gerber et al. |
| 7,235,101 B2 | 6/2007 | Berry et al. |
| 7,238,204 B2 | 7/2007 | Le et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,406,775 B2 | 8/2008 | Funk et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,491,237 B2 | 2/2009 | Randall et al. |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,601,173 B2 | 10/2009 | Messerli et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,226 B2 | 2/2010 | Schaller |
| 7,666,266 B2 | 2/2010 | Izawa et al. |
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,686,807 B2 | 3/2010 | Padget et al. |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,704,280 B2 | 4/2010 | Echmann et al. |
| 7,708,778 B2 | 5/2010 | Gordon et al. |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |

(56) References Cited

U.S. PATENT DOCUMENTS

| | | |
|---|---|---|
| 7,763,028 B2 | 7/2010 | Lim et al. |
| 7,763,038 B2 | 7/2010 | O'Brien |
| 7,763,055 B2 | 7/2010 | Foley |
| 7,766,930 B2 | 8/2010 | Dipoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | LeHuec et al. |
| 7,828,849 B2 | 11/2010 | Lim |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,927,373 B2 | 4/2011 | Parsons et al. |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,938,857 B2 | 5/2011 | Garcia-Bengochea et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,377 B2 | 8/2011 | Culbert et al. |
| 7,993,403 B2 | 8/2011 | Foley et al. |
| 7,998,176 B2 | 8/2011 | Culbert |
| 8,007,535 B2 | 8/2011 | Hudgins et al. |
| 8,012,207 B2 | 9/2011 | Kim |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,972 B2 | 2/2012 | Zucherman et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | Delurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,187,332 B2 | 5/2012 | McLuen |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,675 B2 | 7/2012 | Rhoda |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,282,641 B2 | 10/2012 | Lopez et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,313,528 B1 | 11/2012 | Wensel |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,343,222 B2 | 1/2013 | Cope |
| 8,353,961 B2 | 1/2013 | McClintock et al. |
| 8,361,154 B2 | 1/2013 | Reo |
| 8,366,777 B2 | 2/2013 | Matthis et al. |
| 8,377,098 B2 | 2/2013 | Landry et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller et al. |
| 8,454,698 B2 | 6/2013 | De et al. |
| 8,465,524 B2 | 6/2013 | Siegal |
| 8,470,043 B2 | 6/2013 | Schaller et al. |

(56) References Cited

U.S. PATENT DOCUMENTS

| | | |
|---|---|---|
| 8,480,715 B2 | 7/2013 | Gray |
| 8,480,742 B2 | 7/2013 | Pisharodi |
| 8,480,748 B2 | 7/2013 | Poulos |
| 8,486,109 B2 | 7/2013 | Siegal |
| 8,486,148 B2 | 7/2013 | Butler et al. |
| 8,491,591 B2 | 7/2013 | Sebastian |
| 8,491,653 B2 | 7/2013 | Zucherman et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,545,567 B1 | 10/2013 | Krueger |
| 8,551,092 B2 | 10/2013 | Morgan et al. |
| 8,551,094 B2 | 10/2013 | Von et al. |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,088 B1 | 1/2014 | Tohmeh et al. |
| 8,623,091 B2 | 1/2014 | Suedkamp et al. |
| 8,628,576 B2 | 1/2014 | Triplett et al. |
| 8,628,577 B1 | 1/2014 | Jimenez |
| 8,628,578 B2 | 1/2014 | Miller et al. |
| 8,632,595 B2 | 1/2014 | Weiman |
| 8,636,746 B2 | 1/2014 | Jimenez et al. |
| 8,641,764 B2 | 2/2014 | Gately |
| 8,663,329 B2 | 3/2014 | Ernst |
| 8,663,331 B2 | 3/2014 | McClellan et al. |
| 8,668,740 B2 | 3/2014 | Rhoda et al. |
| 8,672,977 B2 | 3/2014 | Siegal et al. |
| 8,679,161 B2 | 3/2014 | Malandain et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,702,757 B2 | 4/2014 | Thommen et al. |
| 8,702,798 B2 | 4/2014 | Matthis et al. |
| 8,709,086 B2 | 4/2014 | Glerum |
| 8,709,088 B2 | 4/2014 | Kleiner et al. |
| 8,715,284 B2 | 5/2014 | Culbert |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,740,954 B2 | 6/2014 | Ghobrial et al. |
| 8,753,398 B2 | 6/2014 | Gordon et al. |
| 8,758,349 B2 | 6/2014 | Germain et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,733 B2 | 9/2014 | O'Neil et al. |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,900,235 B2 | 12/2014 | Siegal |
| 8,900,307 B2 | 12/2014 | Hawkins et al. |
| 8,906,098 B2 | 12/2014 | Siegal |
| 8,920,506 B2 | 12/2014 | McGuckin, Jr. |
| 8,926,704 B2 | 1/2015 | Glerum et al. |
| 8,936,641 B2 | 1/2015 | Cain |
| 8,940,049 B1 | 1/2015 | Jimenez et al. |
| 8,940,050 B2 | 1/2015 | Aurence et al. |
| 8,940,052 B2 | 1/2015 | Lechmann et al. |
| 8,961,609 B2 | 2/2015 | Schaller |
| 8,968,408 B2 | 3/2015 | Schaller et al. |
| 8,979,860 B2 | 3/2015 | Voellmicke et al. |
| 8,979,929 B2 | 3/2015 | Schaller |
| 8,986,387 B1 | 3/2015 | To et al. |
| 8,986,388 B2 | 3/2015 | Siegal et al. |
| 8,986,389 B2 | 3/2015 | Lim et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,101,491 B2 | 8/2015 | Rodgers et al. |
| 9,101,492 B2 | 8/2015 | Mangione et al. |
| 9,107,766 B1 | 8/2015 | McLean et al. |
| 9,119,730 B2 | 9/2015 | Glerum et al. |
| 9,237,956 B1 | 1/2016 | Jensen |
| 9,254,138 B2 | 2/2016 | Siegal et al. |
| 9,259,326 B2 | 2/2016 | Schaller |
| 9,271,846 B2 | 3/2016 | Lim et al. |
| 9,277,928 B2 | 3/2016 | Morgenstern Lopez |
| 9,282,979 B2 | 3/2016 | O'Neil et al. |
| 9,283,092 B2 | 3/2016 | Siegal et al. |
| 9,295,562 B2 | 3/2016 | Lechmann et al. |
| 9,314,348 B2 | 4/2016 | Emstad |
| 9,320,610 B2 | 4/2016 | Alheidt et al. |
| 9,320,615 B2 | 4/2016 | Suedkamp et al. |
| 9,326,866 B2 | 5/2016 | Schaller et al. |
| 9,333,091 B2 | 5/2016 | Dimauro |
| 9,358,123 B2 | 6/2016 | Remington et al. |
| 9,387,087 B2 | 7/2016 | Tyber |
| 9,387,313 B2 | 7/2016 | Culbert et al. |
| 9,402,732 B2 | 8/2016 | Gabelberger |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,934 B2 | 8/2016 | Cain |
| 9,414,936 B2 | 8/2016 | Miller et al. |
| 9,433,510 B2 | 9/2016 | Lechmann et al. |
| 9,439,776 B2 | 9/2016 | Dimauro et al. |
| 9,439,777 B2 | 9/2016 | Dimauro |
| 9,445,825 B2 | 9/2016 | Belaney et al. |
| 9,445,918 B1 | 9/2016 | Lin et al. |
| 9,445,919 B2 | 9/2016 | Palmatier et al. |
| 9,463,099 B2 | 10/2016 | Levy et al. |
| 9,474,623 B2 | 10/2016 | Cain |
| 9,492,288 B2 | 11/2016 | Wagner et al. |
| 9,510,954 B2 | 12/2016 | Glerum et al. |
| 9,522,070 B2 | 12/2016 | Flower et al. |

(56) References Cited

U.S. PATENT DOCUMENTS

| | | |
|---|---|---|
| 9,526,625 B2 | 12/2016 | Cain |
| 9,532,884 B2 | 1/2017 | Siegal et al. |
| 9,545,314 B2 | 1/2017 | Cain |
| 9,566,165 B2 | 2/2017 | Lee et al. |
| 9,566,167 B2 | 2/2017 | Barrus et al. |
| 9,579,215 B2 | 2/2017 | Suedkamp et al. |
| 9,592,063 B2 | 3/2017 | O'Neil et al. |
| 9,592,129 B2 | 3/2017 | Slivka et al. |
| 9,597,195 B2 | 3/2017 | Cain |
| 9,597,197 B2 | 3/2017 | Lechmann et al. |
| 9,662,223 B2 | 5/2017 | Matthis et al. |
| 9,662,224 B2 | 5/2017 | Weiman et al. |
| 9,675,470 B2 | 6/2017 | Packer et al. |
| 9,717,601 B2 | 8/2017 | Miller |
| 9,724,207 B2 | 8/2017 | Dimauro et al. |
| 9,730,803 B2 | 8/2017 | Dimauro et al. |
| 9,730,806 B2 | 8/2017 | Capote |
| 9,750,552 B2 | 9/2017 | Stephan et al. |
| 9,750,618 B1 | 9/2017 | Daffinson et al. |
| 9,763,678 B2 | 9/2017 | O'Neil et al. |
| 9,788,962 B2 | 10/2017 | Gabelberger |
| 9,788,963 B2 | 10/2017 | Aquino et al. |
| 9,788,971 B1 | 10/2017 | Stein |
| 9,801,639 B2 | 10/2017 | O'Neil et al. |
| 9,801,640 B2 | 10/2017 | O'Neil et al. |
| 9,801,729 B2 | 10/2017 | Dimauro et al. |
| 9,801,734 B1 | 10/2017 | Gustine et al. |
| 9,808,351 B2 | 11/2017 | Kelly et al. |
| 9,808,353 B2 | 11/2017 | Suddaby et al. |
| 9,814,589 B2 | 11/2017 | Dimauro |
| 9,814,590 B2 | 11/2017 | Serhan et al. |
| 9,833,334 B2 | 12/2017 | Voellmicke et al. |
| 9,839,528 B2 | 12/2017 | Weiman et al. |
| 9,839,530 B2 | 12/2017 | Hawkins et al. |
| 9,848,991 B2 | 12/2017 | Boehm et al. |
| 9,872,779 B2 | 1/2018 | Miller et al. |
| 9,895,236 B2 | 2/2018 | Voellmicke et al. |
| 9,907,560 B2 | 3/2018 | O'Neil et al. |
| 9,907,670 B2 | 3/2018 | Deridder et al. |
| 9,913,727 B2 | 3/2018 | Thommen et al. |
| 9,924,978 B2 | 3/2018 | Thommen et al. |
| 9,925,060 B2 | 3/2018 | Dimauro et al. |
| 9,931,223 B2 | 4/2018 | Cain |
| 9,931,226 B2 | 4/2018 | Kurtaliaj et al. |
| 9,937,053 B2 | 4/2018 | Melkent et al. |
| 9,949,769 B2 | 4/2018 | Serhan et al. |
| 9,962,272 B1 | 5/2018 | Daffinson et al. |
| 9,974,664 B2 | 5/2018 | Emerick et al. |
| 9,980,823 B2 | 5/2018 | Matthis et al. |
| 9,987,143 B2 | 6/2018 | Robinson et al. |
| 9,993,350 B2 | 6/2018 | Cain |
| 10,004,607 B2 | 6/2018 | Weiman et al. |
| 10,034,772 B2 | 7/2018 | Glerum et al. |
| 10,058,433 B2 | 8/2018 | Lechmann et al. |
| 10,085,843 B2 | 10/2018 | Dimauro |
| 10,092,417 B2 | 10/2018 | Weiman et al. |
| 10,098,759 B2 | 10/2018 | Weiman |
| 10,137,009 B2 | 11/2018 | Weiman et al. |
| 10,143,569 B2 | 12/2018 | Weiman et al. |
| 10,166,117 B1 | 1/2019 | Daffinson et al. |
| 10,182,831 B2 | 1/2019 | Marnay et al. |
| 10,219,915 B1 | 3/2019 | Stein |
| 10,238,500 B2 | 3/2019 | Rogers et al. |
| 10,265,191 B2 | 4/2019 | Lim et al. |
| 10,299,934 B2 | 5/2019 | Seifert et al. |
| 10,307,254 B2 | 6/2019 | Levy et al. |
| 10,363,142 B2 | 7/2019 | McClintock et al. |
| 10,376,372 B2 | 8/2019 | Serhan et al. |
| 10,390,963 B2 | 8/2019 | Olmos et al. |
| 10,398,563 B2 | 9/2019 | Engstrom |
| 10,398,566 B2 | 9/2019 | Olmos et al. |
| 10,405,986 B2 | 9/2019 | Kelly et al. |
| 10,405,989 B2 | 9/2019 | O'Neil et al. |
| 10,420,651 B2 | 9/2019 | Serhan et al. |
| 10,426,632 B2 | 10/2019 | Butler et al. |
| 10,433,971 B2 | 10/2019 | Dimauro et al. |
| 10,433,974 B2 | 10/2019 | Michael |
| 10,433,977 B2 | 10/2019 | Lechmann et al. |
| 10,449,056 B2 | 10/2019 | Cain |
| 10,449,057 B2 | 10/2019 | O'Neil et al. |
| 10,449,058 B2 | 10/2019 | Lechmann et al. |
| 10,470,894 B2 | 11/2019 | Foley et al. |
| 10,492,918 B2 | 12/2019 | Dimauro |
| 10,492,924 B2 | 12/2019 | Stein et al. |
| 10,500,062 B2 | 12/2019 | Marchek et al. |
| 10,512,489 B2 | 12/2019 | Serhan et al. |
| 10,537,436 B2 | 1/2020 | Maguire et al. |
| 10,548,741 B2 | 2/2020 | Suedkamp et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |
| 10,583,015 B2 | 3/2020 | Olmos et al. |
| 10,588,754 B2 | 3/2020 | O'Neil et al. |
| 10,624,758 B2 | 4/2020 | Slivka et al. |
| 10,639,164 B2 | 5/2020 | Dimauro et al. |
| 10,639,166 B2 | 5/2020 | Glerum et al. |
| 10,682,241 B2 | 6/2020 | Glerum et al. |
| 10,743,914 B2 | 8/2020 | Lopez et al. |
| 10,758,371 B2 | 9/2020 | Hessler et al. |
| 10,786,361 B2 | 9/2020 | Dimauro et al. |
| 10,799,366 B2 | 10/2020 | Davis et al. |
| 10,842,644 B2 | 11/2020 | Weiman et al. |
| 10,888,433 B2 | 1/2021 | Frasier et al. |
| 10,966,840 B2 | 4/2021 | Voellmicke et al. |
| 10,973,652 B2 | 4/2021 | Hawkins et al. |
| 11,051,954 B2 | 7/2021 | Greenhalgh et al. |
| 11,103,362 B2 | 8/2021 | Butler et al. |
| 11,285,018 B2 | 3/2022 | Shoshtaev |
| 11,426,286 B2 | 8/2022 | Spetzger |
| 2001/0011174 A1 | 8/2001 | Reiley et al. |
| 2001/0016741 A1 | 8/2001 | Burkus et al. |
| 2001/0016775 A1 | 8/2001 | Scarborough et al. |
| 2001/0037126 A1 | 11/2001 | Stack et al. |
| 2001/0039453 A1 | 11/2001 | Gresser et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045942 A1 | 4/2002 | Ham |
| 2002/0055740 A1 | 5/2002 | Lieberman |
| 2002/0055781 A1 | 5/2002 | Sazy |
| 2002/0068974 A1 | 6/2002 | Kuslich et al. |
| 2002/0072801 A1 | 6/2002 | Michelson |
| 2002/0077701 A1 | 6/2002 | Kuslich |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0138078 A1 | 9/2002 | Chappuis |
| 2002/0143331 A1 | 10/2002 | Zucherman et al. |
| 2002/0151976 A1 | 10/2002 | Foley et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173841 A1 | 11/2002 | Ortiz et al. |
| 2002/0173851 A1 | 11/2002 | McKay |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0006942 A1 | 1/2003 | Searls et al. |
| 2003/0014113 A1 | 1/2003 | Ralph et al. |
| 2003/0014116 A1 | 1/2003 | Ralph et al. |
| 2003/0023305 A1 | 1/2003 | McKay |
| 2003/0028250 A1 | 2/2003 | Reiley et al. |

(56) References Cited

U.S. PATENT DOCUMENTS

| | | |
|---|---|---|
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0050644 A1 | 3/2003 | Boucher et al. |
| 2003/0063582 A1 | 4/2003 | Mizell et al. |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074075 A1 | 4/2003 | Thomas et al. |
| 2003/0078667 A1 | 4/2003 | Manasas et al. |
| 2003/0108588 A1 | 6/2003 | Chen et al. |
| 2003/0130664 A1 | 7/2003 | Boucher et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0171812 A1 | 9/2003 | Grunberg et al. |
| 2003/0187431 A1 | 10/2003 | Simonson |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0208122 A1 | 11/2003 | Melkent et al. |
| 2003/0208203 A1 | 11/2003 | Lim et al. |
| 2003/0208220 A1 | 11/2003 | Worley et al. |
| 2003/0208270 A9 | 11/2003 | Michelson |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034429 A1 | 2/2004 | Lambrecht et al. |
| 2004/0049190 A1 | 3/2004 | Biedermann et al. |
| 2004/0049223 A1 | 3/2004 | Nishtala et al. |
| 2004/0049270 A1 | 3/2004 | Gewirtz |
| 2004/0059333 A1 | 3/2004 | Carl et al. |
| 2004/0059337 A1 | 3/2004 | Hanson et al. |
| 2004/0059350 A1 | 3/2004 | Gordon et al. |
| 2004/0059418 A1 | 3/2004 | McKay et al. |
| 2004/0068269 A1 | 4/2004 | Bonati et al. |
| 2004/0073213 A1 | 4/2004 | Serhan et al. |
| 2004/0082953 A1 | 4/2004 | Petit |
| 2004/0083000 A1 | 4/2004 | Keller et al. |
| 2004/0087947 A1 | 5/2004 | Lim et al. |
| 2004/0088055 A1 | 5/2004 | Hanson et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106940 A1 | 6/2004 | Shaolian et al. |
| 2004/0116997 A1 | 6/2004 | Taylor et al. |
| 2004/0117022 A1 | 6/2004 | Marnay et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193271 A1 | 9/2004 | Raser et al. |
| 2004/0193277 A1 | 9/2004 | Long et al. |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | Dimauro et al. |
| 2004/0243229 A1 | 12/2004 | Mdlund et al. |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260300 A1 | 12/2004 | Gorensek et al. |
| 2004/0260397 A1 | 12/2004 | Ambrecht et al. |
| 2004/0267271 A9 | 12/2004 | Scribner et al. |
| 2004/0267367 A1 | 12/2004 | O'Neil |
| 2005/0004578 A1 | 1/2005 | Ambrecht et al. |
| 2005/0010292 A1 | 1/2005 | Carrasco |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0027360 A1 | 2/2005 | Webb et al. |
| 2005/0033295 A1 | 2/2005 | Wisnewski |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |

(56) References Cited

U.S. PATENT DOCUMENTS

| | | |
|---|---|---|
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Michael John |
| 2005/0090833 A1 | 4/2005 | DiPoto |
| 2005/0090852 A1 | 4/2005 | Ayne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0149022 A1 | 7/2005 | Shaolian et al. |
| 2005/0149030 A1 | 7/2005 | Serhan et al. |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0159819 A1 | 7/2005 | McCormack et al. |
| 2005/0165398 A1 | 7/2005 | Reiley |
| 2005/0165420 A1 | 7/2005 | Cha |
| 2005/0165484 A1 | 7/2005 | Ferree |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde |
| 2005/0278029 A1 | 12/2005 | Trieu |
| 2005/0283238 A1 | 12/2005 | Reiley |
| 2005/0287071 A1 | 12/2005 | Wenz |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0032621 A1 | 2/2006 | Martin et al. |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Andry et al. |
| 2006/0058880 A1 | 3/2006 | Wysocki et al. |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0085002 A1 | 4/2006 | Trieu et al. |
| 2006/0085009 A1 | 4/2006 | Truckai et al. |

(56) References Cited

U.S. PATENT DOCUMENTS

| | | |
|---|---|---|
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |
| 2006/0119629 A1 | 6/2006 | An et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | Dinello et al. |
| 2006/0136064 A1 | 6/2006 | Sherman |
| 2006/0142759 A1 | 6/2006 | Amin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149229 A1 | 7/2006 | Kwak et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247771 A1 | 11/2006 | Peterman et al. |
| 2006/0247781 A1 | 11/2006 | Francis |
| 2006/0253120 A1 | 11/2006 | Anderson et al. |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118222 A1 | 5/2007 | Lang |
| 2007/0118223 A1 | 5/2007 | Allard et al. |

(56) References Cited

U.S. PATENT DOCUMENTS

| | | |
|---|---|---|
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |
| 2007/0162132 A1 | 7/2007 | Messerli |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Trieu |
| 2007/0233083 A1 | 10/2007 | Abdou |
| 2007/0233089 A1 | 10/2007 | Dipoto et al. |
| 2007/0233130 A1 | 10/2007 | Suddaby |
| 2007/0233244 A1 | 10/2007 | Lopez et al. |
| 2007/0233254 A1 | 10/2007 | Grotz et al. |
| 2007/0250167 A1 | 10/2007 | Bray et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Trieu et al. |
| 2007/0270954 A1 | 11/2007 | Wu |
| 2007/0270957 A1 | 11/2007 | Heinz |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | De et al. |
| 2007/0288091 A1 | 12/2007 | Braddock et al. |
| 2008/0009877 A1 | 1/2008 | Sankaran et al. |
| 2008/0015694 A1 | 1/2008 | Tribus |
| 2008/0021556 A1 | 1/2008 | Edie |
| 2008/0021557 A1 | 1/2008 | Trieu |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |
| 2008/0027454 A1 | 1/2008 | Johnson et al. |
| 2008/0027544 A1 | 1/2008 | Melkent |
| 2008/0027550 A1 | 1/2008 | Link et al. |
| 2008/0045966 A1 | 2/2008 | Buttermann et al. |
| 2008/0051890 A1 | 2/2008 | Waugh et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0097454 A1 | 4/2008 | Deridder et al. |
| 2008/0097611 A1 | 4/2008 | Mastrorio et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0132934 A1 | 6/2008 | Reiley et al. |
| 2008/0133012 A1 | 6/2008 | McGuckin |
| 2008/0133017 A1 | 6/2008 | Beyar et al. |
| 2008/0140085 A1 | 6/2008 | Gately et al. |
| 2008/0147129 A1 | 6/2008 | Biedermann et al. |
| 2008/0154377 A1 | 6/2008 | Voellmicke |
| 2008/0154379 A1 | 6/2008 | Steiner et al. |
| 2008/0161927 A1 | 7/2008 | Savage et al. |
| 2008/0167657 A1 | 7/2008 | Greenhalgh |
| 2008/0172128 A1 | 7/2008 | Perez-Cruet et al. |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195210 A1 | 8/2008 | Milijasevic et al. |
| 2008/0208344 A1 | 8/2008 | Kilpela et al. |
| 2008/0221586 A1 | 9/2008 | Garcia-Bengochea et al. |
| 2008/0221687 A1 | 9/2008 | Viker |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0312743 A1 | 12/2008 | Vila et al. |
| 2008/0319477 A1 | 12/2008 | Justis et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | Von et al. |
| 2009/0069895 A1 | 3/2009 | Gittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Lowry et al. |
| 2009/0105712 A1 | 4/2009 | Dauster et al. |
| 2009/0105745 A1 | 4/2009 | Culbert |

(56) References Cited

U.S. PATENT DOCUMENTS

| | | |
|---|---|---|
| 2009/0112217 A1 | 4/2009 | Hester |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0198339 A1 | 8/2009 | Kleiner et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0234364 A1 | 9/2009 | Crook |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van et al. |
| 2010/0042218 A1 | 2/2010 | Nebosky et al. |
| 2010/0049324 A1 | 2/2010 | Valdevit et al. |
| 2010/0057204 A1 | 3/2010 | Kadaba et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga et al. |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0114105 A1 | 5/2010 | Butters et al. |
| 2010/0114147 A1 | 5/2010 | Biyani |
| 2010/0125334 A1 | 5/2010 | Krueger |
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0241231 A1 | 9/2010 | Marino et al. |
| 2010/0249935 A1 | 9/2010 | Slivka et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0274358 A1 | 10/2010 | Mueller et al. |
| 2010/0280619 A1 | 11/2010 | Yuan et al. |
| 2010/0286777 A1 | 11/2010 | Rrico et al. |
| 2010/0292700 A1 | 11/2010 | Ries |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0324683 A1 | 12/2010 | Reichen et al. |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | McManus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0040332 A1 | 2/2011 | Culbert et al. |
| 2011/0046674 A1 | 2/2011 | Calvosa et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160866 A1 | 6/2011 | Laurence et al. |
| 2011/0172716 A1 | 7/2011 | Glerum |
| 2011/0190816 A1 | 8/2011 | Sheffer et al. |
| 2011/0190891 A1 | 8/2011 | Suh et al. |
| 2011/0230971 A1 | 9/2011 | Donner et al. |
| 2011/0238072 A1 | 9/2011 | Tyndall |
| 2011/0251690 A1 | 10/2011 | Berger et al. |
| 2011/0270261 A1 | 11/2011 | Mast et al. |
| 2011/0276142 A1 | 11/2011 | Niemiec et al. |
| 2011/0282459 A1 | 11/2011 | McClellan et al. |
| 2011/0307010 A1 | 12/2011 | Pradhan |
| 2011/0313465 A1 | 12/2011 | Warren et al. |
| 2011/0319899 A1 | 12/2011 | O'Neil et al. |
| 2011/0319998 A1 | 12/2011 | O'Neil et al. |
| 2011/0320000 A1 | 12/2011 | O'Neil et al. |
| 2012/0004726 A1 | 1/2012 | Greenhalgh et al. |
| 2012/0004732 A1 | 1/2012 | Goel et al. |
| 2012/0006361 A1 | 1/2012 | Miyagi et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029639 A1 | 2/2012 | Blackwell et al. |
| 2012/0035730 A1 | 2/2012 | Spann |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0109319 A1 | 5/2012 | Perisic |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158148 A1 | 6/2012 | Glerum et al. |
| 2012/0191204 A1 | 7/2012 | Bae et al. |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0253395 A1 | 10/2012 | Linares |
| 2012/0253406 A1 | 10/2012 | Bae et al. |
| 2012/0277869 A1 | 11/2012 | Siccardi et al. |
| 2012/0277877 A1 | 11/2012 | Smith et al. |
| 2012/0283837 A1 | 11/2012 | Bae et al. |

(56) References Cited

U.S. PATENT DOCUMENTS

| | | |
|---|---|---|
| 2012/0310350 A1 | 12/2012 | Farris et al. |
| 2012/0310352 A1 | 12/2012 | Dimauro et al. |
| 2012/0323327 A1 | 12/2012 | McAfee |
| 2012/0330421 A1 | 12/2012 | Weiman |
| 2013/0006362 A1 | 1/2013 | Biedermann et al. |
| 2013/0023937 A1 | 1/2013 | Biedermann et al. |
| 2013/0053966 A1 | 2/2013 | Jimenez et al. |
| 2013/0060337 A1 | 3/2013 | Petersheim et al. |
| 2013/0073044 A1 | 3/2013 | Gamache |
| 2013/0079790 A1 | 3/2013 | Stein et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0150906 A1 | 6/2013 | Kerboul et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0197647 A1 | 8/2013 | Wolters et al. |
| 2013/0204371 A1 | 8/2013 | McLuen et al. |
| 2013/0218276 A1 | 8/2013 | Fiechter et al. |
| 2013/0231747 A1 | 9/2013 | Olmos et al. |
| 2013/0238006 A1 | 9/2013 | O'Neil et al. |
| 2013/0253585 A1 | 9/2013 | Garcia et al. |
| 2013/0261746 A1 | 10/2013 | Linares et al. |
| 2013/0261747 A1 | 10/2013 | Geisert |
| 2013/0268077 A1 | 10/2013 | You et al. |
| 2013/0274883 A1 | 10/2013 | MCluen et al. |
| 2013/0310937 A1* | 11/2013 | Pimenta ............... A61F 2/4425 623/17.15 |
| 2013/0310939 A1 | 11/2013 | Fabian et al. |
| 2013/0325128 A1 | 12/2013 | Perloff et al. |
| 2014/0018816 A1 | 1/2014 | Fenn et al. |
| 2014/0039622 A1 | 2/2014 | Glerum et al. |
| 2014/0039626 A1 | 2/2014 | Dale |
| 2014/0046333 A1 | 2/2014 | Johnson et al. |
| 2014/0046446 A1 | 2/2014 | Robinson |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0067073 A1 | 3/2014 | Hauck |
| 2014/0081267 A1 | 3/2014 | Orsak et al. |
| 2014/0086962 A1 | 3/2014 | Jin et al. |
| 2014/0094916 A1 | 4/2014 | Glerum et al. |
| 2014/0094917 A1 | 4/2014 | Salerni |
| 2014/0100662 A1 | 4/2014 | Patterson et al. |
| 2014/0107790 A1 | 4/2014 | Combrowski |
| 2014/0114414 A1 | 4/2014 | Abdou et al. |
| 2014/0121774 A1 | 5/2014 | Glerum et al. |
| 2014/0128977 A1 | 5/2014 | Glerum et al. |
| 2014/0128980 A1 | 5/2014 | Kirschman |
| 2014/0135930 A1 | 5/2014 | Georges |
| 2014/0135934 A1 | 5/2014 | Hansell et al. |
| 2014/0142706 A1 | 5/2014 | Hansell et al. |
| 2014/0148904 A1 | 5/2014 | Robinson |
| 2014/0163682 A1 | 6/2014 | Lott et al. |
| 2014/0163683 A1 | 6/2014 | Seifert et al. |
| 2014/0172103 A1 | 6/2014 | O'Neil et al. |
| 2014/0172105 A1 | 6/2014 | Frasier et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0243892 A1 | 8/2014 | Choinski |
| 2014/0243981 A1 | 8/2014 | Davenport et al. |
| 2014/0249629 A1 | 9/2014 | Moskowitz et al. |
| 2014/0249630 A1 | 9/2014 | Weiman |
| 2014/0249632 A1 | 9/2014 | Weiman |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277473 A1 | 9/2014 | Perrow |
| 2014/0277474 A1 | 9/2014 | Robinson et al. |
| 2014/0277476 A1 | 9/2014 | McLean et al. |
| 2014/0277481 A1 | 9/2014 | Lee et al. |
| 2014/0277507 A1 | 9/2014 | Baynham |
| 2014/0296983 A1 | 10/2014 | Fauth et al. |
| 2014/0303731 A1 | 10/2014 | Glerum |
| 2014/0303732 A1 | 10/2014 | Rhoda et al. |
| 2014/0336764 A1 | 11/2014 | Masson et al. |
| 2014/0343678 A1 | 11/2014 | Suddaby et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0051701 A1 | 2/2015 | Glerum et al. |
| 2015/0057755 A1 | 2/2015 | Suddaby et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094813 A1 | 4/2015 | Lechmann et al. |
| 2015/0094814 A1 | 4/2015 | Emerick et al. |
| 2015/0100128 A1 | 4/2015 | Glerum et al. |
| 2015/0112398 A1 | 4/2015 | Morgenstern et al. |
| 2015/0112437 A1 | 4/2015 | Davis et al. |
| 2015/0112438 A1 | 4/2015 | McLean |
| 2015/0173916 A1 | 6/2015 | Cain |
| 2015/0182347 A1 | 7/2015 | Robinson |
| 2015/0190242 A1 | 7/2015 | Blain et al. |
| 2015/0196400 A1 | 7/2015 | Dace |
| 2015/0216671 A1 | 8/2015 | Cain |
| 2015/0216672 A1 | 8/2015 | Cain |
| 2015/0230929 A1 | 8/2015 | Lorio |
| 2015/0230932 A1 | 8/2015 | Schaller |
| 2015/0238324 A1 | 8/2015 | Nebosky et al. |
| 2015/0250606 A1 | 9/2015 | McLean |
| 2015/0272743 A1 | 10/2015 | Jimenez et al. |
| 2015/0305881 A1 | 10/2015 | Bal et al. |
| 2015/0320571 A1 | 11/2015 | Lechmann et al. |
| 2016/0016309 A1 | 1/2016 | Swift et al. |
| 2016/0022438 A1 | 1/2016 | Lamborne et al. |
| 2016/0038301 A1 | 2/2016 | Wickham |
| 2016/0045333 A1 | 2/2016 | Baynham |
| 2016/0051373 A1 | 2/2016 | Faulhaber |
| 2016/0051374 A1 | 2/2016 | Faulhaber |
| 2016/0067055 A1 | 3/2016 | Hawkins et al. |
| 2016/0081814 A1 | 3/2016 | Baynham |
| 2016/0089247 A1 | 3/2016 | Nichols et al. |
| 2016/0100951 A1 | 4/2016 | Suddaby et al. |
| 2016/0100954 A1 | 4/2016 | Rumi et al. |
| 2016/0106551 A1 | 4/2016 | Grimberg et al. |
| 2016/0120662 A1 | 5/2016 | Schaller |
| 2016/0128843 A1 | 5/2016 | Tsau et al. |
| 2016/0166396 A1 | 6/2016 | McClintock |
| 2016/0199195 A1 | 7/2016 | Hauck et al. |
| 2016/0199196 A1 | 7/2016 | Serhan et al. |
| 2016/0228258 A1 | 8/2016 | Schaller et al. |
| 2016/0235455 A1 | 8/2016 | Wahl |
| 2016/0256291 A1 | 9/2016 | Miller |
| 2016/0317714 A1 | 11/2016 | Dimauro et al. |
| 2016/0367265 A1 | 12/2016 | Morgenstern Lopez |
| 2017/0000622 A1 | 1/2017 | Thommen et al. |
| 2017/0056179 A1 | 3/2017 | Lorio |
| 2017/0095341 A1 | 4/2017 | Smith |
| 2017/0100177 A1 | 4/2017 | Kim |
| 2017/0100255 A1 | 4/2017 | Hleihil et al. |
| 2017/0100260 A1 | 4/2017 | Duffield et al. |
| 2017/0119542 A1 | 5/2017 | Logan et al. |
| 2017/0128226 A1 | 5/2017 | Faulhaber |
| 2017/0209284 A1 | 7/2017 | Overes et al. |
| 2017/0216045 A1 | 8/2017 | Dewey et al. |
| 2017/0216046 A1 | 8/2017 | Greenhalgh et al. |
| 2017/0266015 A1 | 9/2017 | Overes et al. |
| 2017/0290674 A1 | 10/2017 | Olmos et al. |

(56) References Cited

U.S. PATENT DOCUMENTS

| | | | |
|---|---|---|---|
| 2017/0290675 A1 | 10/2017 | Olmos et al. | |
| 2017/0290677 A1 | 10/2017 | Olmos et al. | |
| 2017/0296352 A1 | 10/2017 | Richerme et al. | |
| 2017/0367843 A1 | 12/2017 | Eisen et al. | |
| 2017/0367844 A1 | 12/2017 | Eisen et al. | |
| 2017/0367845 A1 | 12/2017 | Eisen et al. | |
| 2018/0028200 A1 | 2/2018 | O'Neil et al. | |
| 2018/0036141 A1 | 2/2018 | Oneil et al. | |
| 2018/0071111 A1 | 3/2018 | Sharifi-Mehr et al. | |
| 2018/0116811 A1 | 5/2018 | Bernard et al. | |
| 2018/0161175 A1 | 6/2018 | Frasier et al. | |
| 2018/0193164 A1 | 7/2018 | Shoshtaev | |
| 2018/0256360 A1 | 9/2018 | Cain | |
| 2018/0256362 A1 | 9/2018 | Slivka et al. | |
| 2018/0360616 A1 | 12/2018 | Luu | |
| 2019/0008654 A1 | 1/2019 | Thommen | |
| 2019/0021868 A1 | 1/2019 | Ludwig et al. | |
| 2019/0083276 A1 | 3/2019 | Dimauro | |
| 2019/0105171 A1 | 4/2019 | Rogers et al. | |
| 2019/0117409 A1* | 4/2019 | Shoshtaev | A61F 2/447 |
| 2019/0133785 A1 | 5/2019 | Georges | |
| 2019/0142602 A1 | 5/2019 | Olmos et al. | |
| 2019/0254836 A1* | 8/2019 | Cowan | A61F 2/4455 |
| 2019/0269521 A1 | 9/2019 | Shoshtaev | |
| 2019/0336301 A1 | 11/2019 | Engstrom | |
| 2019/0388238 A1 | 12/2019 | Lechmann et al. | |
| 2020/0008950 A1 | 1/2020 | Serhan et al. | |
| 2020/0015982 A1 | 1/2020 | O'Neil | |
| 2020/0030114 A1 | 1/2020 | Cain | |
| 2020/0060843 A1 | 2/2020 | Evans et al. | |
| 2020/0078190 A1* | 3/2020 | Rogers | A61F 2/4455 |
| 2020/0078192 A1 | 3/2020 | Marchek et al. | |
| 2020/0129307 A1* | 4/2020 | Hunziker | A61F 2/447 |
| 2020/0129308 A1 | 4/2020 | Suedkamp et al. | |
| 2020/0297506 A1 | 9/2020 | Olmos et al. | |
| 2020/0375754 A1 | 12/2020 | Cain | |
| 2020/0375755 A1 | 12/2020 | Cain | |
| 2020/0383799 A1 | 12/2020 | Cain | |
| 2020/0405497 A1 | 12/2020 | Olmos et al. | |
| 2020/0405500 A1 | 12/2020 | Cain | |
| 2021/0000160 A1 | 1/2021 | Olmos et al. | |
| 2021/0077272 A1* | 3/2021 | Eisen | A61F 2/4455 |
| 2021/0101585 A1 | 4/2021 | Son et al. | |
| 2021/0177619 A1 | 6/2021 | Voellmicke et al. | |
| 2021/0186706 A1 | 6/2021 | Spitler et al. | |
| 2021/0353427 A1 | 11/2021 | Butler et al. | |
| 2022/0409395 A1 | 12/2022 | Hunziker et al. | |

FOREIGN PATENT DOCUMENTS

| | | |
|---|---|---|
| CA | 2617872 A1 | 2/2007 |
| CN | 1177918 A | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 102164552 A | 8/2011 |
| CN | 103620249 A | 3/2014 |
| CN | 104023674 A | 9/2014 |
| CN | 104023675 A | 9/2014 |
| CN | 104042366 A | 9/2014 |
| CN | 104822332 A | 8/2015 |
| CN | 104921848 A | 9/2015 |
| CN | 104939876 A | 9/2015 |
| CN | 105025846 A | 11/2015 |
| CN | 105188582 A | 12/2015 |
| CN | 204971722 U | 1/2016 |
| CN | 105769391 A | 7/2016 |
| CN | 105769392 A | 7/2016 |
| CN | 107205829 A | 9/2017 |
| CN | 107510524 A | 12/2017 |
| DE | 2804936 A1 | 8/1979 |
| DE | 3023353 A1 | 4/1981 |
| DE | 3801459 A1 | 8/1989 |
| DE | 3911610 A1 | 10/1990 |
| DE | 4012622 C1 | 7/1991 |
| DE | 9407806 U1 | 7/1994 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| DE | 10357960 B4 | 9/2015 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0509084 A1 | 10/1992 |
| EP | 0525352 A1 | 2/1993 |
| EP | 0529275 A2 | 3/1993 |
| EP | 0609084 A2 | 8/1994 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1157676 A1 | 11/2001 |
| EP | 1283026 A2 | 2/2003 |
| EP | 1290985 A2 | 3/2003 |
| EP | 1308132 A2 | 5/2003 |
| EP | 1374784 A1 | 1/2004 |
| EP | 1378205 A1 | 1/2004 |
| EP | 1405602 A1 | 4/2004 |
| EP | 1532949 A1 | 5/2005 |
| EP | 1541096 A1 | 6/2005 |
| EP | 1605836 A1 | 12/2005 |
| EP | 1385449 B1 | 7/2006 |
| EP | 1683593 A2 | 7/2006 |
| EP | 1698305 A1 | 9/2006 |
| EP | 1829486 A1 | 9/2007 |
| EP | 1843723 A1 | 10/2007 |
| EP | 1845874 A1 | 10/2007 |
| EP | 1924227 A2 | 5/2008 |
| EP | 1925272 | 5/2008 |
| EP | 2331023 A2 | 6/2011 |
| EP | 2368529 A1 | 9/2011 |
| EP | 2237748 B1 | 9/2012 |
| EP | 2641571 A1 | 9/2013 |
| EP | 2699065 A1 | 2/2014 |
| EP | 2705809 A1 | 3/2014 |
| EP | 2764851 A1 | 8/2014 |
| EP | 2777633 | 9/2014 |
| EP | 2645965 B1 | 8/2016 |
| EP | 3263072 A1 | 1/2018 |
| EP | 3366263 A1 | 8/2018 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| FR | 2948277 | 1/2011 |
| FR | 3026294 | 4/2016 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 07-213533 A | 8/1995 |
| JP | 10-085232 A | 4/1998 |

(56) References Cited

FOREIGN PATENT DOCUMENTS

| | | |
|---|---|---|
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-501901 A | 1/2006 |
| JP | 2006-516456 | 7/2006 |
| JP | 2007-054666 A | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508048 A | 4/2012 |
| JP | 4988203 B2 | 8/2012 |
| JP | 2013-508031 | 3/2013 |
| JP | 5164571 B2 | 3/2013 |
| JP | 2014-502867 A | 2/2014 |
| JP | 2015-500707 A | 1/2015 |
| JP | 2015-525652 A | 9/2015 |
| JP | 2017-505196 A | 2/2017 |
| KR | 20-0290058 Y1 | 9/2002 |
| WO | 91/09572 A1 | 7/1991 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | 99/42062 A1 | 8/1999 |
| WO | 99/52478 A1 | 10/1999 |
| WO | 99/53871 A1 | 10/1999 |
| WO | 99/60956 A1 | 12/1999 |
| WO | 99/62417 A1 | 12/1999 |
| WO | 99/63914 A1 | 12/1999 |
| WO | 00/12033 | 3/2000 |
| WO | 00/13620 A1 | 3/2000 |
| WO | 00/24343 A1 | 5/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/80751 A1 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/45627 A1 | 6/2002 |
| WO | 02/47563 A1 | 6/2002 |
| WO | 02/71921 A2 | 9/2002 |
| WO | 02/85250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/03951 A1 | 6/2003 |
| WO | 2003/101308 A1 | 12/2003 |
| WO | 2004/008949 A1 | 1/2004 |
| WO | 03/59180 A2 | 3/2004 |
| WO | 2004/030582 A2 | 4/2004 |
| WO | 2004/034924 A2 | 4/2004 |
| WO | 2004/062505 A1 | 7/2004 |
| WO | 2004/064603 A2 | 8/2004 |
| WO | 2004/069033 A2 | 8/2004 |
| WO | 2004/078220 A2 | 9/2004 |
| WO | 2004/078221 A2 | 9/2004 |
| WO | 2004/080316 A1 | 9/2004 |
| WO | 2004/082526 A2 | 9/2004 |
| WO | 2004/098420 A2 | 11/2004 |
| WO | 2004/098453 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/094297 A2 | 10/2005 |
| WO | 2005/112834 A2 | 12/2005 |
| WO | 2005/112835 A2 | 12/2005 |
| WO | 2005/115261 A1 | 12/2005 |
| WO | 2006/017507 A2 | 2/2006 |
| WO | 2006/044920 A2 | 4/2006 |
| WO | 2006/047587 A2 | 5/2006 |
| WO | 2006/047645 A2 | 5/2006 |
| WO | 2006/058079 A2 | 6/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/078972 A2 | 7/2006 |
| WO | 2006/081843 A1 | 8/2006 |
| WO | 2006/108067 A2 | 10/2006 |
| WO | 2006/118944 A1 | 11/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/005627 A2 | 1/2008 |
| WO | 2008/011378 A1 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/011348 A1 | 1/2010 |
| WO | 2010/068725 A2 | 6/2010 |
| WO | 2010/075451 A1 | 7/2010 |
| WO | 2010/075555 A2 | 7/2010 |
| WO | 2010/088766 A1 | 8/2010 |
| WO | 2010/121002 A1 | 10/2010 |
| WO | 2010/136170 A1 | 12/2010 |
| WO | 2010/148112 A1 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | 2011/079910 A2 | 7/2011 |
| WO | 2011/119617 A1 | 9/2011 |

(56) References Cited

FOREIGN PATENT DOCUMENTS

| | | |
|---|---|---|
| WO | 2011/142761 A1 | 11/2011 |
| WO | 2011/150350 A1 | 12/2011 |
| WO | 2012/009152 A1 | 1/2012 |
| WO | 2012/027490 A2 | 3/2012 |
| WO | 2012/028182 A1 | 3/2012 |
| WO | 2012/030331 A1 | 3/2012 |
| WO | 2012/089317 A1 | 7/2012 |
| WO | 2012/103254 A2 | 8/2012 |
| WO | 2012/122294 A1 | 9/2012 |
| WO | 2012/129197 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/148176 A1 | 10/2013 |
| WO | 2013/149611 A1 | 10/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/004660 A1 | 1/2015 |
| WO | 2015/013479 A2 | 1/2015 |
| WO | 2015/022039 A1 | 2/2015 |
| WO | 2015/048997 A1 | 4/2015 |
| WO | 2016/069796 A1 | 5/2016 |
| WO | 2016/118246 A1 | 7/2016 |
| WO | 2016/127139 A1 | 8/2016 |
| WO | 2017/040881 A1 | 3/2017 |
| WO | 2017/066226 A1 | 4/2017 |
| WO | 2017/136620 A1 | 8/2017 |
| WO | 2018/078148 A1 | 5/2018 |

OTHER PUBLICATIONS

Medco Forum, "Percutaneous Lumbar Fixation via PERPOS System From Interventional Spine", Oct. 2007, vol. 14, No. 49.
Mendez et al., Self-curing acrylic formulations containing PMMA/PCL composites: properties and antibiotic release behavior. J Biomed Mater Res. Jul. 2002;61 (1 ):66-74.
Morgenstern R; Transforaminal Endoscopic Stenosis Surgery—A Comparative Study of Laser and Reamed Foraminoplasty.In: European Musculoskeletal Review, Issue 1, 2009.
Nguyen et al., Poly(Aryl-Ether-Ether-Ketone) and its Advanced Composites: A Review, Polymer Composites, Apr. 1987, vol. 8, No. 2, pp. 57-73.
Niosi, "Biomechanical characterization of the three-dimentional kinematic behaviour of the Dynesys dynamic stabilization system: an in vitro study", EUR SPINE J (2006) 15: pp. 913-922.
Osteoset Registered DBM Pellets (Important Medical Information) [online], Nov. 2002 [retrieved on Oct. 14, 2003]. Retrieved from the Internet <URL: http://www.wmt.com/Literature>.
Polikeit, "The Importance of the Endplate for Interbody Cages in the Lumbar Spine", Eur. Spine J., 2003, pp. 556-561, vol. 12.
ProMap TM EMG Navigation Probe. Technical Brochure Spineology Inc, Dated May 2009.
Regan et al., Endoscopic thoracic fusion cage. Atlas of Endoscopic Spine Surgery. Quality Medical Publishing, Inc. 1995; 350-354.
Shin, "Posterior Lumbar Interbody Fusion via a Unilateral Approach", Yonsei Medical Journal, 2006, pp. 319-325, vol. 47(3).
Siddiqui, "The Positional Magnetic Resonance Imaging Changes in the Lumbar Spine Following Insertion of a Novel Interspinous Process Distraction Device", Spine, vol. 30, No. 23, pp. 2677-2682, 2005.

Slivka et al., In vitro compression testing of fiber-reinforced, bioabsorbable, porous implants. Synthetic Bioabsorbable Polymers for Implants. STP1396, pp. 124-135, ATSM International, Jul. 2000.
Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.
Spine Solutions Brochure—Prodisc 2001, 16 pages.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4 ):571-7.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.
U.S. Appl. No. 60/424,055, filed Nov. 5, 2002, entitled Method and apparatus for spinal fixation.
U.S. Appl. No. 60/397,588, Method and apparatus for spinal fixation, filed Jul. 19, 2002.
U.S. Appl. No. 61/675,975, Expandable Implant, filed Jul. 26, 2012.
U.S. Appl. No. 60/942,998, Method and Apparatus for Spinal Stabilization, filed Jun. 8, 2007.
United States Disctrict Court, Central District of California, Case No. 1 :10-CV-00849-LPS, *Nuvasive, Inc.*, vs., *Globus Medical, Inc.*, Videotaped Deposition of: Luiz Pimenta, M.D., May 9, 2012, 20 pages.
U.S. Appl. No. 09/558,057, filed Apr. 26, 2000, entitled Bone Fixation System.
U.S. Appl. No. 14/640,220, filed Mar. 6, 2015, entitled Expandable Intervertebral Implant.
U.S. Appl. No. 14/685,358, filed Apr. 13, 2015, entitled Expandable Intervertebral Implant.
U.S. Appl. No. 14/685,402, filed Apr. 13, 2015, entitled Expandable Intervertebral Implant.
U.S. Appl. No. 62/950,180, filed Dec. 19, 2019, Spitler et al.
Vandorpe, "Biodegradable Polyphosphazenes For Biomedical Applications", The Handbook of Biodegradable Polymers, edited by Domb et al., Hardwood Academic Press, 1997, pp. 161-182.
Vikram Talwar, "Insertion loads of the X STOP Interspinous Process Distraction System Designed to Treat Neurogenic Intermittent Claudication", EUR SPINE J. (2006) 15: pp. 908-912.
Walsh et al., Preparation of porous composite implant materials by in situ polymerization of porous apatite containing epsilon-caprolactone or methyl methacrylate. Biomaterials. Jun. 2001; 22( 11): 1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/600/600/620/S20/S045. html>, 2 pages.
Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.
US 5,545,827, 10/03/1995, Aust (withdrawn).
[No. Author Listed] Porocoat@ Porous Coating, Depuy Synthes Companies, 2015, 2 pages, webpage, accessed Jul. 5, 2016, <https://emea.depuysynthes.com/hcp/hip/products/qs/porocoat-porous-coating-emea>.
Alfen, et al., "Developments in the Area of Edoscopic Spine Surgery". European Musculoskeletal Review 2006, pp. 23-24. ThessysTM, Transforminal Endoscopic Spine System. Medical Solutions, ioimax®.
Allcock, "Polyphosphazenes", The Encyclopedia of Polymer Science, vol. 13, pp. 31-41, Wiley Intersciences, John Wiley & Sons, (1988).
Brochure for PERPOS PLS System Surgical Technique by Interventional Spine, 2008, 8 pages.

(56) References Cited

OTHER PUBLICATIONS

Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.
Bruder et al., Monoclonal antibodies reactive with human osteogenic cell surface antigens. Bone. Sep. 1997; 21(3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc.'s Orthopedic Wisorb (TM) Malleolar Screw [online], Jul. 30, 2002 [retrieved on Oct. 14, 2003]. Retrieved from the Internet <URL: http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Cheng, B.C., Ph.D., Biomechanical pullout strength and histology of Plasmapore® XP coated implants: Ovine multi time point survival study. Aesculap Implant Systems, LLC, 2013, 12 pages.
Chiang, "Biomechanical Comparison of Instrumented Posterior Lumbar Interbody Fusion with One or Two Cages by Finite Element Analysis", Spine, Sep. 2006, pp. E682-E689, vol. 31(19), Lippincott Williams & Wilkins, Inc.
Chin, "Early Results of the Triage Medical Percutaneous Transfacet Pedicular BONE-LOK Compression Device for Lumbar Fusion", Accessed online Jul. 10, 2017, 10 pages.
CN Office Action dated Apr. 24, 2020 for ON Application No. 201780040910.
Cohn et al., Biodegradable PEO/PLA block copolymers, Journal of Biomaterials Research, vol. 22, pp. 993-1009, 1988.
Cohn, "Polymer Preprints", ACS Division of Polymer Chemistry, vol. 30(1), 1989, p. 498, (e.g. PEO/PLA).
Edeland, H.G., "Some Additional Suggestions For An Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998; 212:119-132.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Fuchs, "The use of an interspinous implant in conjuction with a graded facetectomy procedure", Spine vol. 30, No. 11, pp. 1266-1272, 2005.
Gore, "Technique of Cervical Interbody Fusion", Clinical Orthopaedics and Related Research, Sep. 1984, pp. 191-195, No. 188.
Gray's Anatomy, Crown Publishers, Inc., 1977, pp. 33-54.
Ha, S. W et al., Topographical characterization and microstructural interface analysis of vacuum-plasma-sprayed titanium and hydroxyapatite coatings on carbon fibre-reinforced poly(etheretherketone), J. Mater. Sci.: Materials in Medicine, 1997, v. 8, pp. 891-896.
Haas, Norbert P., New Products from AO Development [online], May 2002 [retrieved on Oct. 14, 2003], Retrieved from the Internet <URL: http://www.ao.asif.ch/development/pdf_tk_news_02_pdf>.
Hao et al., Investigation of nanocomposites based on semi-interpenetrating network of [L—poly (epsilon- caprolactone)]/[net-poly (epsilon-caprolactone)] and hydroxyapatite nanocrystals. Biomaterials. Apr. 2003; 24(9): 1531-9.
Harsha et al., Tribo performance of polyaryletherketone composites, Polymer Testing (21) (2002) pp. 697-709.
Haynesworth et al., Cell surface antigens on human marrow-derived mesenchymal cells are detected by monoclonal antibodies. Bone. 1992; 13(1):69-80.
Heller, "Poly (Otrho Esters)"; Handbook of Biodegradable Polymers; edited by Domb; et al.; Hardwood Academic Press; 1997; pp. 99-118.
Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Hoogland et al., "Total Lumar Intervertebral Disc Replacement: Testing a New Articulating Space in Human Cadaver Spines-24 1", Annual ORS, Dallas, TX, Feb. 21-23, 1978, 8 pages.
Hunt, "Expandable Cage Placement Via a Posterolateral Approach in Lumbar Spine Reconstructions", Journal of Neurosurgery: Spine, Sep. 2006, pp. 271-274, vol. 5.
International Patent Application No. PCT /US2013/029014, International Search Report dated Jul. 1, 2013, 7 pages.
Iprenburg et al., "Transforaminal Endoscopic Surgery in Lumbar Disc Herniation in an Economic Crisis—The TESSYS Method", US Musculoskeletal, 2008, p. 47-49.
Japanese Office Action for Application No. 2013-542047, dated Sep. 8, 2015 (12 pages).
Japanese Office Action for Application No. 2016-135826, dated Jun. 6, 2017, (7 pages).
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kambin et al., "Percutaneous Lateral Discectomy of the Lumbar Spine: A Preliminary Report", Clin. Orthop,: 1983, 174: 127-132.
Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).
Kemnitzer et al., "Degradable Polymers Derived From The Amino Acid L-Tyrozine", The Handbook of Biodegradable Polymers, edited by Domb, et al., Hardwood Academic Press, 1997, pp. 251-272.
Khoo, "Minimally Invasive Correction of Grade I and II Isthmic Spondylolisthesis using AxiaLIF for L5/S1 Fusion", pp. 1-7, Rev B Sep. 15, 2008.
King., "Internal Fixation for Lumbosacral Fusion, The Journal of Bone and Joint Surgery", J. Bone Joint Surg. Am., 1948; 30: 560-578.
Kotsias, A., Clinical trial of titanium-coated PEEL cages anterior cervical discectomy and fusion. [Klinishe Untersuching zum Einsatz von titanbeschichteten Polyetheretherketon—Implantaten bei der cervikalen interkorporalen fusion]. Doctoral thesis. Department of Medicine, Charite, University of Medicine Berlin, 2014, 73 pages. (German language document/Engl. summary).
Krbec, "Replacement of the Vertebral Body with an Expansion Implant (Synex)", Acta Chir Orthop Traumatol Cech, 2002, pp. 158-162, vol. 69(3).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A. Jan. 30, 2001; 98(3):842-7. Epub Jan. 23, 2001.
Link SB Charite Brochure—Intervertebral Prosthesis 1988, 29 pages.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.
McAfee et al., Minimally invasive anterior retroperitoneal approach to the lumbar spine: Emphasis on the lateral BAK. SPINE. 1998; 23(13): 1476-84.

(56) References Cited

OTHER PUBLICATIONS

U.S. Appl. No. 60/794,171, filed Apr. 21, 2006, entitled Method and Apparatus for Spinal Fixation.

* cited by examiner

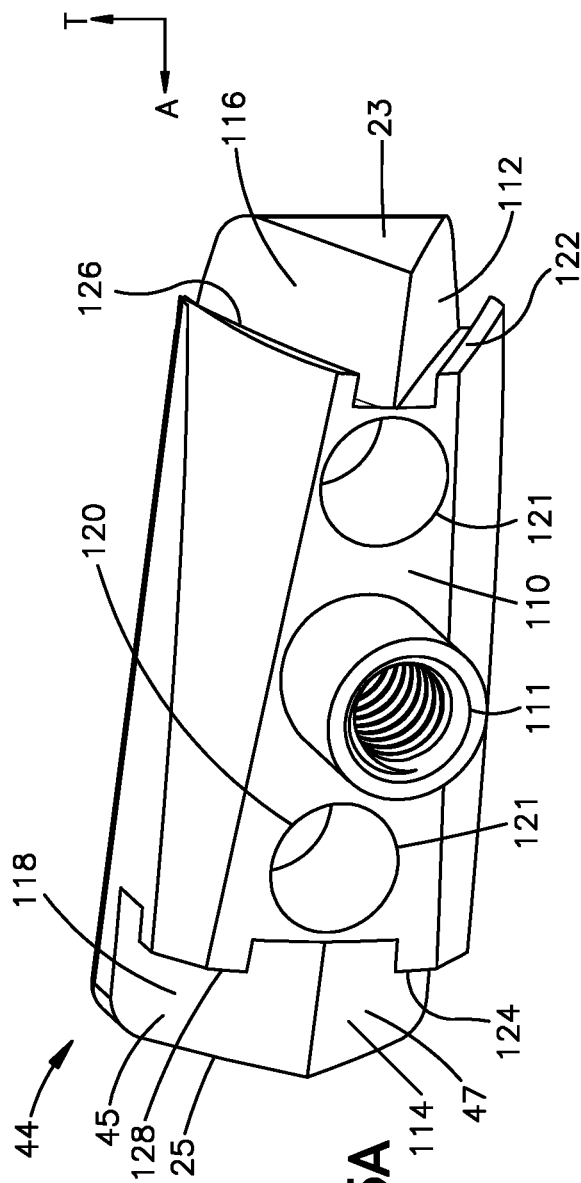
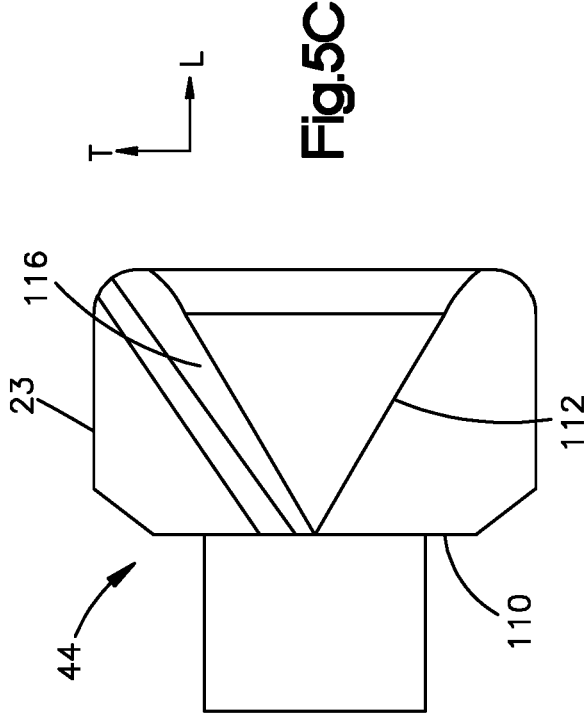
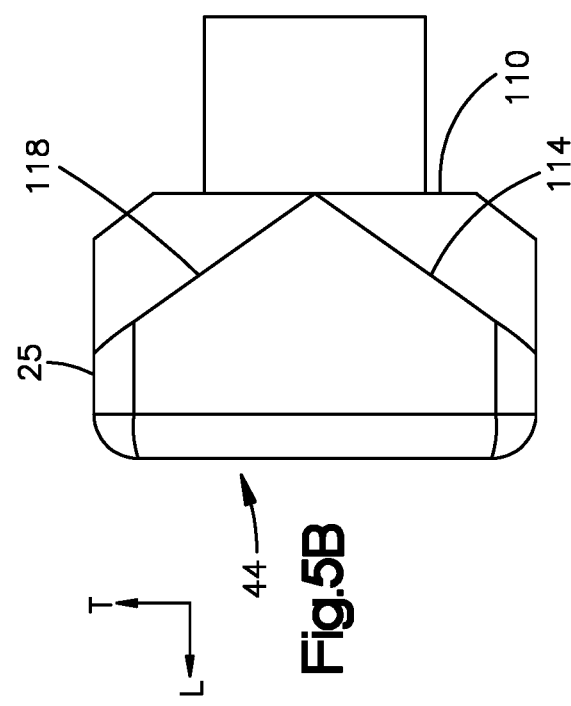

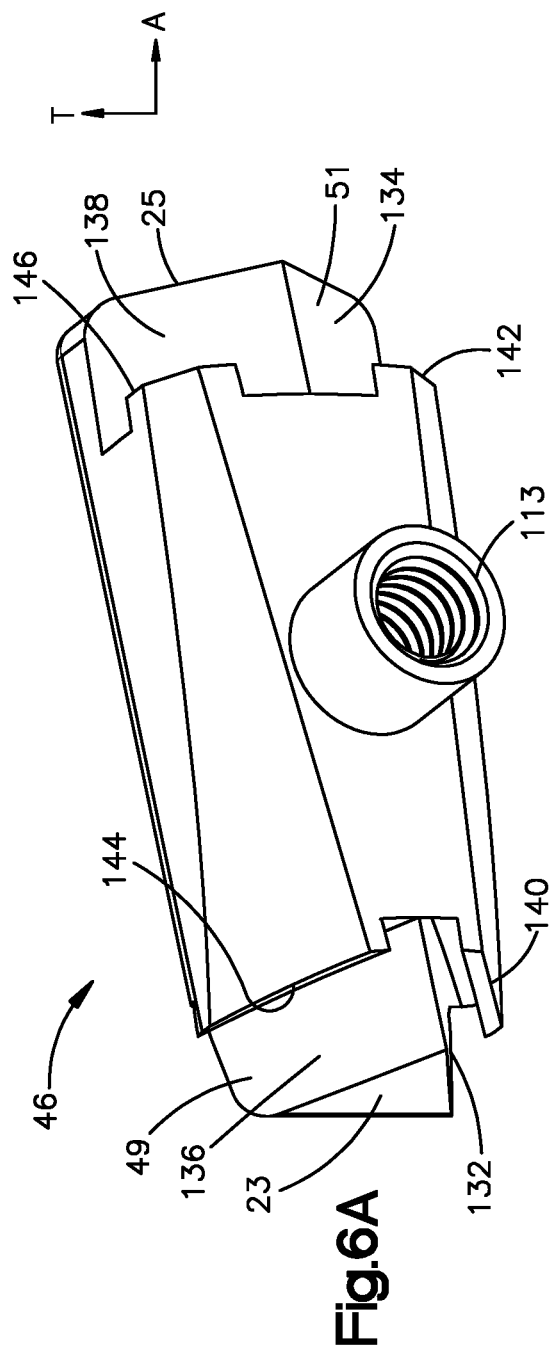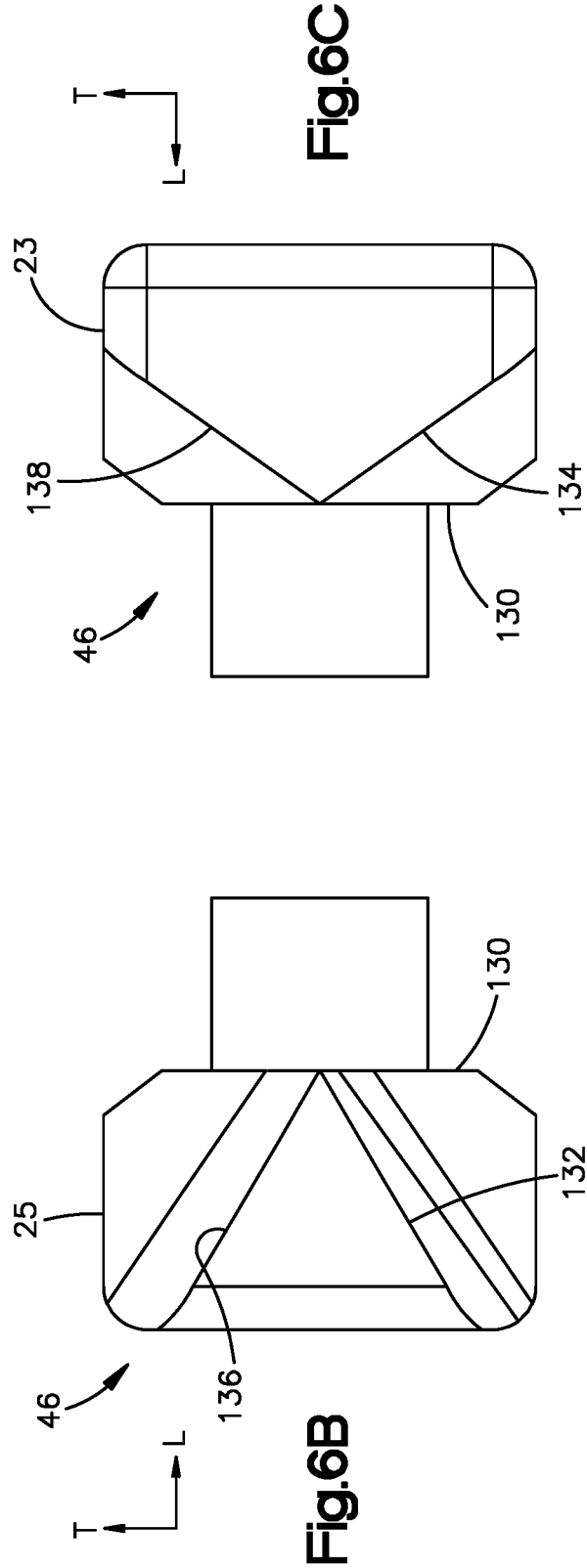

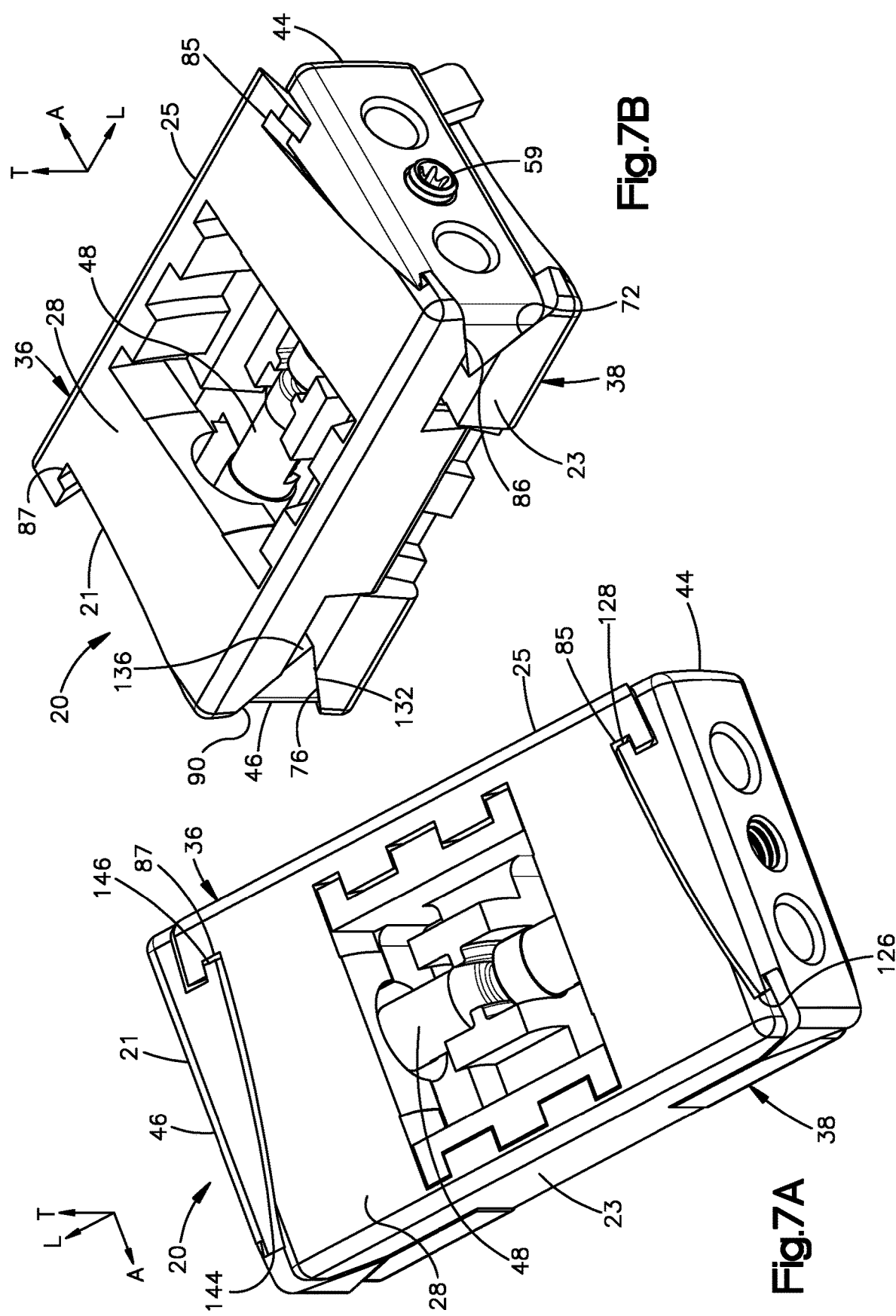

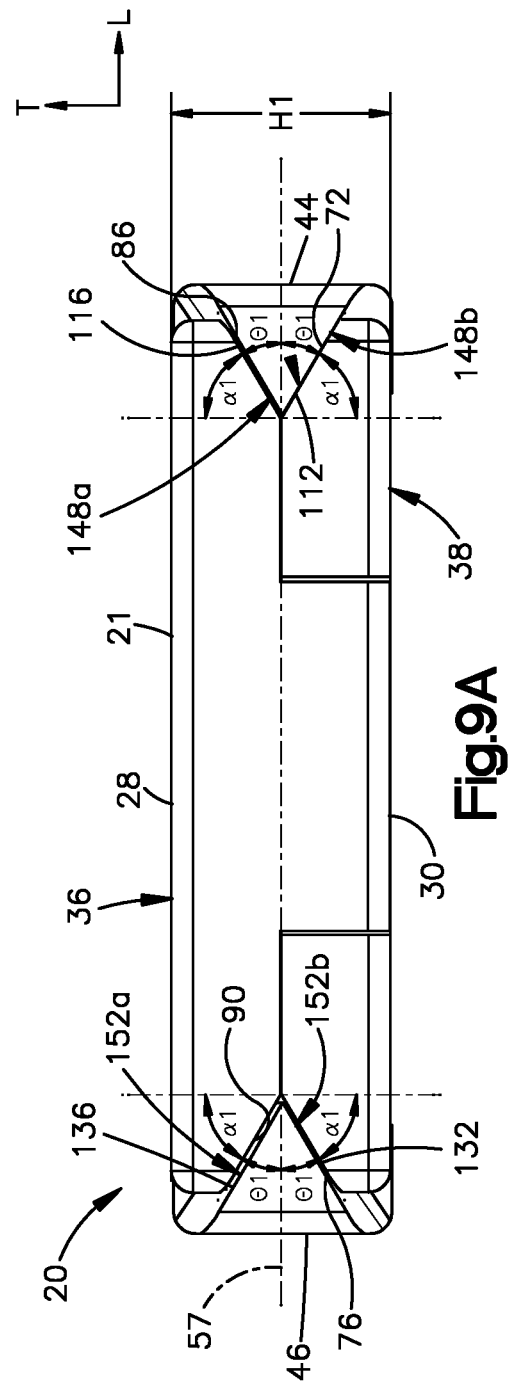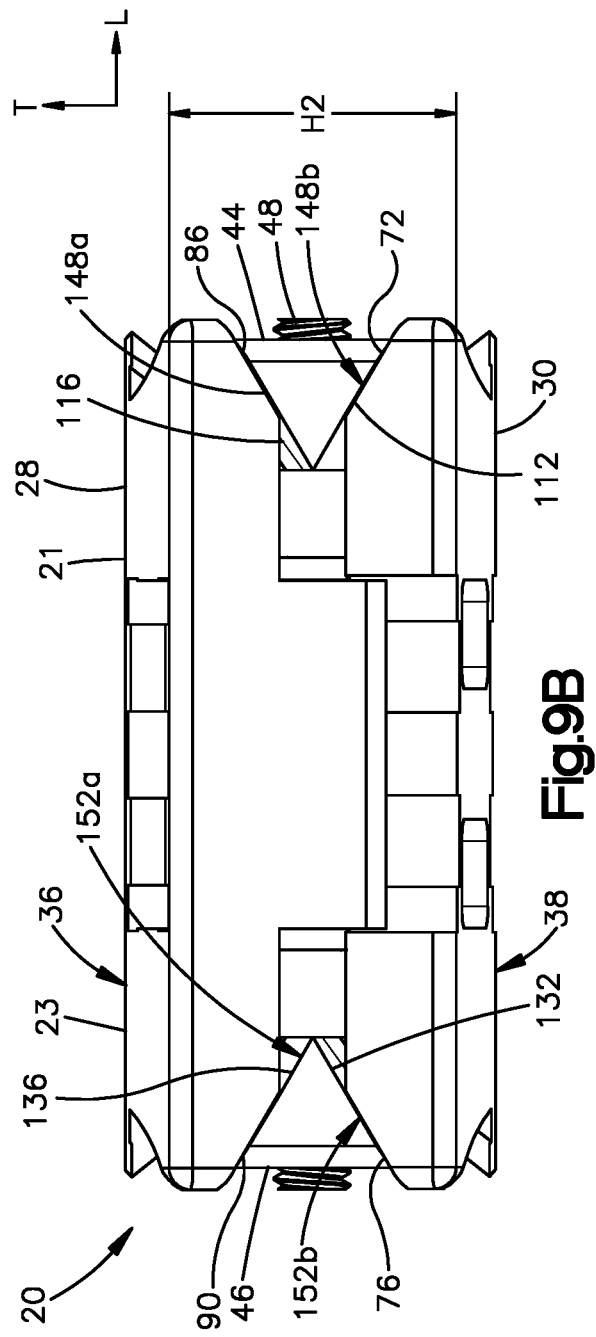

EXPANDABLE LORDOTIC INTERVERTEBRAL FUSION CAGE

TECHNICAL FIELD

The present invention relates to an expandable intervertebral implant.

BACKGROUND

The human spine is comprised of a series of vertebral bodies separated by intervertebral discs. The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1.beta. and TNF-.alpha. as well as matrix metalloproteinases ("MMPs"). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosis. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a device that restores disc height and allows for bone growth therethrough and between the adjacent vertebrae. These devices are commonly called fusion devices, or "interbody fusion devices". Current spinal fusion procedures include transforaminal lumbar interbody fusion (TLIF), posterior lumbar interbody fusion (PLIF), anterior to psoas (ATP), extraforaminal lumbar interbody fusion (ELIF), and lateral lumbar interbody fusion (LLIF) procedures. While interbody fusion devices are known in the art, there continues to be a need for minimally invasive devices that stabilize the spinal segment and create an optimum space for spinal fusion.

SUMMARY

In accordance with one aspect, an expandable intervertebral fusion cage is configured for insertion in an intervertebral space defined between a superior vertebral body and an inferior vertebral body. The fusion cage can include a cage body and an actuator. The cage body can include upper and lower endplate members, and proximal and distal wedge members. The upper endplate member can define an upper bone contacting surface configured to abut the inferior vertebral body, and can include at least one proximal upper ramp surface and at least one distal upper ramp surface. The lower endplate member can define a lower bone contacting surface configured to abut the superior vertebral body, wherein the upper and lower bone contacting surfaces are opposite each other along a transverse direction. The proximal wedge member can have at least one upper ramp surface that abuts the at least one proximal upper ramp surface of the upper endplate member. The distal wedge member can have at least one upper ramp surface that abuts the at least one distal upper ramp surface of the upper endplate member. The proximal and distal wedge members can be opposite each other along a longitudinal direction that is perpendicular to the transverse direction. The cage body can define a first side and a second side opposite the first side along a lateral direction that is perpendicular to each of the longitudinal direction and the transverse direction. The actuator can have an actuator shaft that is coupled to the proximal and distal wedge members, such that movement of the actuator in a first direction causes the proximal and distal wedge members to move in an expansion direction whereby (i) the at least one upper ramp surface of the proximal wedge member rides along the at least one proximal upper ramp surface of the upper endplate member in surface contact with the at least one proximal upper ramp surface of the upper endplate member, and (ii) the at least one upper ramp surface of the distal wedge member rides along the at least one distal upper ramp surface of the upper endplate member in surface contact with the at least one distal upper ramp surface of the upper endplate member, thereby causing an entirety of the upper endplate member to move away from the lower endplate member. Movement of the proximal and distal wedge members in the expansion direction causes the upper endplate member at the second side of the fusion cage to move away from the lower endplate at a greater rate than the upper endplate member at the first side of the fusion cage moves away from the lower endplate member.

BRIEF DESCRIPTION OF THE DRAWINGS

The foregoing summary, as well as the following detailed description of illustrative embodiments of an intervertebral fusion cage of the present application, will be better understood when read in conjunction with the appended drawings. For the purposes of illustrating the expandable fusion cage of the present application, there is shown in the drawings illustrative embodiments. It should be understood, however, that the application is not limited to the precise arrangements and instrumentalities shown. In the drawings:

FIG. 5A is a perspective view of the first wedge member illustrated in FIG. 2;

FIG. 5B is a side elevation view of the first wedge member illustrated in FIG. 5A;

FIG. 5C is another side elevation view of the first wedge member illustrated in FIG. 5A;

FIG. 6A is a perspective view of the second wedge member illustrated in FIG. 2;

FIG. 6B is a side elevation view of the first wedge member illustrated in FIG. 6A;

FIG. 6C is another side elevation view of the first wedge member illustrated in FIG. 6A;

FIG. 7A is a perspective view of the fusion cage illustrated in FIG. 1A, shown in the contracted position;

FIG. 7B is a perspective view of the fusion cage illustrated in FIG. 1B, shown in the expanded position;

FIG. 9A is a side elevation view of a second side of the fusion cage illustrated in FIG. 7A, shown in the contracted position;

FIG. 9B is a side elevation view of the second side of the fusion cage illustrated in FIG. 9A, but shown in the expanded position;

DETAILED DESCRIPTION OF ILLUSTRATIVE EMBODIMENTS

Figure 1A:
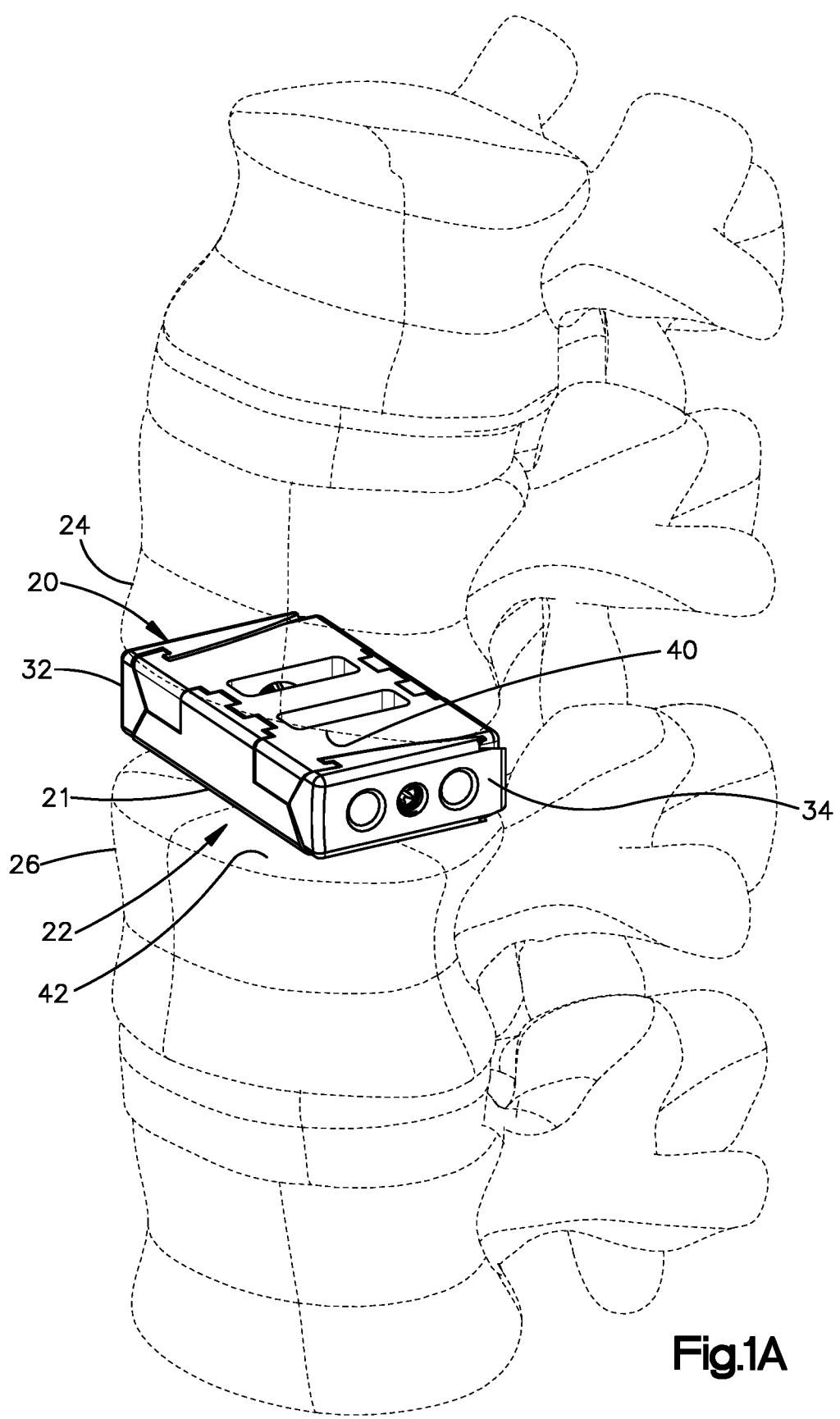
FIG. 1A is a perspective view of an intervertebral fusion cage disposed in an intervertebral space in a contracted position.

Certain terminology is used in the following description for convenience only and is not limiting. The "lower" and "upper" designate directions in the drawings to which reference is made. The words, "anterior", "posterior", "superior," "inferior," "medial," "lateral," and related words and/or phrases are used to designate various positions and orientations in the human body, but also applies to the fusion cage when disposed outside the human body. The terminology includes the above-listed words, derivatives thereof and words of similar import.

Unless otherwise indicated, the terms "substantially," "generally," and "approximately" along with derivatives thereof and words of similar import as used herein with respect to dimensions, values, shapes, directions, and other parameters can include the stated dimensions, values, shapes, directions, and other parameters and up to plus or minus 10% of the stated dimensions, values, shapes, directions, and other parameters, such as up to plus or minus 9% of the stated dimensions, values, shapes, directions, and other parameters, such as up to plus or minus 8% of the stated dimensions, values, shapes, directions, and other parameters, such as up to plus or minus 7% of the stated dimensions, values, shapes, directions, and other parameters, such as up to plus or minus 6% of the stated dimensions, values, shapes, directions, and other parameters, such as up to plus or minus 5% of the stated dimensions, values, shapes, directions, and other parameters, such as up to plus or minus 4% of the stated dimensions, values, shapes, directions, and other parameters, such as up to plus or minus 3% of the stated dimensions, values, shapes, directions, and other parameters, such as up to plus or minus 2% of the stated dimensions, values, shapes, directions, and other parameters, such as up to plus or minus 1% of the stated dimensions, values, shapes, directions, and other parameters.

Method steps and apparatus described or referenced herein will sometimes be described in singular form for clarity. However, it should be appreciated that as used herein, the singular term "a" or "the" with respect to an apparatus or method step can include the plural apparatus or method steps. Conversely, the plural term as used herein with respect to apparatus or method steps can include the singular "a" or "the." Thus, it should be appreciated that the use herein of the singular term "a" or "the" and the use herein of the plural term can equally apply to "at least one" unless otherwise indicated.

Referring to FIG. 1A, an intervertebral implant or fusion cage 20 can be inserted into an intervertebral space 22 in an initial or contracted position. The intervertebral space 22 can be disposed anywhere along the spine as desired, including at the lumbar region, thoracic region, or cervical region of the spine. The intervertebral space 22 can be defined by a first or superior vertebral body 24 and a second or inferior vertebral body 26. The superior vertebral body 24 defines a superior vertebral surface 40, and the adjacent inferior vertebral body 26 defines an inferior vertebral surface 42. The superior vertebral surface 40 and the inferior vertebral surface 42 can face each other so as to define the intervertebral space 22. The vertebral bodies 24 and 26 can be anatomically adjacent vertebral bodies, or can remain after a vertebral body has been removed from a location between the vertebral bodies 24 and 26, for instance during a corpectomy procedure. The intervertebral space 22 of FIG. 1A is illustrated after a discectomy has been performed, whereby the disc material has been removed or at least partially removed to prepare the intervertebral space 22 to receive the fusion cage 20.

The fusion cage 20 can be inserted into the intervertebral space 22 along any suitable approach as desired, such as a lateral approach during a lateral lumbar interbody fusion (LLIF) procedure. The fusion cage 20 thus defines a distal end 32 which can also define a leading end of the fusion cage 20 with respect to insertion into the intervertebral space 22, and a proximal end 34 that can also define a trailing end of the fusion cage 20 that is opposite the distal end 32. As used herein, the term "proximal" and derivatives thereof refer to a direction from the distal end 32 toward the proximal end 34. As used herein, the term "distal" and derivatives thereof refer to a direction from the proximal end 34 toward the distal end 32. The proximal and distal ends 34 can be opposite each other along a longitudinal direction L, which can be oriented substantially along the medial-lateral direction when the fusion cage 20 is disposed in the intervertebral space 22. The fusion cage 20 is designed and configured to be inserted into an intervertebral space in a direction from the trailing end 34 toward the insertion end 32, also referred to herein as an insertion direction. The insertion direction can also be oriented along the longitudinal direction L.

Figure 1B:
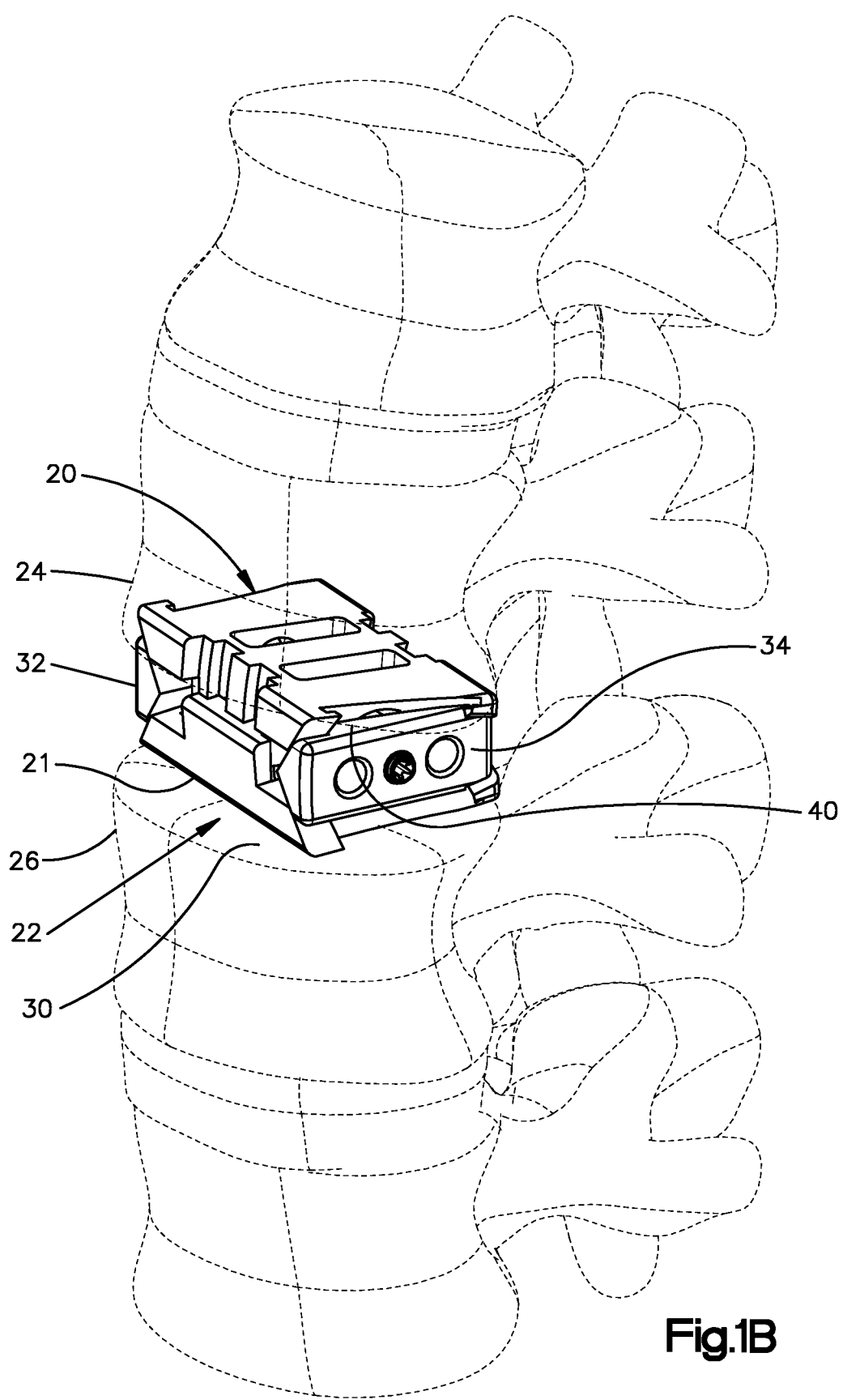
FIG. 1B is a perspective view of the fusion cage illustrated in FIG. 1A, but shown expanded from the contracted position to an expanded position.

Referring now to FIG. 1B, once the fusion cage 20 has been inserted into the intervertebral space 22, the fusion cage 20 can be expanded from the first or contracted position to a second or expanded position. The fusion cage 20 achieves a height in the expanded position that is greater than the height of the fusion cage 20 in the contracted position. Further, the fusion cage 20 can angulate to achieve a lordotic profile as it expands from the contracted position to the expanded position. The fusion cage 20 can therefore be said to undergo lordotic expansion as it iterates from the contracted position to the expanded position. As a result, the fusion cage 20 can achieve height restoration of the intervertebral space 22 while supporting the vertebral bodies 24 and 26 in alignment with each other consistent with the natural curvature of the spine.

Figure 2:
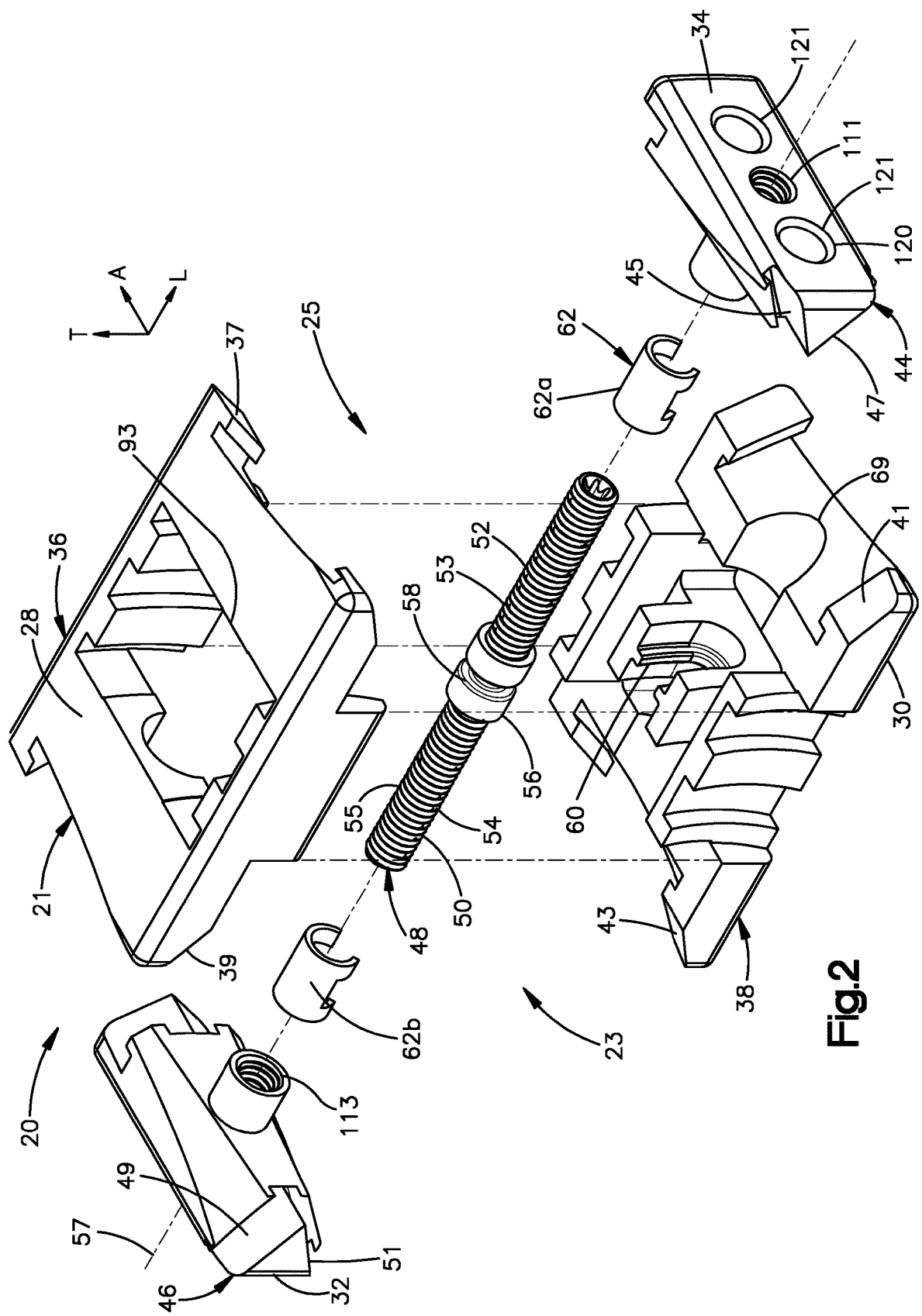
FIG. 2 is an exploded perspective view of the fusion cage illustrated in FIG. 1A, including upper and lower endplate members, first and second wedge members, an actuator shaft, and at a pair of stop members.

Referring also to FIG. 2, the expandable fusion cage 20 defines a cage body 21 having an upper endplate member 36 and a lower endplate member 38 opposite the upper endplate member along a transverse direction T that is perpendicular to the longitudinal direction L. The cage body 21, and thus each of the upper and lower endplate members 36 and 38 defines a first side 23 and a second side 25 opposite the first side 23 along a lateral direction A that is perpendicular to each of the longitudinal direction L and the transverse direction T. A first lateral direction is thus established from the second side 25 toward the first side 23. A second lateral direction opposite the first lateral direction is established from the first side 23 toward the second side. The endplate members 36 can be formed of polyether ether ketone (PEEK) or any other suitable biocompatible polymeric material. Alternatively, the upper and lower endplate members 36 and 38 can be made of any suitable biocompatible metal such as a titanium-aluminum-niobium (TAN) alloy. It should be appreciated that the any suitable alternative material can be used to form the endplate members 36 and 38 as desired.

The upper endplate member 36 defines an upper bone contacting surface 28 that is configured to abut or grip the superior vertebral surface 40. The lower endplate member 38 defines a lower bone contacting surface 30 that is configured to abut or grip the inferior vertebral surface 42. The bone contacting surfaces 28 and 30 can be opposite each other along the transverse direction T. Each of the upper and lower bone contacting surfaces 28 and 30 can be convex or partially convex, for instance, one portion of the surface is convex while another portion can be substantially planar. Alternatively, each of the upper and lower bone contacting surfaces 28 and 30 can be substantially planar along their respective entireties. While the upper and lower bone contacting surfaces 28 and 30 are shown as smooth in FIG. 2, it is recognized that the upper and lower endplate members 36 and 38 can include any suitable texture that extends from the upper and lower bone contacting surfaces 28 and 30, such as teeth, spikes, ridges, cones, barbs, indentations, or knurls, which are configured to grip the superior and inferior vertebral bodies 24 and 26, respectively, to resist migration of the fusion cage 20 in the intervertebral space 22.

The upper endplate member 36 further defines at least one first or proximal upper ramp surface 37 and at least one second or distal upper ramp surface 39. Similarly, the lower endplate member 38 defines at least one first or proximal lower ramp surface 41 and at least one second or distal lower ramp surface 43. The at least one first upper ramp surface 37 can be generally aligned with the at least one first lower ramp surface 41 along the transverse direction T. Similarly, the at least one second upper ramp surface 39 can be generally aligned with the at least one second lower ramp surface 43 along the transverse direction T. The at least one first upper ramp surface 37 can extend generally toward the upper bone contacting surface 28 as it extends in the proximal direction. The at least one second upper ramp surface 39 can extend generally toward the upper bone contacting surface 28 as it extends in the distal direction. The at least one first lower ramp surface 41 can extend generally toward the lower bone contacting surface 30 as it extends in the proximal direction. The at least one second lower ramp surface 43 can extend generally toward the lower bone contacting surface 30 as it extends in the distal direction.

The fusion cage 20 is initially inserted into the intervertebral space 22 in the contracted position, the fusion cage 20 defines a first height (see FIG. 8A) from the upper endplate surface 28 to the lower endplate surface 30 along the transverse direction T. The first height can be less than the distance between the superior vertebral surface 40 and the inferior vertebral surface 42 along the transverse direction T. Thus, in some examples, the fusion cage 20 can be inserted into the intervertebral space 22 without distracting the superior and inferior vertebral bodies 24 and 26, respectively, away from each other.

The cage body 21, and thus the fusion cage 20, further includes at least one wedge member disposed between the upper and lower endplate members 36 and 38. The at least one wedge member has at least one ramp surface, and is configured to move in an expansion direction, which causes the at least one ramp surface to ride along a corresponding at least one ramp surface of at least one of the upper endplate member 36 and the lower endplate member 38 to move away from the other of the upper endplate member 36 and the lower endplate member 38, and to angulate with respect to the other of the upper endplate member 36 and the lower endplate member 38 along a direction that is angularly offset (such as perpendicular) with respect to each of the transverse direction T and the expansion direction.

The at least one wedge member can include a first or proximal wedge member 44 and a second or distal wedge member 46 opposite the first wedge member 44 along the longitudinal direction L. The wedge members 44 and 46 can be made of any suitable biocompatible polymer such as PEEK, or any suitable metal or metal alloy such as titanium, TAN, stainless steel, or the like. When the fusion cage 20 is in the contracted position, the first wedge member 44 can be disposed at the trailing end 34 of the fusion cage 20, and the second wedge member 46 can be disposed at the leading end 32 of the fusion cage 20. The first and second wedge members 44 and 46 are configured to move from an initial position in an expansion direction that urges at least one or both of the upper and lower endplate members 36 and 38 to move away from the other of the upper and lower endplate members 36 and 38 along the transverse direction T, thereby expanding the cage body 21 and thus the fusion cage 20 from the contracted position to the expanded position. When the wedge members 44 and 46 are in the initial position, the fusion cage 20 is in the contraction position.

In particular, the first wedge member 44 can include at least one upper proximal ramp surface 45 and at least one lower proximal ramp surface 47. The second wedge member 46 can similarly include at least one upper distal ramp surface 49 and at least one lower distal ramp surface 51. The at least one upper ramp surface 45 and the at least one lower ramp surface 47 of the first wedge member 44 can be configured to ride along the at least one first upper ramp surface 37 of the upper endplate member 36 and the at least one first lower ramp surface 41 of the lower endplate member 38, respectively. In this regard, the first wedge member 44 can urge either or both of the upper and lower endplate members 36 and 38 away from the other of the upper and lower endplate members 36 and 38 during movement of the first wedge member 44 in the expansion direction. Similarly, the at least one upper ramp surface 49 and the at least one lower ramp surface 51 of the second wedge member 46 can be configured to ride along the at least one second upper ramp surface 39 of the upper endplate member 36 and the at least one second lower ramp surface 43 of the lower endplate member 38, respectively. In this regard, the second wedge member 46 can urge either or both of the upper and lower endplate members 36 and 38 away from the other of the upper and lower endplate members 36 and 38 during movement of the second wedge member 46 in the expansion direction.

The ramp surfaces of the upper and lower endplate members 36 and 38 and the ramp surfaces of the first and second wedge members 44 and 46 can be nonplanar. In particular, as described in more detail below, the ramp surfaces of the upper and lower endplate members 36 and 38 and the ramp surfaces of the first and second wedge members 44 and 46 can be shaped such that the second side 25 of the fusion cage 20 expands at a greater rate of expansion than the first side 23 of the fusion cage 20. That is, movement of the first and second wedge members 44 and 46 in the expansion direction causes the upper endplate member 36 at the second side 25 of the fusion cage 20 to move away from the lower endplate 38 along the transverse direction T at a greater rate than the upper endplate member 36 at the first side 23 of the fusion cage 20 moves away from the lower endplate member 38. Further, movement of the first and second wedge members 44 and 46 in the expansion direction causes the lower endplate member 38 at the second side 25 of the fusion cage 20 to move away from the upper endplate 36 along the transverse direction T at a greater rate than the lower endplate member 38 at the first side 23 of the fusion cage 20 moves away from the lower endplate member 38. Accordingly, the second side 25 of the fusion cage can achieve a greater height than the first side 23 along the transverse direction T when the implant is in the expanded position. Thus, either or both of the bone contacting surfaces 28 and 30 can be sloped toward the other of the bone contacting surfaces 28 and 30 as they extend in the second lateral direction. As a result, the fusion cage 20 can define a lordotic profile (or kyphotic profile if the fusion cage 20 is a cervical fusion cage) to assist in restoring the natural curvature of the spine when the fusion cage 20 is implanted and in the expanded position.

The first and second wedge members 44 and 46 are also configured to move in a contraction direction that urges or permits at least one or both of the upper and lower endplate members 36 and 38 to move toward the other of the upper and lower endplate members 36 and 38 along the transverse direction T, thereby iterating the cage body 21 and thus the fusion cage 20 from the contracted position to the expanded position. As will be described in more detail below, the first wedge member 44 can be configured to couple to one or more instruments configured to insert the fusion cage 20 into the intervertebral space and/or expand the fusion cage 20 from the contracted position to the expanded position and/or inject bone graft material into the fusion cage 20. In particular, the first wedge member 44 can also receive bone graft material that promotes fusion of the fusion cage 20 to the superior and inferior vertebral bodies 24 and 26, respectively.

The fusion cage 20 further includes an actuator 48 that is coupled to each of the first and second wedge members 44 and 46, and is configured to cause the first and second wedge members 44 and 46 to move selectively in a first or expansion direction that causes the fusion cage 20 to iterate from the contracted position to the expanded position, and a second or contraction direction that causes the fusion cage 20 to iterate from the expanded position to the contracted position. The expansion direction and the contraction direction can be oriented opposite each other along the longitudinal direction L.

The actuator 48 can include an actuator shaft 50 that extends along a central axis 57 that is oriented along the longitudinal direction L. Thus, the central axis 57 can extend along a straight linear direction. The central axis 57 can further define a central axis of the fusion cage 20. The central axis 57 can divide the fusion cage 20 between the first side 23 and the second side 25. Otherwise stated, the first and second sides 23 and 25 are on opposite sides of the central axis 57 with respect to the lateral direction A.

The actuator shaft 50 can be coupled to each of the first and second wedge members 44 and 46. For instance, the actuator shaft 50 has a first or proximal section 52, and a second or distal section 54 opposite the first section 52 and aligned with the first section 52 along the longitudinal direction L. The first and second sections 52 and 54 can be monolithic with each other, and part of the same single unitary structure that defines the actuator 48. At least a portion up to an entirety of the first section 52 can include at least one external thread that defines a first or proximal threaded portion 53 that extends along at least a portion up to an entirety of the first section 52. Similarly, at least a portion up to an entirety of the second section 54 can include at least one external thread that defines a second or distal threaded portion 55 that extends along at least a portion up to an entirety of the second section 54. The actuator 48 can formed from a biocompatible polymeric material or metallic alloy, such as a titanium or steel. In one example, the intervertebral fusion cage 20 includes the single actuator 48 having the single actuator shaft 50, such that the actuator 48 defines the only actuator shaft 50 of the fusion cage 20 that is coupled to wedge members.

As will be described in more detail below, the first threaded portion 53 can be threadedly mated with the first wedge member 44, and the second threaded portion 55 can be threadedly mated with the second wedge member 46. Thus, rotation of the actuator 48, and thus of the actuator shaft 50, causes the first and second wedge members 44 and 46 to translate along the same single actuator shaft 50, for instance along the first and second sections 52 and 54, respectively. In particular, the first wedge member 44 translates along the first threaded portion 53, and the second wedge member 46 translates along the second threaded portion 55. In one example, the translation of the first and second wedge members 44 and 46 along the actuator shaft 50 can be a pure translation, meaning that the first and second wedge members 44 and 46 do not rotate about the central axis 57 of the actuator shaft 50 with respect to the upper and lower endplate members 36 and 38 as they translate along the actuator shaft 50.

The first threaded portion 53 can have a first thread pattern, and the second threaded portion 55 can have a second thread pattern that is opposite the thread first threaded portion 53. For instance, the first threaded portion 53 can have a right-hand thread pattern, and the second threaded portion 55 can have a left-hand thread pattern. Accordingly, rotation of the actuator shaft 50 in a first direction of rotation causes the wedge members 44 and 46 to move toward each other in the expansion direction. Rotation of the actuator shaft 50 in a second direction of rotation opposite the first direction of rotation causes the wedge members 44 and 46 to move away from each other in the contraction direction. Further, the first threaded portion 53 and the second threaded portion 55 can define equal and opposite thread pitches, such that the wedge members 44 and 46 move at the same rate along the actuator shaft 50 in both the expansion direction and in the contraction direction. Alternatively, the first threaded portion 53 and the second threaded portion 55 can define unequal and opposite thread pitches, such that one of the first and second wedge members 44 and 46 moves at a first rate along the actuator shaft 50, and the other of the first and second wedge members 44 and 46 moves at a second rate different than the first rate along the actuator shaft 50. Thus, respective proximal and distal ends of the cage body 21 can be expanded at different rates, thereby imparting a wedge shape to the cage body 21 in the medial-lateral direction when the fusion cage 20 is in the expanded position. While rotation of the actuator 48 causes the wedge members 44 and 46 to selectively move in the expansion direction and the contraction in one example, it is appreciated in other examples that the actuator 48 can be alternatively constructed as desired, such that any suitable movement of the actuator 48 causes the wedge members 44 and 46 to selectively move in the expansion direction and contraction direction.

In one example, the first and second wedge members 44 and 46 move toward each other in the expansion direction, and move away from each other in the contraction direction. It is recognized in other embodiments that the upper and lower endplate members 36 and 38 and the first and second wedge members 44 and 46 can be configured such that the first and second wedge members 44 and 46 move away from each other in the expansion direction, and toward each other in the contraction direction.

The actuator 48 can further include a locating flange 56 that projects radially out from the actuator shaft 50. The locating flange 56 can engage one of the upper and lower endplate members 36 and 38 so as to prevent or limit movement of the actuator 48 relative to the endplate members 36 and 38 along the longitudinal direction L during use, while permitting rotation of the actuator 48 relative to the endplate members 36 and 38. In one example, the actuator 48 includes a slot 58 that extends into the locating flange 56 and is configured to receive a complementary projection 60 of the lower endplate member 38 to prevent movement of the actuator 48 along the longitudinal direction L. Alternatively, the actuator 48 can include a projection that is received in a slot of the lower endplate member 38 both when the fusion cage 20 is in the contracted position and when the fusion cage 20 is in the expanded position.

The fusion cage 20 can further include at least one stop member 62 that is configured to limit expansion of the fusion cage 20, thereby preventing overexpansion of the fusion cage. For instance, the at least one stop member 62 can include a first or proximal stop member 62a and a second or distal stop member 62b. The stop members 62a-b can be configured as sleeves that can be disposed about the first and second sections 52 and 54, respectively, of the actuator shaft 50. The stop members 62a-b can be unthreaded or otherwise not threadedly coupled to the actuator shaft 50. The first stop member 62a can be disposed between the locating flange 56 and the first wedge member 44, and the second stop member 62b can be disposed between the locating flange 56 and the second wedge member 46. As will be described in more detail below, the first and second stop members 62a and 62b can abut the locating flange 56 and the first and second wedge members 44 and 46, respectively, when the fusion cage 20 is moved from the contracted position to the expanded position so as to prevent further expansion of the fusion cage 20.

The lower endplate member 38 will now be described with reference to FIGS. 2 and FIGS. 3A-3B. The lower endplate member 38 can include a lower plate portion 64 having an outer surface 65 that defines the lower bone contacting surface 30, and an inner surface 67 opposite the outer surface 65. The lower endplate member 38 can further include at least one bone graft aperture that extends through the lower plate portion 64 from the lower bone contacting surface 30 to the inner surface 67. The bone graft aperture is configured to receive bone graft material to enhance fusion of the lower endplate member 38 with the inferior vertebral body 26. The lower endplate member 38 can include recesses 69 that are configured to receive at least a portion of the actuator 48 when the fusion cage 20 is in the contracted position.

The lower endplate member 38 can include a cradle 66 that extends from the inner surface 67. The cradle 66 includes first and second opposed cradle side walls 68 and 70, respectively that are spaced from each other along the lateral direction A and sized to receive and engage the locating flange 56 of the actuator 48. The cradle 66 can further include at least one projection 60 extends from either or both of the first and second cradle walls 68 and 70 toward the other of the first and second cradle walls 68 and 70. The projection 60 is sized to be inserted in the slot 58 of the locating flange 56 when the cradle is inserted into the cradle 66. Accordingly, the cradle 66 of the lower endplate member 38 can interlock with the actuator 48 to limit or prevent the actuator 48 from translating along the longitudinal direction L with respect to the lower endplate member 38. The actuator 48 is rotatable in the cradle about the central axis 57 in the manner described above. The cradle 66 can be substantially U-shaped or alternatively shaped as desired. The at least one projection 60 can be configured as a single projection that extends along each of the first and second cradle walls 68 and 70. Alternatively, the at least one projection 60 can include a first projection that extends along the first cradle wall 68 and a second projection separate from the first projection that extends along the second cradle wall 70.

Figure 10A:
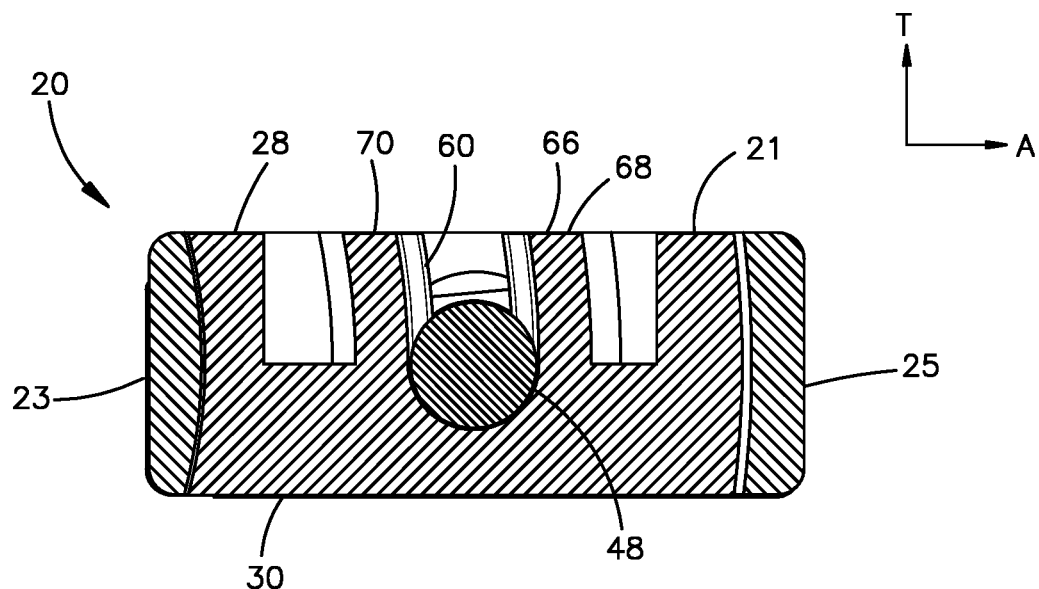
FIG. 10A is a cross-sectional view of the fusion cage illustrated in FIG. 9A, showing the actuator in a fully seated position when the fusion cage is in the contracted position.
Figure 10B:
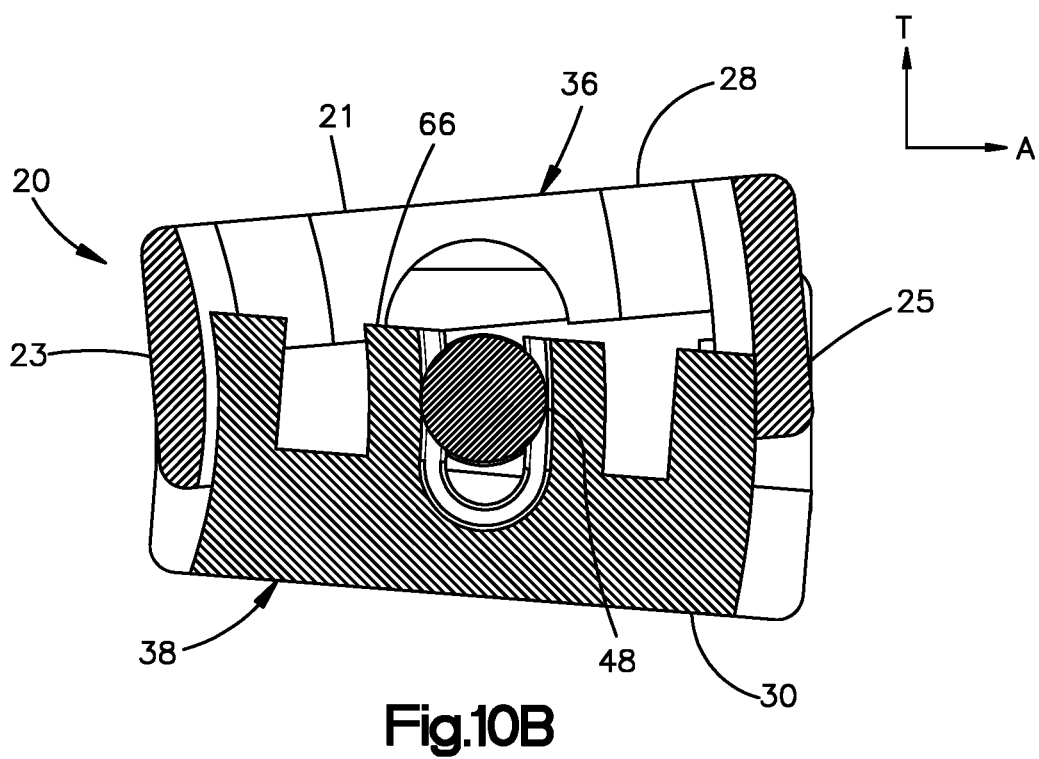
FIG. 10B is a cross-sectional view of the fusion cage illustrated in FIG. 10A, showing the actuator in an elevated position when the fusion cage is in the expanded position.

In one example, the first cradle wall 68 can define a concave surface that faces the second cradle wall 70, and the second cradle wall can define a convex surface that faces the first cradle wall 68. The projection 60 at the first cradle wall 68 can extend along the concave surface, and thus can similarly be concave. Similarly, the projection 60 at the second cradle wall 70 can extend along the convex surface, and can thus similarly be convex. Thus, the cradle 66 can define a central cradle axis that extends along a curved path in the first lateral direction from the second side 25 of the fusion cage 20 toward the first side 23 of the fusion cage 20 as it extends upward or superiorly. In one example, the curved path can be an arcuate path. As illustrated in FIGS. 10A-10B, the lordotic expansion of the fusion cage 20 can cause the actuator 48 to travel along the curved path as the fusion cage moves between the contracted position to the expanded position.

Figure 3A:
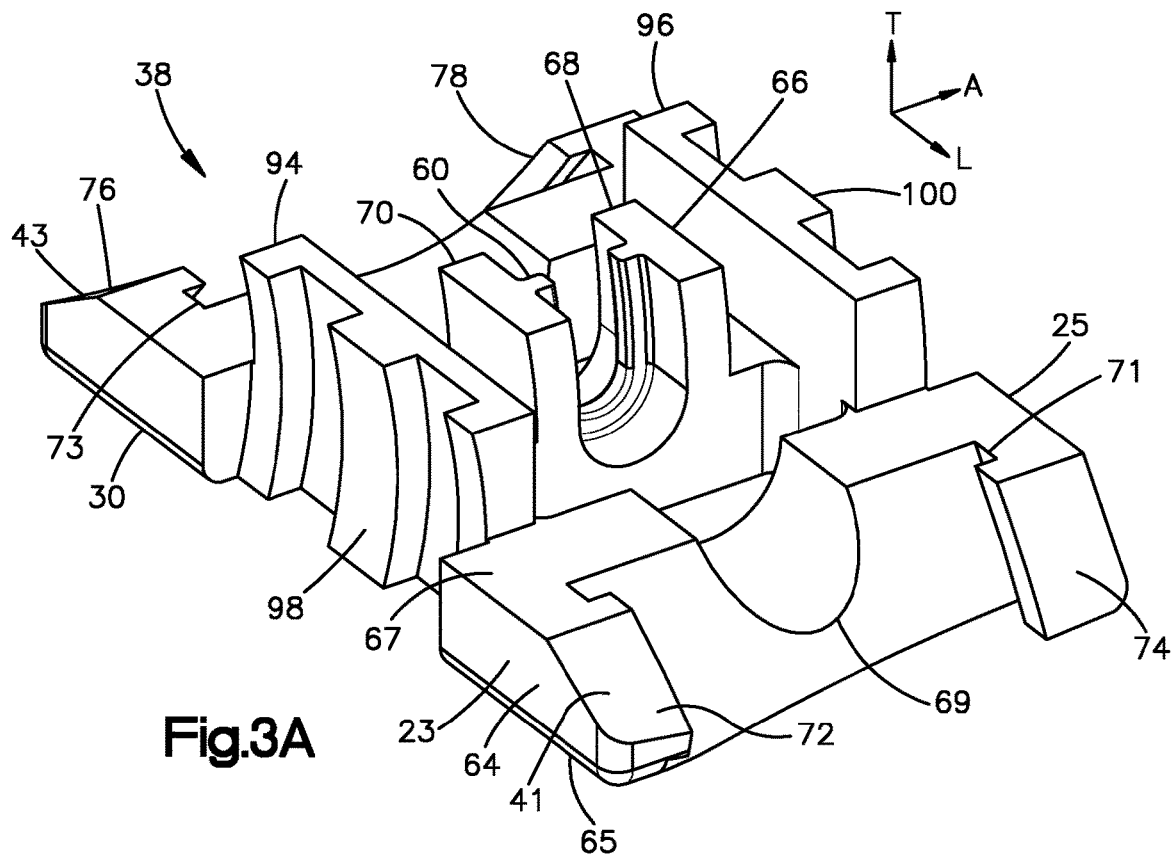
FIG. 3A is a perspective view of the lower endplate member illustrated in FIG. 2.
Figure 3B:
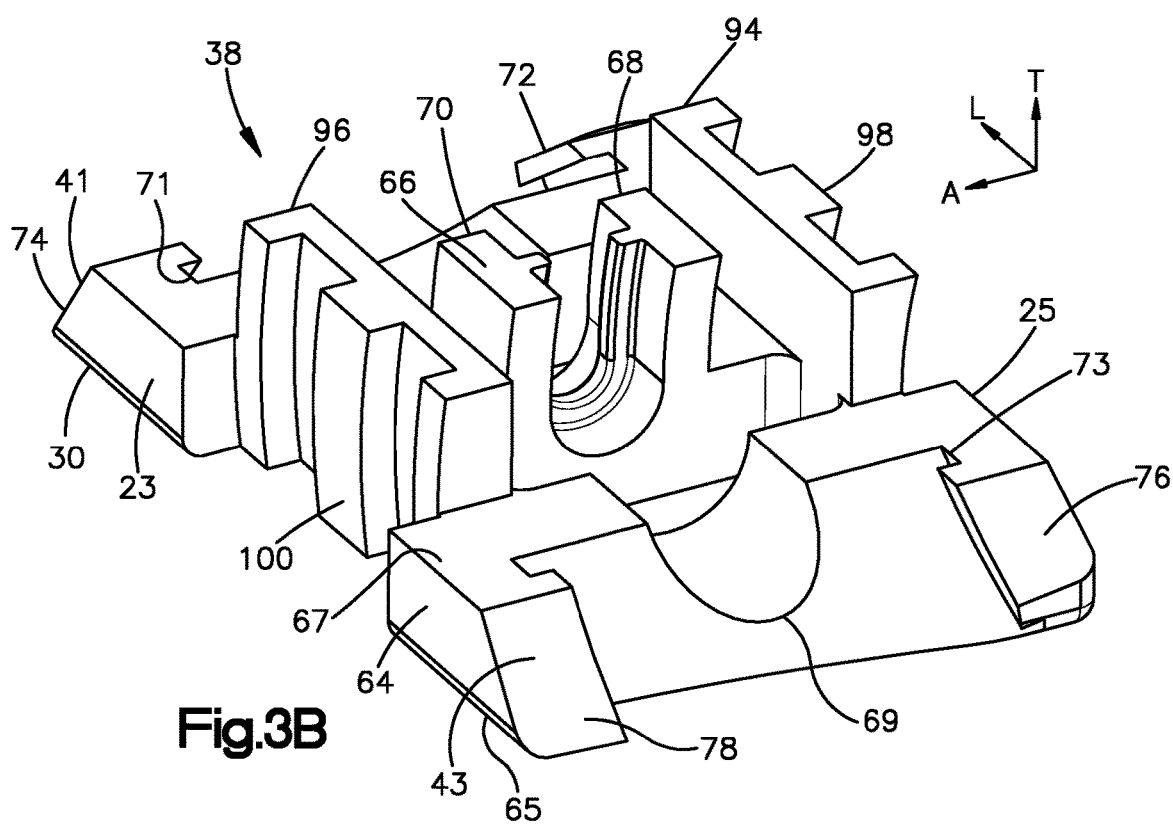
FIG. 3B is another perspective view of the lower endplate member illustrated in FIG. 3A.

With continuing reference to FIG. 2 and FIGS. 3A-3B, and as described above, the lower endplate member 38 can include at least one first lower ramp surface 41 and the at least one second lower ramp surface 43, which can each be opposite the lower bone contacting surface 30 along the transverse direction T. For instance, the at least one first lower ramp surface 41 and the at least one second lower ramp surface 43 can be mirror images of each other. The at least one first lower ramp surface 41 can include first and second ramp surfaces 72 and 74, respectively, and the at least one second lower ramp surface 43 can include third and fourth ramp surfaces 76 and 78, respectively. The first and second ramp surfaces 72 and 74 can be referred to as first and second lower proximal ramp surfaces, respectively, of the lower endplate member 38. The third and fourth ramp surfaces 76 and 78 can be referred to as first and second lower distal ramp surfaces, respectively, of the lower endplate member 38.

The first ramp surface 72 of the lower endplate member 38 can be disposed at the first side 23 of the fusion cage 20, and the second ramp surface 74 can be disposed at the second side 25 of the fusion cage 20. The first and second ramp surfaces 72 and 74 of the lower endplate member 38 can be spaced from each other and opposite each other along the lateral direction A. The third ramp surface 76 of the lower endplate member 38 can be disposed at the first side 23 of the fusion cage, and the fourth ramp surface 78 can disposed at the second side 25 of the fusion cage. The third and fourth ramp surfaces 76 and 78 of the lower endplate member 38 can be spaced from each other and opposite each other along the lateral direction A. The first ramp surface 72 and the third ramp surface 76 can be aligned with each other along the longitudinal direction L, and the second ramp surface 74 and the fourth ramp surface 78 can be aligned with each other along the longitudinal direction L. In this regard, the first ramp surface 72 and the third ramp surface 76 can be mirror images of each other. Similarly, the second ramp surface 74 and the fourth ramp surface 78 can be mirror images of each other.

As described above, the fusion cage 20 can be configured to undergo lordotic expansion. Thus, the first and third ramp surfaces 72 and 76 can define a first ramp angle with respect to the longitudinal direction L (or a plane that includes the longitudinal direction L and the lateral direction A), and the second and fourth ramp surfaces 74 and 78 can define a second ramp angle with respect to the longitudinal direction L (or a plane that includes the longitudinal direction L and the lateral direction A) that is greater than the first ramp angle. As will be appreciated from the description below, the first, second, third, and fourth ramp surfaces 72-78 of the lower endplate member can be in surface contact with the proximal and distal wedge members 44 and 46, respectively, as the wedge members urge the lower endplate member 38 away from the upper endplate member 36. Further, the first, second, third and fourth ramp surfaces 72-78 are included in the same unitary singular lower endplate member 38, and can be constructed so as to not rotate with respect to each other during movement of the cage body 21 from the contracted position toward the expanded position. Thus, the first, second, third and fourth ramp surfaces 72-78 can be said to be rotatably fixed with respect to each other. Thus, the first ramp angle can be referred to as a fixed first ramp angle, and the second ramp angle can be referred to as a second fixed ramp angle.

Advantageously, the first and second wedge members 44 and 46, respectively, can be configured to maintain surface contact with each of the ramp surfaces 72-78 of the lower endplate member 38 as the fusion cage 20 iterates between the contracted position and the expanded position. Accordingly, each of the first and second ramp surfaces 72 and 74 of the lower endplate member 38 and the third and fourth ramp surfaces 76 and 78 of the lower endplate member 38 can extend along respective nonplanar paths. In one example, the first and second ramp surfaces 72 and 74 of the lower endplate member 38 and the third and fourth ramp surfaces 76 and 78 of the lower endplate member 38 can extend along respective twisted paths. For instance, the first and second ramp surfaces 72 and 74 of the lower endplate member 38 can extend along respective helical paths. The helical paths of the first and second ramp surfaces 72 and 74 can be defined by a common helical pitch, but defined by different helical radii. For instance, the helical paths of the first and second ramp surfaces 72 and 74 can be defined by a single swept helix. Similarly, the third and fourth ramp surfaces 76 and 78 of the lower endplate member 38 can extend along respective helical paths. The helical paths of the third and fourth ramp surfaces 76 and 78 can be defined by the same helical pitch, but defined by different helical radii. For instance, the helical paths of the third and fourth ramp surfaces 76 and 78 can be defined by a single swept helix. The helical paths can be concave in one example.

In one example, the first and second ramp surfaces 72 and 74 extend along a first single lower helical path that is continuous from the first ramp surface 72 to the second ramp surface 74. Similarly, the third and fourth ramp surfaces 76 and 78 can extend along a second single lower helical path that is continuous from the third ramp surface 76 to the fourth ramp surface 78. The first and second lower helical paths can be equal and opposite each other. In this regard, the first and second ramp surfaces 72 and 74 can be mirror images of the third and fourth ramp surfaces 76 and 78 with respect to a plane that is oriented along the lateral direction A and the transverse direction T.

Figure 8A:
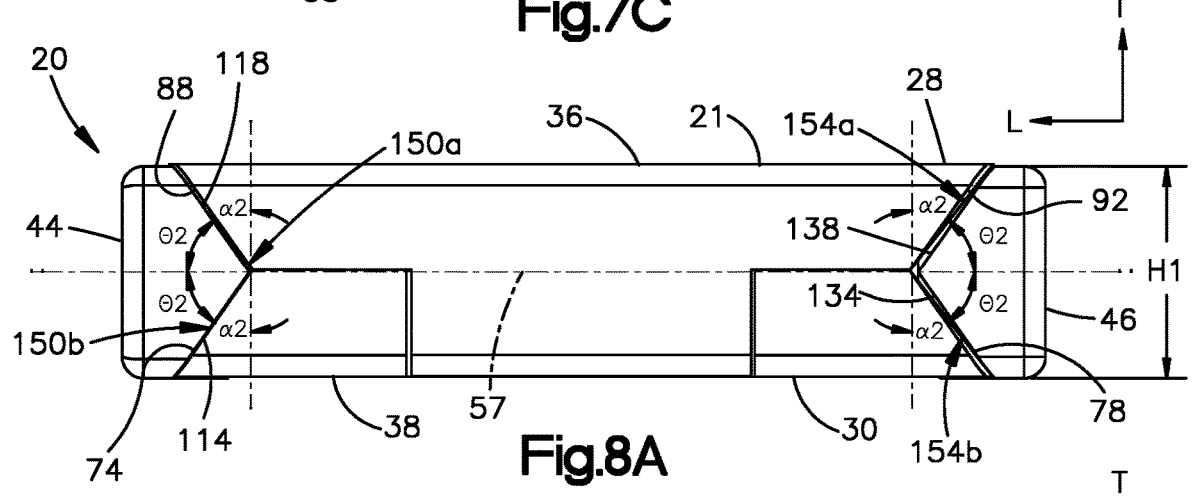
FIG. 8A is a side elevation view of a first side of the fusion cage illustrated in FIG. 7A, shown in the contracted position.
Figure 8B:
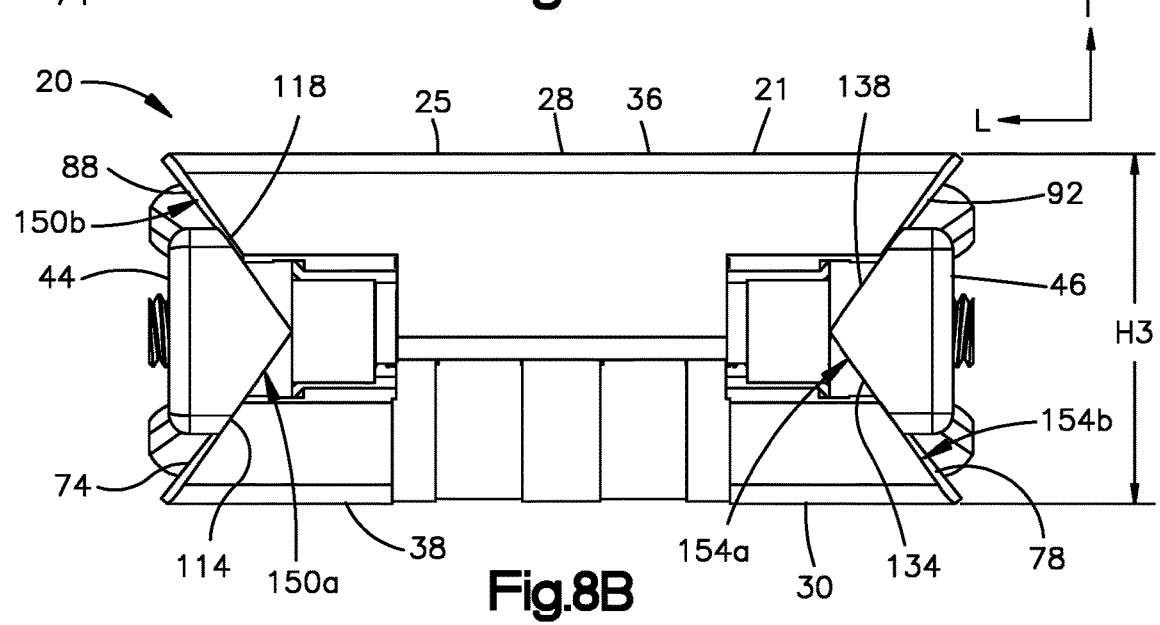
FIG. 8B is a side elevation view of the first side of the fusion cage illustrated in FIG. 8A, but shown in the expanded position.

Referring also to FIGS. 8A and 9A, the first ramp surface 72 of the lower endplate member 38 can define a first helical lead-in angle $\alpha_1$ that can be in a range from approximately 50 degrees to approximately 70 degrees, such as approximately 60 degrees with respect to the transverse direction T (or a respective plane that includes the transverse direction T and the lateral direction A). Thus, the helical lead-in angle can define a first ramp angle $\theta_1$ in a range from approximately 20 degrees to approximately 40 degrees, such as approximately 30 degrees, with respect to the longitudinal direction L (or a plane that includes the longitudinal direction L and the lateral direction A). The first ramp angle can be geometrically complementary to the first helical lead-in angle. The third ramp surface 76 of the lower endplate member 38 can also define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle of the third ramp surface 76 can define the first ramp angle $\theta_1$ in a range from approximately 20 degrees to approximately 40 degrees, such as approximately 30 degrees, with respect to the longitudinal direction L (or a plane that includes the longitudinal direction L and the lateral direction A). The first ramp angle $\theta_1$ can be geometrically complementary to the first helical lead-in angle $\alpha_1$. The first ramp angle $\theta_1$ of the third ramp surface 76 can be oriented opposite the first ramp angle $\theta_1$ of the first ramp surface 72.

The second ramp surface 74 of the lower endplate member 38 can define a second helical lead-in angle $\alpha_2$ that can be in a range from approximately 26 degrees to approximately 48 degrees, such as approximately 35 degrees with respect to a respective plane that includes the transverse direction T (or a respective plane that includes the transverse direction T and the lateral direction A). Thus, the second helical lead-in angle can define a second ramp angle $\theta_2$ in a range from approximately 42 degrees to approximately 64 degrees, such as approximately 55 degrees, with respect to the longitudinal direction L (or a plane that includes the longitudinal direction L and the lateral direction A). The second ramp angle $\theta_2$ can be geometrically complementary to the second helical lead-in angle $\alpha_2$. The fourth ramp surface 78 of the lower endplate member 38 can also define the second helical lead-in angle $\alpha_2$ that can be in the range from approximately 26 degrees to approximately 48 degrees, such as approximately 35 degrees with respect to the transverse direction T (or a respective plane that includes the transverse direction T and the lateral direction A). Thus, the second helical lead-in angle of the fourth ramp surface 78 can define the second ramp angle $\theta_2$ in the range from approximately 40 degrees to approximately 65 degrees, such as approximately 55 degrees, with respect to the longitudinal direction L (or the plane that includes the longitudinal direction L and the lateral direction A). The second ramp angle $\theta_2$ can be geometrically complementary to the second helical lead-in angle $\alpha_2$. The second ramp angle $\theta_2$ of the fourth ramp surface 78 can be oriented opposite the second ramp angle $\theta_2$ of the second ramp surface 74.

Referring again to FIGS. 2 and 3A-3B, while the first and second ramp surfaces 72 and 74 are separate ramp surfaces separated from each other along the lateral direction A in one example, it is recognized that the first and second ramp surfaces 72 and 74 can alternatively be continuous with each other so as to define a single ramp surface as desired. Similarly, while the third and fourth ramp surfaces 76 and 78 are separate ramp surfaces separated from each other along the lateral direction A in one example, it is recognized that the third and fourth ramp surfaces 76 and 78 can alternatively be continuous with each other so as to define a single ramp surface as desired.

The lower endplate member 38 can be interlinked with the first and second wedge members 44 and 46. In one example, the lower endplate member 38 can include an interlinking member that is configured to engage complementary interlinking members of the first and second wedge members 44 and 46, respectively. For instance, the interlinking member of the lower endplate member 38 can include first or proximal slots 71 disposed adjacent the first and second ramp surfaces 72 and 74, and second or distal slots 73 that are disposed adjacent the third and fourth ramp surfaces 76 and 78. The first and second slots 71 and 73 can be configured to receive the complementary interlinking members of the first and second wedge members 44 and 46, respectively. It is recognized, of course, that the interlinking member of the lower endplate member 38 can alternatively define projections that is received in a recesses of the first and second wedge members 44 and 46, respectively.

Figure 4A:
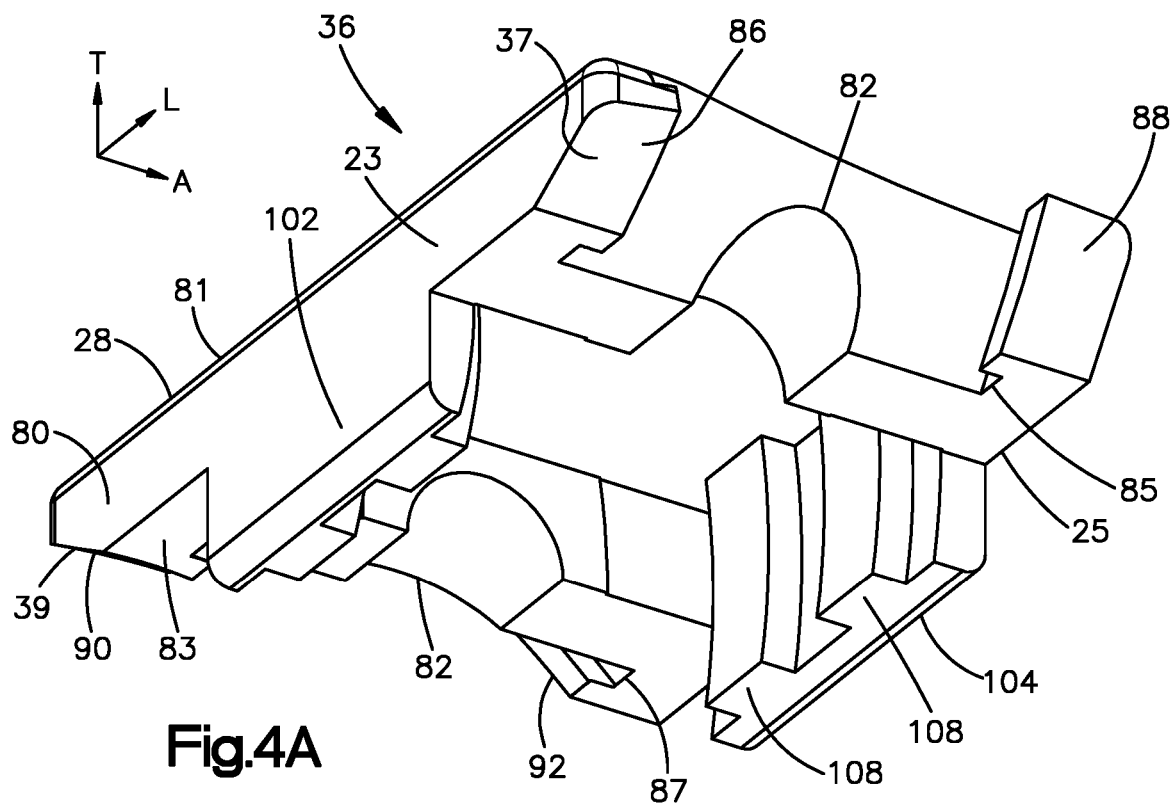
FIG. 4A is a perspective view of the upper endplate member illustrated in FIG. 2.
Figure 4B:
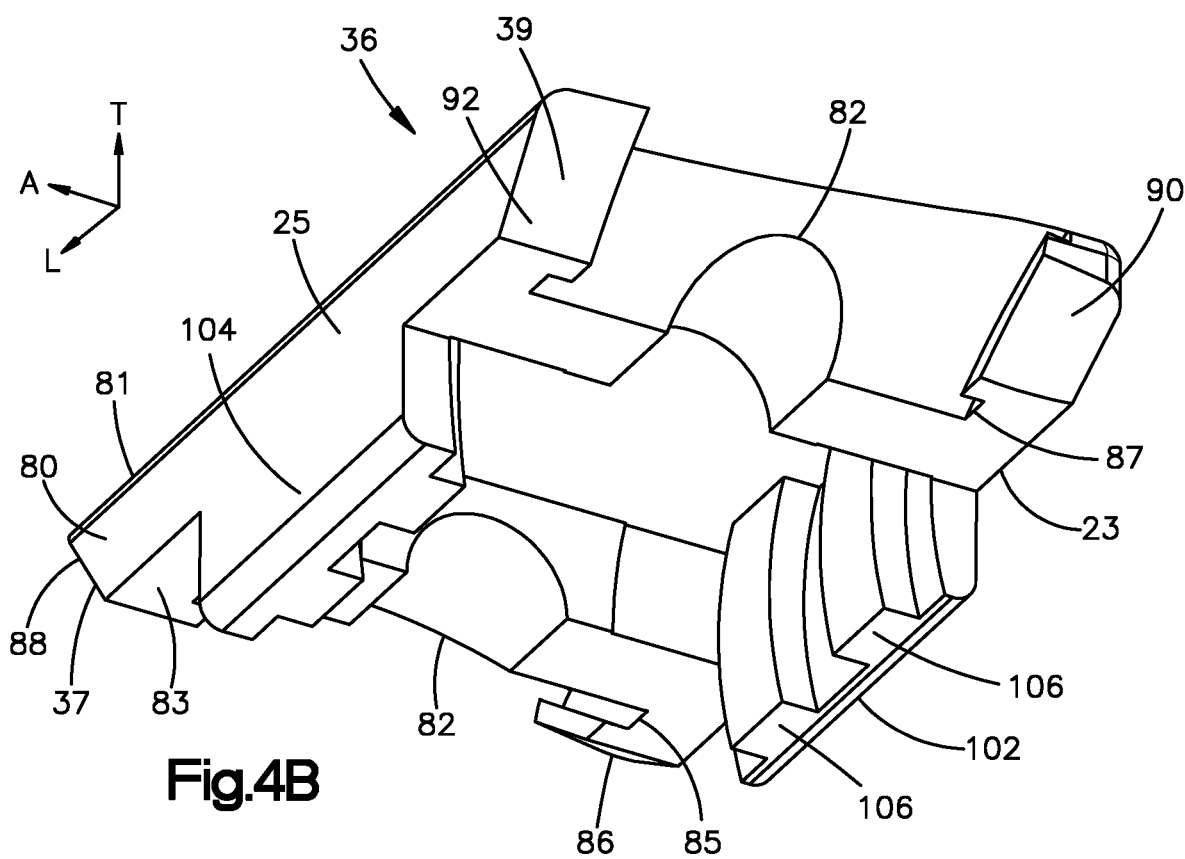
FIG. 4B is another perspective view of the upper endplate member illustrated in FIG. 3A.
Figure 7C:
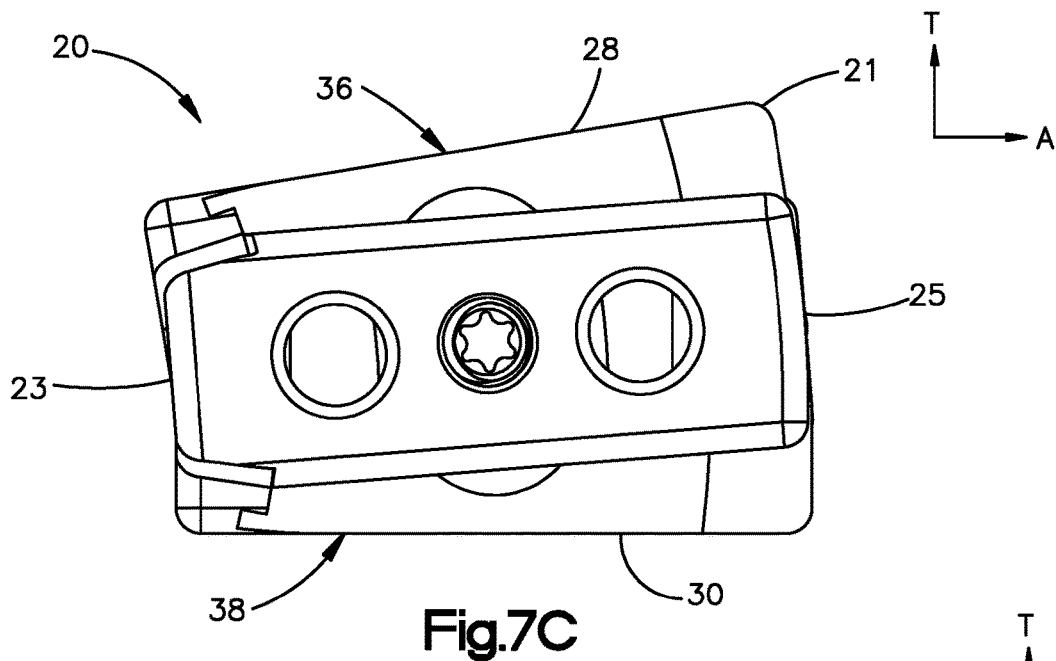
FIG. 7C is an end elevation view of the fusion cage in the expanded position as illustrated in FIG. 7B.

The upper endplate member 36 will now be described with reference to FIGS. 2 and FIGS. 4A-4B. The upper endplate member 36 can include an upper plate portion 80 having an outer surface 81 that defines the upper bone contacting surface 28, and an inner surface 83 opposite the outer surface 81. The inner surfaces 67 and 83 of the lower and upper endplates 36 and 38, respectively, can face each other along the transverse direction T. The upper endplate member 36 can further include at least one bone graft aperture 93 that extends through the upper plate portion 80 from the upper bone contacting surface 28 to the inner surface 83. The bone graft aperture 93 is configured to receive bone graft material to enhance fusion of the upper endplate member 34 with the superior vertebral body 24. The upper endplate member 36 can include recesses 82 that are configured to receive at least a portion of the actuator 48 when the fusion cage 20 is in the contracted position.

As described above, the upper endplate member 36 can include at least one first or proximal upper ramp surface 37 and the at least one second or distal upper ramp surface 39, which can each be opposite the upper bone contacting surface 28 along the longitudinal direction L. For instance, the at least one first or proximal upper ramp surface 37 and the at least one second or distal upper ramp surface 39 can be mirror images of each other. The at least one first upper ramp surface 37 can include first and second ramp surfaces 86 and 88, respectively, and the at least one second lower ramp surface 39 can include third and fourth ramp surfaces 90 and 92, respectively. The first and second ramp surfaces 86 and 88 can be referred to as first and second upper proximal ramp surfaces, respectively, of the upper endplate member 36. The third and fourth ramp surfaces 90 and 92 can be referred to as first and second upper distal ramp surfaces, respectively, of the upper endplate member 36.

The first ramp surface 86 of the upper endplate member 36 can be disposed at the first side 23 of the fusion cage 20, and the second ramp surface 88 can be disposed at the second side 25 of the fusion cage 20. The first and second ramp surfaces 86 and 88 of the upper endplate member 36 can be spaced from each other and opposite each other along the lateral direction A. The third ramp surface 90 of the upper endplate member 36 can be disposed at the first side 23 of the fusion cage, and the fourth ramp surface 92 can disposed at the second side 25 of the fusion cage. The third and fourth ramp surfaces 90 and 92 of the upper endplate member 36 can be spaced from each other and opposite each other along the lateral direction A. The first ramp surface 86 and the third ramp surface 90 can be aligned with each other along the longitudinal direction L, and the second ramp surface 88 and the fourth ramp surface 92 can be aligned with each other along the longitudinal direction L.

As described above, the fusion cage 20 can be configured to undergo lordotic expansion. Thus, the first and third ramp surfaces 86 and 90 can define the first ramp angle with respect to the longitudinal direction L (or a plane that includes the longitudinal direction L and the lateral direction A), and the second and fourth ramp surfaces 88 and 92 can define a second ramp angle with respect to the longitudinal direction L (or a plane that includes the longitudinal direction L and the lateral direction A) that is greater than the first ramp angle. The first ramp angle defined by the first and third ramp surfaces 86 and 90 can be substantially equal and opposite the first ramp angle of the first and third ramp surfaces 72 and 76 of the lower endplate member 38. The second ramp angle defined by the second and fourth ramp surfaces 88 and 92 can be substantially equal and opposite the second ramp angle of the second and fourth ramp surfaces 74 and 78 of the lower endplate member 38. As will be appreciated from the description below, the first, second, third, and fourth ramp surfaces 86-92 of the upper endplate member 36 can be in surface contact with the proximal and distal wedge members 44 and 46, respectively, as the wedge members urge the upper endplate member 36 away from the lower endplate member 38. Further, the first, second, third and fourth ramp surfaces 86-92 are included in the same unitary singular upper endplate member 36, and can be constructed so as to not rotate with respect to each other during movement of the cage body 21 from the contracted position toward the expanded position. Thus, the first, second, third and fourth ramp surfaces 86-92 can be said to be rotatably fixed with respect to each other. Thus, the first and second ramp angles can be referred to as fixed ramp angles, respectively.

Advantageously, the first and second wedge members 44 and 46, respectively, can be configured to maintain surface contact with each of the ramp surfaces 86-82 of the upper endplate member 36 as the fusion cage 20 iterates between the contracted position and the expanded position. Accordingly, each of the first and second ramp surfaces 86 and 88 of the upper endplate member 36 and the third and fourth ramp surfaces 90 and 92 of the upper endplate member 36 can extend along respective nonplanar paths. In one example, the first and second ramp surfaces 86 and 88 of the upper endplate member 36 and the third and fourth ramp surfaces 90 and 92 of the upper endplate member 36 can extend along respective twisted paths. For instance, the first and second ramp surfaces 86 and 88 of the upper endplate member 36 can extend along respective helical paths. The helical paths of the first and second ramp surfaces 86 and 88 can be defined by a common helical pitch, but defined by different helical radii. For instance, the helical paths of the first and second ramp surfaces 86 and 88 can be defined by a single swept helix. Similarly, the third and fourth ramp surfaces 90 and 92 of the upper endplate member 36 can extend along respective helical paths. The helical paths of the third and fourth ramp surfaces 90 and 92 can be defined by a common helical pitch, but defined by different helical radii. For instance, the helical paths of the third and fourth ramp surfaces 90 and 92 can be defined by a single swept helix. The first and second upper helical paths can be concave in one example.

In one example, the first and second ramp surfaces 86 and 88 extend along a respective first single upper helical path that is continuous from the first ramp surface 86 to the second ramp surface 88. Similarly, the third and fourth ramp surfaces 90 and 92 can extend along a second single upper helical path that is continuous from the third ramp surface 90 to the fourth ramp surface 92. The first and second upper helical paths can be equal and opposite each other. In this regard, the first and second ramp surfaces 86 and 88 can be mirror images of the third and fourth ramp surfaces 90 and 92 with respect to a plane that is oriented along the lateral direction A and the transverse direction T. Further, the first single upper helical path can be a mirror image of the first single lower helical path of the lower endplate member 38. Similarly, the second single upper helical path can be a mirror image of the second single lower helical path of the lower endplate member 38.

Referring also to FIGS. 8A and 9A, the first ramp surface 86 of the upper endplate member 36 can define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle $\alpha_1$ of the first ramp surface 86 can define the first ramp angle $\theta_1$ in a range from approximately 20 degrees to approximately 40 degrees, such as approximately 30 degrees, with respect to the longitudinal direction L (or a plane that includes the longitudinal direction L and the lateral direction A). The first ramp angle $\theta_1$ of the first ramp surface 86 can be geometrically complementary to the first helical lead-in angle $\alpha_1$ of the first ramp surface 86. The third ramp surface 90 of the upper endplate member 36 can also define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle $\alpha_1$ of the third ramp surface 90 can define the first ramp angle $\theta_1$ in the range from approximately 20 degrees to approximately 40 degrees, such as approximately 30 degrees, with respect to the longitudinal direction L (or the plane that includes the longitudinal direction L and the lateral direction A). The first ramp angle $\theta_1$ of the third ramp surface 90 can be geometrically complementary to the first helical lead-in angle $\alpha_1$ of the third ramp surface 90. The first ramp angle $\theta_1$ of the third ramp surface 90 can be oriented opposite the first ramp angle $\theta_1$ of the first ramp surface 86. Further, the first ramp angle $\theta_1$ of the first ramp surface 86 can be oriented opposite the first ramp angle $\theta_1$ of the first ramp surface 72 of the lower endplate member 38 (see FIG. 9A). Further still, the first ramp surface 86 can be oriented parallel with the third ramp surface 76 of the lower endplate member 38 (see FIG. 9A).

The second ramp surface 88 of the upper endplate member 36 can define the second helical lead-in angle $\alpha_2$ that can be in a range from approximately 26 degrees to approximately 48 degrees, such as approximately 35 degrees with respect to the transverse direction T (or a respective plane that includes the transverse direction T and the lateral direction A). Thus, the second helical lead-in angle $\alpha_2$ of the second ramp surface 88 can define a second ramp angle $\theta_2$ in a range from approximately 42 degrees to approximately 64 degrees, such as approximately 55 degrees, with respect to the longitudinal direction L (or a plane that includes the longitudinal direction L and the lateral direction A). The second ramp angle $\theta_2$ of the second ramp surface 88 can be geometrically complementary to the second helical lead-in angle $\alpha_2$ of the second ramp surface 88. The fourth ramp surface 92 of the upper endplate member 36 can also define the second helical lead-in angle $\alpha_2$ that can be in the range from approximately 26 degrees to approximately 48 degrees, such as approximately 35 degrees with respect to the transverse direction T (or a respective plane that includes the transverse direction T and the lateral direction A). Thus, the second helical lead-in angle $\alpha_2$ of the fourth ramp surface 92 can define the second ramp angle $\theta_2$ in the range from approximately 42 degrees to approximately 64 degrees, such as approximately 55 degrees, with respect to the longitudinal direction L (or the plane that includes the longitudinal direction L and the lateral direction A). The second ramp angle $\theta_2$ of the fourth ramp surface 92 can be geometrically complementary to the second helical lead-in angle $\alpha_2$ of the fourth ramp surface 92. The second ramp angle $\theta_2$ of the fourth ramp surface 92 can be oriented opposite the second ramp angle $\theta_2$ of the second ramp surface 88. Further, the second ramp angle $\theta_2$ of the second ramp surface 88 can be oriented opposite the second ramp angle of the second ramp surface 74 of the lower endplate member 38 (see FIG. 8A). Further still, the second ramp surface 88 can be oriented substantially parallel with the fourth ramp surface 78 of the lower endplate member 38 (see FIG. 8A).

Referring again to FIGS. 2 and 4A-4B, while the first and second ramp surfaces 86 and 88 are separate ramp surfaces separated from each other along the lateral direction A in one example, it is recognized that the first and second ramp surfaces 86 and 88 can alternatively be continuous with each other so as to define a single ramp surface as desired. Similarly, while the third and fourth ramp surfaces 90 and 92 are separate ramp surfaces separated from each other along the lateral direction A in one example, it is recognized that the third and fourth ramp surfaces 90 and 92 can alternatively be continuous with each other so as to define a single ramp surface as desired.

The upper endplate member 36 can be interlinked with the first and second wedge members 44 and 46. In one example, the upper endplate member 36 can include an interlinking member that is configured to engage complementary interlinking members of the first and second wedge members 44 and 46, respectively. For instance, the interlinking member of the upper endplate member 36 can include first or proximal slots 85 disposed adjacent the first and second ramp surfaces 86 and 88, and second or distal slots 87 that are disposed adjacent the third and fourth ramp surfaces 90 and 92. The first and second slots 85 and 87 can be configured to receive the complementary interlinking members of the first and second wedge members 44 and 46, respectively. It is recognized, of course, that the interlinking member of the upper endplate member 36 can alternatively define projections that is received in a recesses of the first and second wedge members 44 and 46, respectively.

Referring now to FIGS. 2-4B, the upper and lower endplate members 36 and 38 can include respective alignment members that engage each other and guide movement of the fusion cage 20 between the contracted position and the expanded position, thereby enhancing the stability and structural integrity of the fusion cage 20. For instance, the lower endplate member 38 can include first and second lower side walls 94 and 96 that extend, for instance up, from the lower plate portion 64. The first and second side walls 94 and 96 are spaced from each other and opposite each other along the lateral direction A. In particular, the first side wall 94 can be disposed at the first side 23 of the fusion cage 20, and the second side wall 96 can be disposed at the second side 25 of the fusion cage 20. The alignment member of the lower endplate member 38 can be supported by the first and second side walls 94 and 96.

For instance, the alignment member of the lower endplate member 38 can include a first at least one lower rib 98 that extends out from an outer surface of the first side wall 94 along a direction away from the central axis 57, and a second at least one lower rib 100 that extends out from an outer surface of the second side wall 96 along a direction away from the central axis 57. The outer surface of the first side wall 94, and thus the first at least one lower rib 98, can define a curvature, such as concave curvature, as it extends along the transverse direction T. The outer surface of the second side wall 96, and thus the second at least one lower rib 100, can define a curvature, such as a convex curvature, as it extends along the transverse direction T.

Similarly, the upper endplate member 36 can include first and second upper side walls 102 and 104 that extend, for instance down, from the upper plate portion 80. The first and second side walls 102 and 104 are spaced from each other and opposite each other along the lateral direction A. In particular, the first side wall 102 can be disposed at the first side 23 of the fusion cage 20, and the second side wall 104 can be disposed at the second side 25 of the fusion cage 20. The alignment member of the upper endplate member 36 can be supported by the first and second side walls 102 and 104.

For instance, the alignment member of the upper endplate member 36 can include a first at least one upper rib 106 that extends out from an inner surface of the first side wall 102 along a direction toward from the central axis 57, and a second at least one upper rib 108 that extends out from an inner surface of the second side wall 104 along a direction toward from the central axis 57. The inner surface of the first side wall 102, and thus the first at least one upper rib 106, can have a curvature, such as a convex curvature, as it extends along the transverse direction T. The inner surface of the second side wall 104, and thus the second at least one upper rib 108, can have a curvature, such as concave curvature, as it extends along the transverse direction T.

In one example, each of the at least one lower ribs and the at least one upper ribs can include a plurality of ribs and slots therebetween, such that the ribs can engage each other in the respective slots when engaged in a sliding relationship that allows for expansion and contraction of the fusion cage 20. For instance, the first at least one lower rib 98 can engage the first at least one upper rib 106, and in particular can be disposed in a slot defined between a pair of adjacent first upper ribs 106. Conversely, the first at least one upper rib 106 can engage the first at least one lower rib 98, and in particular can be disposed in a slot defined between a pair of adjacent first lower ribs 98. Similarly, the second at least one lower rib 100 can engage the second at least one upper rib 108, and in particular can be disposed in a slot defined between a pair of adjacent second upper ribs 108. Conversely, the second at least one upper rib 108 can engage the second at least one lower rib 100, and in particular can be disposed in a slot defined between a pair of adjacent second lower ribs 100. The curvatures of the side walls of the upper and lower endplate members 36 and 38 and corresponding ribs allows the alignment members to remain engaged with each other during expansion of the fusion cage 20, during which the second side 25 of the fusion cage 20 expands at a greater rate than the first side 23 of the fusion cage 20. Thus, the alignment members of the upper and lower endplates 36 and 38 can guide relative movement of the upper and lower endplate members 36 and 38 as the fusion cage 20 iterates between the contracted position and the expanded position. The engagement of the ribs can prevent the first and second endplate members 36 and 38 from translating along the lateral and longitudinal directions during expansion or contraction of the fusion cage 20.

The lower ribs 98 and 100 and the upper ribs 106 and 108 can define any suitable shape as desired. For instance, in one example, the lower ribs 98 and 100 and the upper ribs 106 and 108 can be rectangular in cross section along a plane that is defined by the longitudinal direction L and the lateral direction A. Alternatively, the lower ribs 98 and 100 and the upper ribs 106 and 108 can define interlocking dovetail shapes.

The first and second wedge members 44 and 46 will now be described with reference to FIGS. 2 and 5A-6C. In particular, with initial reference to FIGS. 2 and FIGS. 5A-5C, the first or proximal wedge member 44 defines a first wedge body 110. The first wedge member 44 defines a first bore 111 that extends at least into or through the first wedge body 110 along the longitudinal direction L. The first wedge member 44 can define a first ferrule that extends from the first wedge body 110 in the distal direction, and can define a distalmost surface of the first wedge member 44. The bore 111 can extend proximally through the first ferrule to the proximal surface of the first wedge body 110, which can also define a proximal-most surface of the first wedge member 44.

At least a portion of the bore 111 can be internally threaded and thus configured to threadedly mate with the first threaded portion 53 of the first section 52 of the actuator shaft 50, and thus of the actuator 48. Accordingly, rotation of the actuator 48 in the first direction of rotation causes the first wedge member 44 to translate along the actuator shaft 50, and thus the actuator 48, distally toward the second wedge member 46 in the expansion direction. Rotation of the actuator 48 in the second direction of rotation causes the first wedge member 44 to translate along the actuator shaft 50, and thus the actuator 48, proximally away from the second wedge member 46 in the contraction direction.

The bore 111 can extend through the first wedge body 110, such that the bore 111 is open to the proximal surface of the first wedge member 44. Accordingly, an instrument can access a proximal end 59 (see FIG. 11A) of the actuator 48 through the bore 111, or the actuator 48 can extend proximally through the bore 111. The proximal end 59 of the actuator 48 can include any internal or external geometry that is configured to be engaged by the instrument, such that the instrument and the actuator 48 are rotatably coupled to each other. As a result, rotation of the instrument in the first direction of rotation causes the actuator 48 to correspondingly rotate relative to the cage body 21 in the first direction of rotation. Similarly, rotation of the instrument in the second direction of rotation causes the actuator 48 to rotate relative to the cage body 21 in the second direction of rotation.

It is further recognized that imparting a rotational force to the actuator 48 can similarly impart a rotational force to the cage body 21. As a result, the cage body 21 can include at least one anti-rotation member 120 that is configured to engage an instrument to prevent rotation of the cage body 21 during rotation of the actuator 48. In one example, the anti-rotation member 120 can be configured as anti-rotation apertures 121 that extend distally into the proximal surface of the first wedge member 44. The anti-rotation apertures 121 can be disposed on respective opposite sides of the bore 111. During use, an instrument can include projections that extend into the anti-rotation apertures 121 to prevent rotation of the cage body 21 during rotation of the actuator 48. In one example, the anti-rotation apertures 121 can also be configured to receive bone graft material. In this regard, the anti-rotation apertures 121 can define bone graft channels. Thus, after the fusion cage 20 has reached the expanded position, bone graft injected through the bone graft channels can travel to the interior of the cage body 21, and through the bone graft apertures of the upper and lower endplates 36 and 38 (see FIG. 2) to enhance fusion of the bone cage 20 with the superior and inferior vertebral bodies. It should be appreciated that the bone graft channels can be alternatively positioned as desired.

With continuing reference to FIGS. 2 and 5A-5C, and as described above, the first wedge body 110 defines the at least one upper ramp surface 45 and at least one lower ramp surface 47 opposite the at least one upper ramp surface 45 along the transverse direction T. The at least one upper ramp surface 45 can be sloped inferiorly toward the lower bone contacting surface 30 as it extends along the distal direction toward the second wedge member 46. The at least one lower ramp surface 47 can be sloped superiorly toward the upper bone contacting surface 30 as it extends along the distal direction toward the second wedge member 46.

The at least one lower ramp surface 47 of the first or proximal wedge member 44 can include first and second ramp surfaces 112 and 114. The at least one upper ramp surface 45 of the first or proximal wedge member 44 can include third and fourth ramp surfaces 116 and 118, respectively. The first and second ramp surfaces 112 and 114 can be referred to as first and second lower proximal ramp surfaces, respectively, of the first wedge member 44. The third and fourth ramp surfaces 116 and 118 can be referred to as first and second upper proximal ramp surfaces, respectively, of the first wedge member 44.

The first ramp surface 112 of the first wedge member 44 can be disposed at the first side 23 of the fusion cage 20, and the second ramp surface 114 can be disposed at the second side 25 of the fusion cage 20. The first and second ramp surfaces 112 and 114 of the first wedge member 44 can be spaced from each other and opposite each other along the lateral direction A. The third ramp surface 116 of the first wedge member 44 can be disposed at the first side 23 of the fusion cage, and the fourth ramp surface 118 can disposed at the second side 25 of the fusion cage. The third and fourth ramp surfaces 116 and 118 of the first wedge member 44 can be spaced from each other and opposite each other along the lateral direction A. The first ramp surface 112 and the third ramp surface 116 can be aligned with each other along the transverse direction T, and the second ramp surface 114 and the fourth ramp surface 118 can be aligned with each other along the transverse direction T.

As described above, the fusion cage 20 can be configured to undergo lordotic expansion. Thus, the first and third ramp surfaces 112 and 116 can define the first ramp angle with respect to the longitudinal direction L (or a plane that includes the longitudinal direction L and the lateral direction A), and the second and fourth ramp surfaces 114 and 118 can define the second ramp angle with respect to the longitudinal direction L (or a plane that includes the longitudinal direction L and the lateral direction A) that is greater than the first ramp angle.

It should thus be appreciated that the first ramp surface 112 of the first wedge member 44 is sloped substantially equal to the first ramp surface 72 of the lower endplate member 38. Further, the second ramp surface 114 of the first wedge member 44 is sloped substantially equal to the second ramp surface 74 of the lower endplate member 38. Similarly, the third ramp surface 116 of the first wedge member 44 is sloped substantially equal to the first ramp surface 86 of the upper endplate member 36. Further, the fourth ramp surface 118 of the first wedge member 44 is sloped substantially equal to the second ramp surface 88 of the upper endplate member 36.

As described above, the fusion cage 20 can undergo lordotic expansion as it iterates from the contracted position to the expanded position. Advantageously, the first ramp surface 112 of the first wedge member 44 can maintain surface contact with the first ramp surface 72 of the lower endplate member 38 as the fusion cage 20 iterates between the contracted position and the expanded position. Further, the second ramp surface 114 of the first wedge member 44 can maintain surface contact with the second ramp surface 74 of the lower endplate member 38 as the fusion cage 20 iterates between the contracted position and the expanded position. Similarly, the third ramp surface 116 of the first wedge member 44 can maintain surface contact with the first ramp surface 86 of the upper endplate member 36 as the fusion cage 20 iterates between the contracted position and the expanded position. Further, the fourth ramp surface 118 of the first wedge member 44 can maintain surface contact with the second ramp surface 88 of the upper endplate member 36 as the fusion cage 20 iterates between the contracted position and the expanded position. The first, second, third and fourth ramp surfaces 112-118 are included in the same unitary singular first wedge member 44, and can be constructed so as to not rotate with respect to each other during movement of the first wedge member 44 in the expansion direction. Thus, the first, second, third and fourth ramp surfaces 112-118 can be said to be rotatably fixed with respect to each other. The first and second ramp angles can therefore be referred to as fixed ramp angles, respectively.

In this regard, the first and second ramp surfaces 112 and 114 of the first wedge member 44 can extend along respective helical wedge paths of the first wedge member 44. The helical wedge paths of the first and second ramp surfaces 112 and 114 of the first wedge member can be defined by a common helical pitch, but defined by different helical radii. For instance, the helical wedge paths of the first and second ramp surfaces 112 and 114 can be defined by a single swept helix. The helical wedge paths of the first and second ramp surfaces 112 and 114 can be complementary to the common respective helical paths of the first and second ramp surfaces 72 and 74 of the lower endplate member 38. Thus, the helical wedge paths of the first and second ramp surfaces 112 and 114 of the first wedge member 44 can define convex helical paths. As a result, the first and second ramp surfaces 112 and 114 of the first wedge member 44 can maintain surface contact with the respective first and second ramp surfaces 72 and 74 of the lower endplate member 38 as the fusion cage 20 iterates between the contracted position and the expanded position. In one example, the first and second ramp surfaces 112 and 114 of the first wedge member 44 can maintain surface contact with the respective first and second ramp surfaces 72 and 74 of the lower endplate member 38 throughout the entire range of motion between the contracted position and the expanded position.

Similarly, the third and fourth ramp surfaces 116 and 118 of the first wedge member 44 can extend along respective helical wedge paths of the first wedge member 44. The helical wedge paths of the third and fourth ramp surfaces 116 and 118 of the first wedge member 44 can be defined by a common helical pitch, but defined by different helical radii. For instance, the helical wedge paths of the third and fourth ramp surfaces 116 and 118 can be defined by a single swept helix. The helical wedge paths of the third and fourth ramp surfaces 116 and 118 can be complementary to the respective helical paths of the first and second ramp surfaces 86 and 88 of the upper endplate member 36. Thus, the helical wedge path of the third and fourth ramp surfaces 116 and 118 of the first wedge member 44 can define respective convex helical paths. As a result, the third and fourth ramp surfaces 116 and 118 of the first wedge member 44 can maintain surface contact with the respective first and second ramp surfaces 86 and 88 of the upper endplate member 36 as the fusion cage 20 iterates between the contracted position and the expanded position. In one example, the third and fourth ramp surfaces 116 and 118 of the first wedge member 44 can maintain surface contact with the respective first and second ramp surfaces 86 and 88, respectively, of the upper endplate member 36 throughout the entire range of motion between the contracted position and the expanded position.

Referring also to FIGS. 8A and 9A, the first ramp surface 112 of the first wedge member 44 can define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle $\alpha_1$ of the first ramp surface 112 can define the first ramp angle $\theta_1$ in a range from approximately 20 degrees to approximately 40 degrees, such as approximately 30 degrees, with respect to the longitudinal direction L (or a plane that includes the longitudinal direction L and the lateral direction A). The first ramp angle $\theta_1$ of the first ramp surface 112 can be geometrically complementary to the first helical lead-in angle $\alpha_1$ of the first ramp surface 112. The third ramp surface 116 of the first wedge member 44 can also define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle $\alpha_1$ of the third ramp surface 116 can define the first ramp angle $\theta_1$ in the range from approximately 20 degrees to approximately 40 degrees, such as approximately 30 degrees, with respect to the longitudinal direction L (or a plane that includes the longitudinal direction L and the lateral direction A). The first ramp angle $\theta_1$ of the third ramp surface 116 can be geometrically complementary to the first helical lead-in angle $\alpha_1$ of the third ramp surface 116. The first ramp angle $\theta_1$ of the third ramp surface 116 can be oriented opposite the first ramp angle $\theta_1$ of the first ramp surface 112 (see FIG. 9A). Further, the first ramp surface 112 can be oriented parallel with the first ramp surface 72 of the lower endplate member 38 (see FIG. 9A).

The second ramp surface 114 of the first wedge member 44 can define the second helical lead-in angle $\alpha_2$ that can be in a range from approximately 26 degrees to approximately 48 degrees, such as approximately 35 degrees with respect to the transverse direction T (or a respective plane that includes the transverse direction T and the lateral direction A). Thus, the second helical lead-in angle $\alpha_2$ of the second ramp surface 114 can define a second ramp angle $\theta_2$ in a range from approximately 42 degrees to approximately 64 degrees, such as approximately 55 degrees, with respect to the longitudinal direction L (or a plane that includes the longitudinal direction L and the lateral direction A). The second ramp angle $\theta_2$ of the second ramp surface 114 can be geometrically complementary to the second helical lead-in angle $\alpha_2$ of the second ramp surface 114. The fourth ramp surface 118 of the first wedge member 44 can also define the second helical lead-in angle $\alpha_2$ that can be in the range from approximately 26 degrees to approximately 48 degrees, such as approximately 35 degrees with respect to the transverse direction T (or a respective plane that includes the transverse direction T and the lateral direction A). Thus, the second helical lead-in angle $\alpha_2$ of the fourth ramp surface 118 can define the second ramp angle $\theta_2$ in the range from approximately 42 degrees to approximately 64 degrees, such as approximately 55 degrees, with respect to the longitudinal direction L (or the plane that includes the longitudinal direction L and the lateral direction A). The second ramp angle $\theta_2$ of the fourth ramp surface 118 can be geometrically complementary to the second helical lead-in angle $\alpha_2$ of the fourth ramp surface 118. The second ramp angle $\theta_2$ of the fourth ramp surface 118 can be oriented opposite the second helical lead-in angle $\alpha_2$ of the second ramp surface 114. Further, the fourth ramp surface 118 can be oriented parallel with the second ramp surface 88 of the upper endplate member 36 (see FIG. 8A). Further still, the second ramp angle θ₂ of the fourth ramp surface 118 can be oriented opposite the second ramp angle θ₂ of the fourth ramp surface 92 of the upper endplate member 36 (see FIG. 8A).

As described above, the first wedge member 44 can be interlinked with each of the upper and lower endplate members 36 and 38. Referring again to FIGS. 2 and 5A-5C, the first wedge member 44 can include at least one protrusion that is captured by the upper endplate member 36, and at least one protrusion that is captured by the lower endplate member 38. In particular, the first wedge member 44 can include a first protrusion 122 that extends out from the first wedge body 110 along the lateral direction A. The first protrusion 122 can be spaced below the first ramp surface 112, and aligned with at least a portion of the first ramp surface 112 along the transverse direction T, such that the first wedge member 44 defines a first gap that extends between the first protrusion 122 and the first ramp surface 112. The first wedge member 44 can further include a second protrusion 124 that extends out from the first wedge body 110 along the lateral direction A. The second protrusion 124 can extend out from the first wedge body 110 a direction opposite the first protrusion 122. The second protrusion 124 can be spaced below the second ramp surface 114, and aligned with at least a portion of the second ramp surface 114 along the transverse direction T, such that the first wedge member 44 defines a second gap that extends between the second protrusion 124 and the second ramp surface 114. The first and second protrusions 122 and 124 can be referred to as lower protrusions of the first wedge member 44, or a lower pair of protrusions of the first wedge member 44. While the first and second protrusions 122 and 124 are illustrated as protrusions separate from each other along the lateral direction A, it should be appreciated that the first and second protrusions can alternatively be continuous with each other to define a single unitary protrusion.

Similarly, the first wedge member 44 can include a third protrusion 126 that extends out from the first wedge body 110 along the lateral direction A. The third protrusion 126 can be spaced above the third ramp surface 116, and aligned with at least a portion of the third ramp surface 116 along the transverse direction T, such that the first wedge member 44 defines a third gap that extends between the third protrusion 126 and the third ramp surface 116. The first wedge member 44 can include a fourth protrusion 128 that extends out from the first wedge body 110 along the lateral direction A. The fourth protrusion 128 can be spaced above the fourth ramp surface 118, and aligned with at least a portion of the fourth ramp surface 118 along the transverse direction T, such that the first wedge member 44 defines a fourth gap that extends between the fourth protrusion 128 and the fourth ramp surface 118. The third and fourth protrusions 126 and 128 can be referred to as upper protrusions of the first wedge member 44, or an upper pair of protrusions of the first wedge member 44. While the third and fourth protrusions 126 and 128 are illustrated as protrusions separate from each other along the lateral direction A, it should be appreciated that the third and fourth protrusions 126 and 128 can alternatively be continuous with each other to define a single unitary protrusion.

The first wedge member 44 can interlink with the upper and lower endplates 36 and 38, respectively. In particular, the first and second protrusions 122 and 124 can be disposed in respective ones of the first slots 71 of the lower endplate member 38 (see FIGS. 3A-3B). Similarly, the third and fourth protrusions 126 and 128 can be disposed in respective ones of the first slots 85 of the upper endplate member 36 (see FIGS. 4A-4B). Accordingly, the first wedge member 44 can be captured by each of the upper and lower endplate members 36 and 38. Further, as the first wedge member 44 is moved in the contraction direction, the first and second protrusions 122 and 124 can ride along respective ramped inner surfaces of the lower endplate member 38 opposite the first and second ramp surfaces 72 and 74 (see FIGS. 3A-3B), which can urge the lower endplate member 38 toward the upper endplate member 36 along the transverse direction T. Similarly, as the first wedge member 44 is moved in the contraction direction, the third and fourth protrusions 126 and 128 can ride along respective ramped inner surfaces of the upper endplate member 36 opposite the first and second ramp surfaces 86 and 88 (see FIGS. 4A-4B), which can urge the upper endplate member 36 toward the lower endplate member 38 along the transverse direction T. Thus, both the height and lordotic curvature of the cage 20 can be reduced. Alternatively or additionally, movement of the first wedge member 44 in the contraction direction allows anatomical or other forces to cause the upper and lower endplate members 36 and 38 to move toward each other.

The second or distal wedge member 46 will now be described with reference to FIG. 2 and FIGS. 6A-6C. In particular, the second wedge member 46 defines a second wedge body 130. The second wedge member 46 defines a second bore 113 that extends at least into or through the second wedge body 130 along the longitudinal direction L. The second wedge member 46 can define a second ferrule that extends from the second wedge body 130 in the proximal direction, and can define a proximal-most surface of the second wedge member 46. The bore 113 can extend distally through the second ferrule toward or to a distal surface of the second wedge body 130 that can also define the distal surface of the second wedge member 46. The bore 113 can extends through the second ferrule.

At least a portion of the bore 113 can be internally threaded and thus configured to threadedly mate with the second threaded portion 55 of the second section 54 of the actuator shaft 50, and thus of the actuator 48. Accordingly, rotation of the actuator 48 in the first direction of rotation causes the second wedge member 46 to translate along the actuator shaft 50, and thus the actuator 48, proximally toward the first wedge member 44 in the expansion direction. Rotation of the actuator 48 in the second direction of rotation causes the second wedge member 46 to translate along the actuator shaft 50, and thus the actuator 48, proximally away from the first wedge member 44 in the contraction direction. While the first and second wedge members 44 and 46 can be threadedly coupled to the actuator 48, it is recognized that they wedge members 44 and 46 can be coupled to the actuator 48 in accordance with any suitable alternative embodiment that can allow or cause the wedge members 44 and 46 to move in the expansion direction, and in some examples also selectively in the contraction direction.

The second wedge body 130, and thus the second wedge member 46, defines the at least one upper ramp surface 49 and the at least one lower ramp surface 51 opposite the at least one upper ramp surface 49 along the transverse direction T. The at least one upper ramp surface 49 can be sloped inferiorly toward the lower bone contacting surface 30 as it extends in the proximal direction toward the first wedge member 44. The at least one lower ramp surface 51 can be sloped superiorly toward the upper bone contacting surface 28 as it extends in the proximal direction toward the first wedge member 44.

The at least one lower ramp surface 51 of the second or distal wedge member 46 can include first and second ramp surfaces 132 and 134. The at least one upper ramp surface 49 of the second or distal wedge member 46 can include third and fourth ramp surfaces 136 and 138, respectively. The first and second ramp surfaces 132 and 134 can be referred to as first and second lower proximal ramp surfaces, respectively, of the second wedge member 46. The third and fourth ramp surfaces 136 and 138 can be referred to as first and second upper proximal ramp surfaces, respectively, of the second wedge member 46.

The first ramp surface 132 of the second wedge member 46 can be disposed at the first side 23 of the fusion cage 20, and the second ramp surface 134 can be disposed at the second side 25 of the fusion cage 20. The first and second ramp surfaces 132 and 134 of the second wedge member 46 can be spaced from each other and opposite each other along the lateral direction A. The third ramp surface 136 of the second wedge member 46 can be disposed at the first side 23 of the fusion cage, and the fourth ramp surface 138 can disposed at the second side 25 of the fusion cage. The third and fourth ramp surfaces 136 and 138 of the second wedge member 46 can be spaced from each other and opposite each other along the lateral direction A. The first ramp surface 132 and the third ramp surface 136 can be aligned with each other along the transverse direction T, and the second ramp surface 134 and the fourth ramp surface 138 can be aligned with each other along the transverse direction T.

As described above, the fusion cage 20 can be configured to undergo lordotic expansion. Thus, the first and third ramp surfaces 132 and 136 can define the first ramp angle with respect to the longitudinal direction L (or a plane that includes the longitudinal direction L and the lateral direction A), and the second and fourth ramp surfaces 134 and 138 can define the second ramp angle with respect to the longitudinal direction L (or a plane that includes the longitudinal direction L and the lateral direction A) that is greater than the first ramp angle.

It should thus be appreciated that the first ramp surface 132 of the second wedge member 46 is sloped substantially equal to the third ramp surface 76 of the lower endplate member 38. Further, the second ramp surface 134 of the second wedge member 46 is sloped substantially equal to the fourth ramp surface 78 of the lower endplate member 38. Similarly, the third ramp surface 136 of the second wedge member 46 is sloped substantially equal to the third ramp surface 90 of the upper endplate member 36. Further, the fourth ramp surface 138 of the second wedge member 46 is sloped substantially equal to the fourth ramp surface 92 of the upper endplate member 36.

As described above, the fusion cage 20 can undergo lordotic expansion as it iterates from the contracted position to the expanded position. Advantageously, the first ramp surface 132 of the second wedge member 46 can maintain surface contact with the third ramp surface 76 of the lower endplate member 38 as the fusion cage 20 iterates between the contracted position and the expanded position. Further, the second ramp surface 134 of the second wedge member 46 can maintain surface contact with the fourth ramp surface 78 of the lower endplate member 38 as the fusion cage 20 iterates between the contracted position and the expanded position. Similarly, the third ramp surface 136 of the second wedge member 46 can maintain surface contact with the third ramp surface 90 of the upper endplate member 36 as the fusion cage 20 iterates between the contracted position and the expanded position. Further, the fourth ramp surface 138 of the second wedge member 46 can maintain surface contact with the fourth ramp surface 92 of the upper endplate member 36 as the fusion cage 20 iterates between the contracted position and the expanded position. The first, second, third and fourth ramp surfaces 132-138 are included in the same unitary singular second wedge member 46, and can be constructed so as to not rotate with respect to each other during movement of the second wedge member 46 in the expansion direction. Thus, the first, second, third and fourth ramp surfaces 132-138 can be said to be rotatably fixed with respect to each other. The first and second ramp angles can therefore be referred to as fixed ramp angles, respectively.

In this regard, the first and second ramp surfaces 132 and 134 of the second wedge member 46 can extend along respective helical wedge paths of the second wedge member 46. The helical wedge paths of the first and second ramp surfaces 132 and 134 of the second wedge member 46 can be defined by a common helical pitch, but defined by different helical radii. For instance, the helical wedge paths of the first and second ramp surfaces 132 and 134 can be defined by a single swept helix. The helical wedge paths of the first and second ramp surfaces 132 and 134 of the second wedge member 46 can be complementary to the helical paths of the third and fourth ramp surfaces 76 and 78 of the lower endplate member 38. Thus, the helical wedge paths of the first and second ramp surfaces 132 and 134 of the second wedge member 46 can therefore define a convex helical path that is complementary to the concave helical paths of the third and fourth ramp surfaces 76 and 78 of the lower endplate member 38. As a result, the first and second ramp surfaces 132 and 134 of the first wedge member 44 can maintain surface contact with the respective third and fourth ramp surfaces 76 and 78 of the lower endplate member 38 as the fusion cage 20 iterates between the contracted position and the expanded position. In one example, the first and second ramp surfaces 132 and 134 of the first wedge member 44 can maintain surface contact with the respective third and fourth ramp surfaces 76 and 78 of the lower endplate member 38 throughout the entire range of motion between the contracted position and the expanded position.

Similarly, the third and fourth ramp surfaces 136 and 138 of the second wedge member 46 can extend along respective upper helical wedge paths of the second wedge member 46. The helical wedge paths of the third and fourth ramp surfaces 136 and 138 of the second wedge member 46 can be defined by a common helical pitch, but defined by different helical radii. For instance, the helical wedge paths of the third and fourth ramp surfaces 136 and 138 can be defined by a single swept helix. The upper helical wedge paths can be complementary to the respective helical paths of the third and fourth ramp surfaces 90 and 92 of the upper endplate member 36. Thus, the respective helical wedge paths of the third and fourth ramp surfaces 136 and 138 of the second wedge member 46 can define a convex helical path. As a result, the third and fourth ramp surfaces 136 and 138 of the second wedge member 46 can maintain surface contact with the respective third and fourth ramp surfaces 90 and 92 of the upper endplate member 36 as the fusion cage 20 iterates between the contracted position and the expanded position. In one example, the third and fourth ramp surfaces 136 and 138 of the second wedge member 46 can maintain surface contact with the respective third and fourth ramp surfaces 90 and 92 of the upper endplate member 36 throughout the entire range of motion between the contracted position and the expanded position.

Referring also to FIGS. 8A and 9A, the first ramp surface 132 of the second wedge member 46 can define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle $\alpha_1$ of the first ramp surface 132 can define the first ramp angle $\theta_1$ in a range from approximately 20 degrees to approximately 40 degrees, such as approximately 30 degrees, with respect to the longitudinal direction L (or a plane that includes the longitudinal direction L and the lateral direction A). The first ramp angle $\theta_1$ of the first ramp surface 132 can be geometrically complementary to the first helical lead-in angle $\alpha_1$ of the first ramp surface 132. The third ramp surface 136 of the second wedge member 46 can also define the first helical lead-in angle $\alpha_1$ that can be in the range from approximately 50 degrees to approximately 70 degrees, such as approximately 60 degrees with respect to the transverse direction T (or a respective plane that includes the transverse direction T and the lateral direction A). Thus, the first helical lead-in angle $\alpha_1$ of the third ramp surface 136 can define the first ramp angle $\theta_1$ in the range from approximately 20 degrees to approximately 40 degrees, such as approximately 30 degrees, with respect to the longitudinal direction L (or the plane that includes the longitudinal direction L and the lateral direction A). The first ramp angle $\theta_1$ of the third ramp surface 136 can be geometrically complementary to the first helical lead-in angle $\alpha_1$ of the third ramp surface 136. The first ramp angle $\theta_1$ of the third ramp surface 136 can be oriented opposite the first ramp angle $\theta_1$ of the first ramp surface 132. Further, the first ramp angle $\theta_1$ of the first ramp surface 132 can be oriented parallel with the first ramp angle of the third ramp surface 116 of the first wedge member 44 (see FIG. 9A). Further still, the first ramp angle $\theta_1$ of the first ramp surface 132 can be oriented opposite the first ramp angle $\theta_1$ of the first ramp surface 112 of the first wedge member 44 (see FIG. 9A).

The second ramp surface 134 of the second wedge member 46 can define the second helical lead-in angle $\alpha_2$ that can be in a range from approximately 26 degrees to approximately 48 degrees, such as approximately 35 degrees with respect to the transverse direction T (or a respective plane that includes the transverse direction T and the lateral direction A). Thus, the second helical lead-in angle $\alpha_2$ of the second ramp surface 134 can define a second ramp angle $\theta_2$ in a range from approximately 42 degrees to approximately 64 degrees, such as approximately 55 degrees, with respect to the longitudinal direction L (or a plane that includes the longitudinal direction L and the lateral direction A). The second ramp angle $\theta_2$ of the second ramp surface 134 can be geometrically complementary to the second helical lead-in angle $\alpha_2$ of the second ramp surface 134. The fourth ramp surface 138 of the second wedge member 46 can also define the second helical lead-in angle $\alpha_2$ that can be in the range from approximately 26 degrees to approximately 48 degrees, such as approximately 35 degrees with respect to the transverse direction T (or a respective plane that includes the transverse direction T and the lateral direction A). Thus, the second helical lead-in angle $\alpha_2$ of the fourth ramp surface 138 can define the second ramp angle $\theta_2$ in the range from approximately 42 degrees to approximately 64 degrees, such as approximately 55 degrees, with respect to the longitudinal direction L (or the plane that includes the longitudinal direction L and the lateral direction A). The second ramp angle $\theta_2$ of the fourth ramp surface 138 can be geometrically complementary to the second helical lead-in angle $\alpha_2$ of the fourth ramp surface 138. The second ramp angle $\theta_2$ of the fourth ramp surface 138 can be oriented opposite the second ramp angle $\theta_2$ of the second ramp surface 134. Further, the fourth ramp surface 138 can be oriented parallel with the fourth ramp surface 92 of the upper endplate member 36 (see FIG. 8A). Further still, the second ramp angle $\theta_2$ of the fourth ramp surface 138 can be oriented opposite the second ramp angle $\theta_2$ of the fourth ramp surface 118 of the first wedge member 44 (see FIG. 8A).

As described above, the second wedge member 46 can be interlinked with each of the upper and lower endplate members 36 and 38. That is, the second wedge member 46 can include at least one protrusion that is captured by the upper endplate member 36, and at least one protrusion that is captured by the lower endplate member 38. In particular, the second wedge member 46 can include a first protrusion 140 that extends out from the second wedge body 130 along the lateral direction A. The first protrusion 140 can be spaced below the first ramp surface 132, and aligned with at least a portion of the first ramp surface 132 along the transverse direction T, such that the second wedge member 46 defines a first gap that extends between the first protrusion 140 and the first ramp surface 132. The second wedge member 46 can further include a second protrusion 142 that extends out from the second wedge body 130 along the lateral direction A. The second protrusion 142 can extend out from the second wedge body 130 a direction opposite the first protrusion 140. The second protrusion 142 can be spaced below the second ramp surface 134, and aligned with at least a portion of the second ramp surface 134 along the transverse direction T, such that the second wedge member 46 defines a second gap that extends between the second protrusion 142 and the second ramp surface 134. The first and second protrusions 140 and 142 can be referred to as lower protrusions of second wedge member 46, or a lower pair of protrusions of the second wedge member 46. While the first and second protrusions 140 and 142 are illustrated as protrusions separate from each other along the lateral direction A, it should be appreciated that the first and second protrusions 140 and 142 can alternatively be continuous with each other to define a single unitary protrusion.

Similarly, the second wedge member 46 can include a third protrusion 144 that extends out from the second wedge body 130 along the lateral direction A. The third protrusion 144 can be spaced above the third ramp surface 136, and aligned with at least a portion of the third ramp surface 136 along the transverse direction T, such that the second wedge member 46 defines a third gap that extends between the third protrusion 144 and the third ramp surface 136. The second wedge member 46 can include a fourth protrusion 146 that extends out from the second wedge body 130 along the lateral direction A. The fourth protrusion 146 can be spaced above the fourth ramp surface 138, and aligned with at least a portion of the fourth ramp surface 138 along the transverse direction T, such that the second wedge member 46 defines a fourth gap that extends between the fourth protrusion 146 and the fourth ramp surface 138. The third and fourth protrusions 144 and 146 can be referred to as upper protrusions of the second wedge member 46, or an upper pair of protrusions of the second wedge member 46. While the third and fourth protrusions 144 and 146 are illustrated as protrusions separate from each other along the lateral direction A, it should be appreciated that the third and fourth protrusions 144 and 146 can alternatively be continuous with each other to define a single unitary protrusion.

The second wedge member 46 can interlink with the upper and lower endplates 36 and 38, respectively. In particular, the first and second protrusions 140 and 142 can be disposed in respective ones of the second slots 73 of the lower endplate member 38 (see FIGS. 3A-3B). Similarly, the third and fourth protrusions 144 and 146 can be disposed in respective ones of the second slots 87 of the upper endplate member 36 (see FIGS. 4A-4B). Accordingly, the second wedge member 46 can be captured by each of the upper and lower endplate members 36 and 38. Further, as the second wedge member 46 is moved in the contraction direction, the first and second protrusions 140 and 142 can ride along respective ramped inner surfaces of the lower endplate member 38 opposite the third and fourth ramp surfaces 76 and 78 (see FIGS. 3A-3B), which can urge the lower endplate member 38 toward the upper endplate member 36 along the transverse direction T. Similarly, as the second wedge member 46 is moved in the contraction direction, the third and fourth protrusions 144 and 146 can ride along respective ramped inner surfaces of the upper endplate member 36 opposite the third and fourth ramp surfaces 90 and 92 (see FIGS. 4A-4B), which can urge the upper endplate member 36 toward the lower endplate member 38 along the transverse direction T. Thus, both the height and lordotic curvature of the cage 20 can be reduced. Alternatively or additionally, movement of the second wedge member 46 in the contraction direction allows anatomical or other forces to cause the upper and lower endplate members 36 and 38 to move toward each other.

Operation of the fusion cage 20 will now be described with initial reference to FIGS. 7A-9B. In particular, when the fusion cage 20 is in the contracted position, the upper and lower bone contacting surfaces 28 and 30 can be substantially parallel to each other. In particular, the upper and lower bone contacting surfaces 28 and 30 can each substantially extend along respective planes that are oriented along the longitudinal direction L and the lateral direction A. In other examples, the upper and lower bone contacting surfaces 28 and 30 can be angled with respect to each other when the fusion cage 20 is in the contracted position. For instance, the upper and lower bone contacting surfaces 28 and 30 can be lordotically angled with respect to each other when the fusion cage 20 is in the contracted position The angle defined by the upper and lower bone contacting surfaces 28 and 30 can become increasingly lordotic during expansion of the implant to the expanded position as described herein. Further, when the fusion cage 20 is in the contracted position, first and second sides 23 and 25 of the fusion cage 20 define a first or contracted height H1 along the transverse direction T that extends from the upper bone contacting surface 28 to the lower bone contacting surface 30. Further, in one example the upper and lower endplate members 36 and 38 abut each other such that the implant 20 is unable to achieve a height less than the first height H1 due to movement of the wedge members 44 and 46 in the contraction direction. In particular, the inner surface 67 of the lower plate portion 64 of the lower endplate member 38 and the inner surface 83 of the upper plate portion 80 of the upper plate member 36 can abut each other. Accordingly, fusion cage 20 can be configured such that the actuator shaft 48 is unable to be rotated in the second direction of rotation when the cage is in the contracted position.

When it is desirable to expand the fusion cage 20, the actuator 48 is rotated in the first direction of rotation relative to the cage body 21. The first direction of rotation can be clockwise. Alternatively, the first direction of rotation can be counterclockwise. Rotation of the actuator 48 in the first direction of rotation, causes the first and second wedge members 44 and 46 to travel in the expansion direction. In one example, the first and second wedge members 44 and 46 can travel along the actuator shaft 50 toward each other in the expansion direction.

As described above, the first and third ramp surfaces 112 and 116 of the first wedge member 44 abut the first ramp surface 72 of the lower endplate member 38 and the first ramp surface 86 of the upper endplate member 36, respectively. The first and third ramp surfaces 112 and 116 can be referred to as a first pair 148a of wedge ramp surfaces at the first side 23 of the cage body 21. The first ramp surface 72 of the lower endplate member 38 and the first ramp surface 86 of the upper endplate member 36 can be referred to as a first pair 148b of endplate ramp surfaces at the first side 23 of the cage body 21. During movement of the first wedge member 44 in the expansion direction, the first ramp surface 112 rides along the first ramp surface 72 of the lower endplate member, and urges the first ramp surface 72 away from the upper endplate member 36. Further, the third ramp surface 116 rides along the first ramp surface 86 of the upper endplate member 36, and urges the first ramp surface 86 away from the lower endplate member 38.

The second and fourth ramp surfaces 114 and 118 of the first wedge member 44 abut the second ramp surface 74 of the lower endplate member 38 and the second ramp surface 88 of the upper endplate member 36, respectively. The second and fourth ramp surfaces 114 and 118 can be referred to as a second pair 150a of wedge ramp surfaces at the second side 25 of the cage body 21. The second ramp surface 74 of the lower endplate member 38 and the second ramp surface 88 of the upper endplate member 36 can be referred to as a second pair 150b of endplate ramp surfaces. During movement of the first wedge member 44 in the expansion direction, the second ramp surface 114 rides along the second ramp surface 74 of the lower endplate member 38, and urges the second ramp surface 74 away from the upper endplate member 36. Further, the fourth ramp surface 118 rides along the second ramp surface 88 of the upper endplate member 36, and urges the second ramp surface 88 away from the lower endplate member 38.

The first and third ramp surfaces 132 and 136 of the second wedge member 46 abut the third ramp surface 76 of the lower endplate member 38 and the third ramp surface 90 of the upper endplate member 36, respectively. The first and third ramp surfaces 132 and 136 can be referred to as a third pair 152a of wedge ramp surfaces at the first side 23 of the cage body 21. The third ramp surface 76 of the lower endplate member 38 and the third ramp surface 90 of the upper endplate member 36 can be referred to as a third pair 152b of endplate ramp surfaces at the first side 23 of the cage body 21. During movement of the second wedge member 46 in the expansion direction, the first ramp surface 132 rides along the third ramp surface 76 of the lower endplate member 38, and urges the third ramp surface 76 away from the upper endplate member 36. Further, the third ramp surface 136 rides along the third ramp surface 90 of the upper endplate member 36, and urges the third ramp surface 90 away from the lower endplate member 38.

The second and fourth ramp surfaces 134 and 138 of the second wedge member 46 abut the fourth ramp surface 78 of the lower endplate member 38 and the fourth ramp surface 92 of the upper endplate member 36, respectively. The second and fourth ramp surfaces 134 and 138 can be referred to as a fourth pair 154a of wedge ramp surfaces at the second side 25 of the cage body 21. The fourth ramp surface 78 of the lower endplate member 38 and the fourth ramp surface 92 of the upper endplate member 36 can be referred to as a fourth pair 154b of endplate ramp surfaces at the second side 23 of the cage body 21. During movement of the second wedge member 46 in the expansion direction, the second ramp surface 134 rides along the fourth ramp surface 78 of the lower endplate member 38, and urges the fourth ramp surface 78 away from the upper endplate member 36. Further, the fourth ramp surface 138 rides along the fourth ramp surface 92 of the upper endplate member 36, and urges the fourth ramp surface 92 away from the lower endplate member 38.

As described above, the first and third pairs 148a-b and 152 a-b of wedge ramp surfaces and endplate ramp surfaces at the first side 23 of the cage body 21 can define respective first ramp angles with respect to the longitudinal direction L. The second and fourth pairs 150a-b and 154a-b of wedge ramp surfaces and endplate ramp surfaces at the second side 25 of the cage body 21 define respective second ramp angles with respect to the longitudinal direction. The second ramp angles can be greater than the first ramp angles. As the first and second wedge members 44 and 46 move in the expansion direction, respective entireties of the first and second endplate members 36 and 38 move away from each other along the transverse direction.

It is recognized of course, that in certain surgical applications, the lower endplate member 38 can be supported, for instance by the inferior vertebral surface 42 of the inferior vertebral body 26 (see FIG. 1). Accordingly, when the endplate is expanded from the contracted position to the expanded position, the lower endplate member 38 can remain supported by the inferior vertebral surface, such that upper endplate member 36 moves away from the lower endplate member 38 while the lower endplate member 38 remains substantially stationary with respect to expansion along the transverse direction T. However, as this is due to the particular surgical application, it can nevertheless be said that the upper and lower endplate members 36 and 38 are movable away from each other along the transverse direction T, and angulate with respect to each other as described above. In other embodiments, the wedge members 44 and 46 can include only their upper ramp surfaces and not include lower ramp surfaces, such that the wedge members 44 and 46 urge the upper endplate member 36 away from the lower endplate member 38 without urging the lower endplate member 38 away from the upper endplate member 36 as the fusion cage 20 moves to the lordotic expanded position.

Further, the first and second endplate members 36 and 38 move away from each other along the transverse direction at a greater rate at second side 25 of the cage body 21 than at the first side 23 of the cage body 21. As a result, when the fusion cage 20 is in the expanded position, the fusion cage 20 can be wedge-shaped along a direction from the second side 25 of the cage body 21 toward the first side 23 of the cage body 21 along the lateral direction A. In particular, the fusion cage 20 has a second height H2 at the first side 23 of the cage body 21 that extends from the upper bone contacting surface 28 to the lower bone contacting surface 30 along the transverse direction T. The fusion cage 20 has a third height H3 at the second side 25 of the cage body 21 that extends from the upper bone contacting surface 28 to the lower bone contacting surface 30 along the transverse direction T. The second height H2 that is defined when the fusion cage 20 is in the expanded position is greater than the first height H1 that is defined when the fusion cage 20 is in the contracted position. The third height H3 that is defined when the fusion cage is in the expanded position is greater than the second height H2. Thus, the upper and lower bone contacting surfaces 28 and 30 define an angle with respect to each other in a plane that is defined by the lateral direction A and the transverse direction T. The angle can be defined in the first lateral direction from the second side 25 of the fusion cage 20 toward the first side 23. The angle can be in a range from approximately 3 degrees to approximately 20 degrees, for instance from approximately 5 degrees to approximately 10 degrees. It is appreciated that the angle can increase as the cage expands from the contracted position to the expanded position.

Advantageously, the first and second wedge members 44 and 46, respectively, can be configured to maintain surface contact with each of the ramp surfaces 72-78 of the lower endplate member 38 when the fusion cage 20 is in the compressed position, as the fusion cage 20 iterates between the contracted position and the expanded position, and when the fusion cage 20 is in the expanded position. That is, at least respective majorities up to respective entireties of the first and third ramp surfaces 112 and 116 of the first wedge member 44 can be in contact with the first ramp surface 72 of the lower endplate member 38 and the first ramp surface 86 of the upper endplate member 36, respectively, when the fusion cage 20 is in the compressed position, as the fusion cage 20 iterates between the contracted position and the expanded position, and when the fusion cage 20 is in the expanded position. Alternatively or additionally, at least respective majorities up to respective entireties of the first ramp surface 72 of the lower endplate member 38 and the first ramp surface 86 of the upper endplate member 36 can be in contact with the first and third ramp surfaces 112 and 116 of the first wedge member 44, respectively, when the fusion cage 20 is in the compressed position, as the fusion cage 20 iterates between the contracted position and the expanded position, and when the fusion cage 20 is in the expanded position.

Further, at least respective majorities up to respective entireties of the second and fourth ramp surfaces 114 and 118 of the first wedge member 44 can be in contact with the second ramp surface 74 of the lower endplate member 38 and the second ramp surface 88 of the upper endplate member 36, respectively, when the fusion cage 20 is in the compressed position, as the fusion cage 20 iterates between the contracted position and the expanded position, and when the fusion cage 20 is in the expanded position. Alternatively or additionally, at least respective majorities up to respective entireties of the second ramp surface 74 of the lower endplate member 38 and the second ramp surface 88 of the upper endplate member 36 can be in contact with the second and fourth ramp surfaces 114 and 118 of the first wedge member 44, respectively, when the fusion cage 20 is in the compressed position, as the fusion cage 20 iterates between the contracted position and the expanded position, and when the fusion cage 20 is in the expanded position.

Similarly, at least respective majorities up to respective entireties of the first and third ramp surfaces 132 and 136 of the second wedge member 46 can be in contact with the third ramp surface 76 of the lower endplate member 38 and the third ramp surface 90 of the upper endplate member 36, respectively, when the fusion cage 20 is in the compressed position, as the fusion cage 20 iterates between the contracted position and the expanded position, and when the fusion cage 20 is in the expanded position. Alternatively or additionally, at least respective majorities up to respective entireties of the third ramp surface 76 of the lower endplate member 38 and the third ramp surface 90 of the upper endplate member 36, respectively, can be in contact with the first and third ramp surfaces 132 and 136 of the second wedge member 46, respectively, when the fusion cage 20 is in the compressed position, as the fusion cage 20 iterates between the contracted position and the expanded position, and when the fusion cage 20 is in the expanded position.

Further, at least respective majorities up to respective entireties of the second and fourth ramp surfaces 134 and 138 of the second wedge member 46 can be in contact with the fourth ramp surface 78 of the lower endplate member 38 and the fourth ramp surface 92 of the upper endplate member 36, respectively, when the fusion cage 20 is in the compressed position, as the fusion cage 20 iterates between the contracted position and the expanded position, and when the fusion cage 20 is in the expanded position. Alternatively or additionally, at least respective majorities up to respective entireties of the fourth ramp surface 78 of the lower endplate member 38 and the fourth ramp surface 92 of the upper endplate member 36 can be in contact with the second and fourth ramp surfaces 134 and 138 of the second wedge member 46, respectively, when the fusion cage 20 is in the compressed position, as the fusion cage 20 iterates between the contracted position and the expanded position, and when the fusion cage 20 is in the expanded position.

The surface contact during lordotic expansion, each of the first, second, third, and fourth pairs 148a-b, 150a-b, 152 a-b, and 154 a-b of wedge ramp surfaces and endplate ramp surfaces can define non-planar surfaces that maintain surface contact during lordotic expansion of the fusion cage 20. In some examples, the non-planar surfaces can define curvatures. For instance, the non-planar surfaces can be twisted. For instance, the non-planar surfaces can define helical curvatures. The curvatures of ramp surfaces that abut each other can be complementary to each other. Accordingly, the ramp surfaces that abut each other can nest with each other as they ride along each other. Thus, the ramp surfaces that abut each other can maintain surface contact with each other during at least a portion of the movement of the fusion cage 20 from the contracted position to the expanded position, and from the expanded position to the contracted position. Further, the ramp surfaces that abut each other can maintain surface contact with each other during an entirety of the movement of the fusion cage 20 from the contracted position to the expanded position, and from the expanded position to the contracted position.

Further, the first wedge member 44 and the second wedge member 46 can be substantially symmetrical with respect to each other, meaning that the first and second wedge members 44 and 46 can be symmetrical with respect to each other with the exception of the anti-rotation apertures 121 of the first wedge member 44 in some instances. Thus, it can be said that the first wedge body 110 and the ramp surfaces of the first wedge member 44 can have a size and shape that is substantially symmetrical with respect to the size and shape of the second wedge body 130 and the ramp surfaces of the second wedge member 46. Accordingly, the first ramp surface 112 of the first wedge member 44 can be substantially symmetrical with respect to the first ramp surface 132 of the second wedge member 46. Further, the second ramp surface 114 of the first wedge member 44 can be substantially symmetrical with respect to the second ramp surface 134 of the second wedge member 46. Further, the third ramp surface 116 of the first wedge member 44 can be substantially symmetrical with respect to the third ramp surface 136 of the second wedge member 46. Further still, the fourth ramp surface 118 of the first wedge member 44 can be substantially symmetrical with respect to the fourth ramp surface 138 of the second wedge member 46.

Figure 11A:
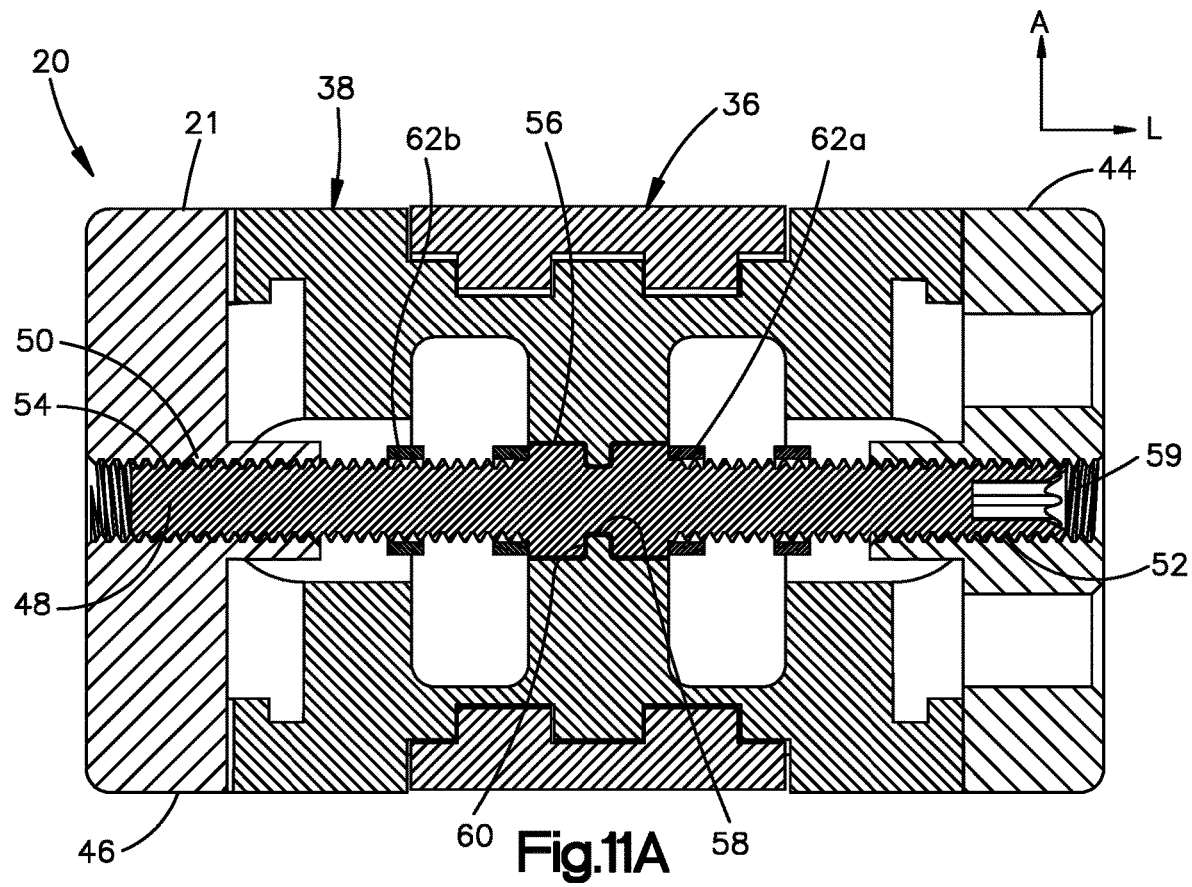
FIG. 11A is a sectional side elevation view of the fusion cage of FIG. 10A shown in the contracted position.
Figure 11B:
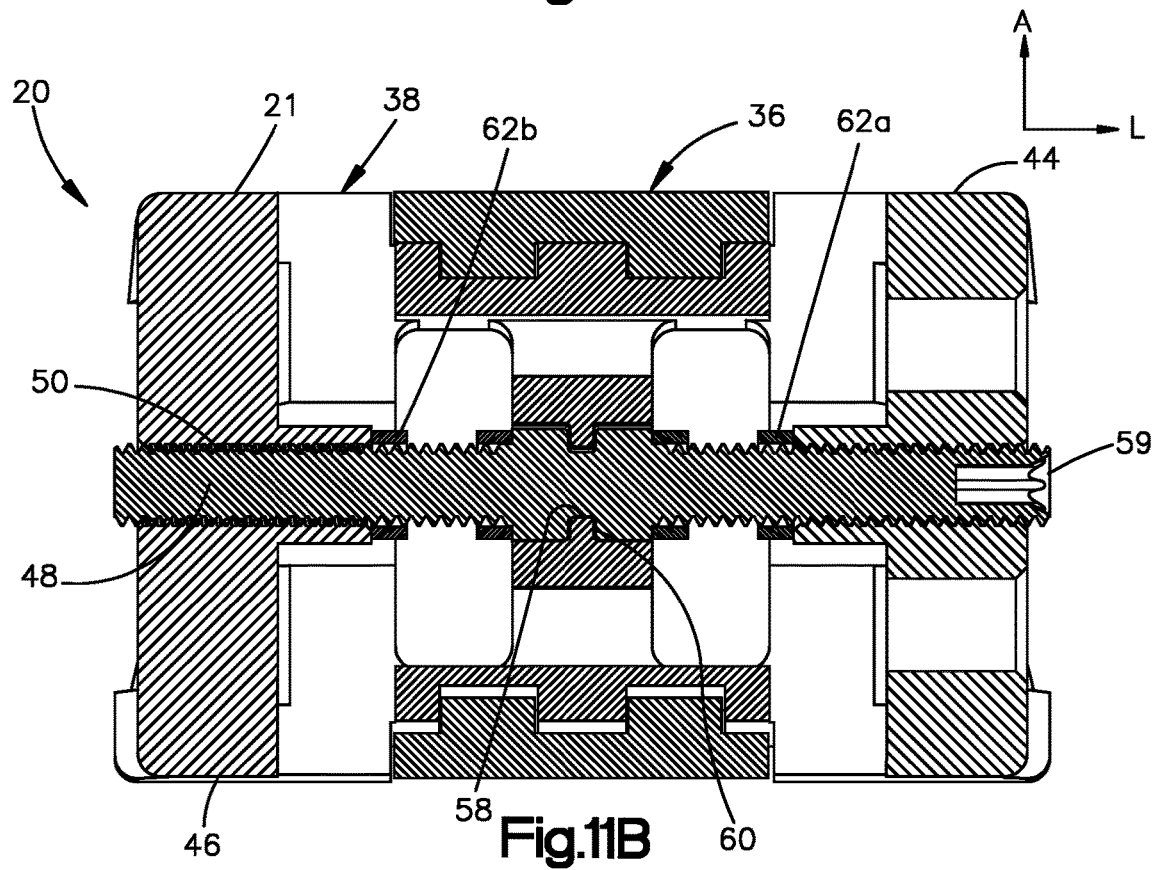
FIG. 11B is a sectional side elevation view of the fusion cage of FIG. 11A shown in the expanded position with the stop members engaged to prevent further expansion of the fusion cage.

Referring now also to FIGS. 11A-11B, and as described above, the fusion cage 20 can include first and second stop members 62a-b that can be configured to limit expansion of the fusion cage. In particular, the stop members 62a-b can be mounted onto the actuator shaft 50, and thus the actuator 48, at a location between respective first and second stop structures that move toward each other in response to movement of the fusion cage 20 from the contracted position to the expanded position. Referring to the first stop member 62a, the first stop structure can be defined by the first wedge member 44, and the second stop structure can be defined by the locating flange 56 of the actuator 48 or any suitable alternative structure of or supported by the actuator 48. Referring to the second stop member 62b, the first stop structure can be defined by the second wedge member 46, and the second structure can be defined by the locating flange 56 of the actuator 48 or any suitable alternative stop structure of or supported by the actuator 48. The stop members 62a-b can be unthreaded and thus freely slidable along the actuator shaft 50. Alternatively, the stop members 62a-b can be translatably fixed to the locating flange 56 or alternative first structure.

During operation, as the wedge members 44 and 46 move toward each other in the expansion direction, the wedge members 44 and 46 also move toward the locating flange 56. Thus, the first and second wedge members 44 and 46 can move in the expansion direction from the initial position to a stop position whereby the stop members 62a-63b are in abutment with both the respective first and second stop structures, which thereby prevents further movement of the wedge members 44 and 46 in the expansion direction, and correspondingly preventing further rotation of the actuator 48 in the first direction of rotation. Because the wedge members 44 and 46 can be positioned at symmetric locations of the actuator shaft 50, it is appreciated that both wedge members 44 and 46 can abut the respective stop members 62a and 62b simultaneously when the stop members 62a and 62b are in abutment with the respective first stop structure. In other examples, movement of either of the wedge members 44 and 46 in the expansion direction can be prevented due to abutment with the corresponding stop member 62, thereby preventing further rotation of the actuator 48.

It is appreciated that the fusion cage can define the expanded position when the wedge members 44 and 46 are disposed at any position spaced from the initial position in the expansion direction. The fusion cage 20 is configured to maintain the expanded position in response to compressive anatomical forces applied by the inferior vertebral body 26 and the superior vertebral body 24. In one example, frictional forces between the actuator 48 and the wedge members 44 and 46 can prevent the anatomical forces from causing the wedge members 44 and 46 to move in the contraction direction. In this regard, it is recognized that the ramp surfaces of the wedge members 44 and 46 are in abutment with the complementary ramp surfaces of the upper and lower endplates 36 and 38.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable intervertebral fusion cage for insertion in an intervertebral space defined between a superior vertebral body and an inferior vertebral body, the fusion cage comprising:
a cage body including:
an upper endplate member defining an upper bone contacting surface configured to abut the superior vertebral body, the upper endplate member further including at least one proximal upper ramp surface and at least one distal upper ramp surface that each extend along respective helical paths, wherein the at least one proximal ramp surface of the upper endplate member comprises first and second ramp surfaces of the upper endplate member spaced from each other along a lateral direction, and the at least one distal ramp surface of the upper endplate member comprises third and fourth ramp surfaces of the upper endplate member spaced from each other along the lateral direction;
a lower endplate member defining a lower bone contacting surface configured to abut the inferior vertebral body, wherein the upper and lower bone contacting surfaces are opposite each other along a transverse direction;
a proximal wedge member having at least one upper ramp surface that abuts the at least one proximal upper ramp surface of the upper endplate member;
a distal wedge member having at least one upper ramp surface that abuts the at least one distal upper ramp surface of the upper endplate member, wherein the proximal and distal wedge members are opposite each other along a longitudinal direction that is perpendicular to the transverse direction,
wherein the cage body defines a first side and a second side opposite the first side along the lateral direction that is perpendicular to each of the longitudinal direction and the transverse direction; and
an actuator having an actuator shaft that defines a proximal section coupled to the proximal wedge member and a distal section that is coupled to the distal wedge member and aligned with the proximal section along the longitudinal direction, such that movement of the actuator in a first direction causes the proximal and distal wedge members to move in an expansion direction whereby (i) the at least one upper ramp surface of the proximal wedge member rides along the at least one proximal upper ramp surface of the upper endplate member in surface contact with the at least one proximal upper ramp surface of the upper endplate member, and (ii) the at least one upper ramp surface of the distal wedge member rides along the at least one distal upper ramp surface of the upper endplate member in surface contact with the at least one distal upper ramp surface of the upper endplate member, thereby causing an entirety of the upper endplate member to move away from the lower endplate member,
wherein movement of the proximal and distal wedge members in the expansion direction causes the upper endplate member at the second side of the fusion cage to move away from the lower endplate at a greater rate than the upper endplate member at the first side of the fusion cage moves away from the lower endplate member, thereby causing lordotic expansion of the intervertebral fusion cage.

2. The expandable intervertebral fusion cage of claim 1, wherein:
the lower endplate member further includes at least one proximal lower ramp surface and at least one distal lower upper ramp surface,
the proximal wedge member further comprises at least one lower ramp surface,
the distal wedge member further comprises at least one lower ramp surface,
movement of the proximal and distal wedge members in the expansion direction causes (i) the at least one lower ramp surface of the proximal wedge member to ride along the at least one proximal lower ramp surface of the lower endplate member in surface contact with the at least one proximal lower ramp surface of the lower endplate member, and (ii) the at least one lower ramp surface of the distal wedge member to ride along the at least one distal lower ramp surface of the lower endplate member in surface contact with the at least one distal lower ramp surface of the lower endplate member, thereby causing an entirety of the lower endplate member to move away from the upper endplate member, and
wherein movement of the proximal and distal wedge members in the expansion direction causes the lower endplate member at the second side of the fusion cage to move away from the upper endplate at a greater rate than the lower endplate member at the first side of the fusion cage moves away from the upper endplate member.

3. The expandable intervertebral fusion cage of claim 2, wherein all ramp surfaces of the upper and lower endplate members and proximal and distal wedge members extend along respective non-planar paths.

4. The expandable intervertebral fusion cage of claim 3, wherein the respective non-planar paths define respective helical paths.

5. The expandable intervertebral fusion cage of claim 1, wherein the actuator comprises a single actuator shaft having proximal and distal threaded portions that are threadedly coupled to the proximal and distal wedge members, respectively, such that rotation of the actuator in a first direction of rotation causes the proximal and distal wedge members to translate along the actuator shaft in the expansion direction.

6. The expandable intervertebral fusion cage of claim 1, wherein the proximal and distal wedge members are substantially symmetrical with respect to each other.

7. The expandable intervertebral fusion cage of claim 1, wherein the proximal and distal wedge members undergo pure translation along the actuator shaft as they move along the expansion direction.

8. The expandable intervertebral fusion cage of claim 1, wherein the actuator shaft is the only actuator shaft of the intervertebral fusion cage.

9. The expandable intervertebral fusion cage of claim 1, wherein the upper and lower endplate members have respective ribs at each of the first and second sides of the cage that engage each other so as to guide movement of the upper and lower endplates away from each other, wherein the ribs define a curvature as they extend along the transverse direction.

10. The expandable intervertebral fusion cage of claim 1, wherein the actuator further comprises a locating flange that extends from the actuator shaft, and the lower endplate member defines a cradle that receives the locating flange so as to limit movement of the actuator shaft relative to the lower endplate member along the longitudinal direction, and the cradle defines a central cradle axis that extends along a lateral curved path in a direction from the second side of the cage toward the first side of the cage as it extends upward.

11. The expandable intervertebral fusion cage of claim 1, wherein the proximal and distal wedge members comprise respective protrusions that are captured in respective slots of the upper and lower endplate member, so as to interlink the proximal and distal wedge members with the upper and lower endplate members.

12. The expandable intervertebral fusion cage of claim 1, wherein:
the at least one upper ramp surface of the proximal wedge member comprises first and second proximal ramp surfaces opposite each other along the lateral direction, and the at least one lower ramp surface of the proximal wedge member comprises third and fourth proximal ramp surfaces, wherein the first and third proximal ramp surfaces are disposed at the first side of the cage body and define respective first ramp angles that are equal and opposite each with respect to the longitudinal direction, the second and fourth proximal ramp surfaces are disposed at the second side of the cage body and define respective second ramp angles that are equal and opposite each other with respect to the longitudinal direction, the second ramp angles being greater than the first ramp angle.

13. The expandable intervertebral fusion cage of claim 12, wherein:
the at least one upper ramp surface of the distal wedge member comprises first and second distal ramp surfaces opposite each other along the lateral direction, and the at least one lower ramp surface of the distal wedge member comprises third and fourth distal ramp surfaces, wherein the first and third distal ramp surfaces are disposed at the first side of the cage body and are define the respective first ramp angles that are equal and opposite each other with respect to the longitudinal direction, the second and fourth distal ramp surfaces are disposed at the second side of the cage body and define the respective second ramp angles that are equal and opposite each other with respect to the longitudinal direction.

14. The expandable intervertebral fusion cage of claim 13, wherein:
the first ramp surface of the proximal wedge member is sloped equal and opposite the first ramp surface of the distal wedge member,
the second ramp surface of the proximal wedge member is sloped equal and opposite the second ramp surface of the distal wedge member,
the third ramp surface of the proximal wedge member is sloped equal and opposite the third ramp surface of the distal wedge member, and
the fourth ramp surface of the proximal wedge member is sloped equal and opposite the fourth ramp surface of the distal wedge member.

15. The expandable intervertebral fusion cage of claim 13, wherein:
the first, second, third, and fourth ramp surfaces of the proximal wedge member are rotatably fixed with respect to each other, and
the first, second, third, and fourth ramp surfaces of the distal wedge member are rotatably fixed with respect to each other.

16. An expandable intervertebral fusion cage for insertion in an intervertebral space defined between a superior vertebral body and an inferior vertebral body, the fusion cage comprising:
a cage body including:
an upper endplate member defining an upper bone contacting surface configured to abut the superior vertebral body, the upper endplate member further including at least one proximal upper ramp surface and at least one distal upper ramp surface that each extend along respective helical paths;
a lower endplate member defining a lower bone contacting surface configured to abut the inferior vertebral body, wherein the upper and lower bone contacting surfaces are opposite each other along a transverse direction;
a proximal wedge member having at least one upper ramp surface that abuts the at least one proximal upper ramp surface of the upper endplate member;
a distal wedge member having at least one upper ramp surface that abuts the at least one distal upper ramp surface of the upper endplate member, wherein the proximal and distal wedge members are opposite each other along a longitudinal direction that is perpendicular to the transverse direction,
wherein the cage body defines a first side and a second side opposite the first side along a lateral direction that is perpendicular to each of the longitudinal direction and the transverse direction; and
an actuator having an actuator shaft that defines a proximal section coupled to the proximal wedge member and a distal section that is coupled to the distal wedge member and aligned with the proximal section along the longitudinal direction, such that movement of the actuator in a first direction causes the proximal and distal wedge members to move in an expansion direction whereby (i) the at least one upper ramp surface of the proximal wedge member rides along the at least one proximal upper ramp surface of the upper endplate member in surface contact with the at least one proximal upper ramp surface of the upper endplate member, and (ii) the at least one upper ramp surface of the distal wedge member rides along the at least one distal upper ramp surface of the upper endplate member in surface contact with the at least one distal upper ramp surface of the upper endplate member, thereby causing an entirety of the upper endplate member to move away from the lower endplate member,
wherein the actuator shaft is the only actuator shaft of the intervertebral fusion cage, and
wherein movement of the proximal and distal wedge members in the expansion direction causes the upper endplate member at the second side of the fusion cage to move away from the lower endplate at a greater rate than the upper endplate member at the first side of the fusion cage moves away from the lower endplate member, thereby causing lordotic expansion of the intervertebral fusion cage.

17. The expandable intervertebral fusion cage of claim 16, wherein the upper and lower endplate members have respective ribs at each of the first and second sides of the cage that engage each other so as to guide movement of the upper and lower endplates away from each other, wherein the ribs define a curvature as they extend along the transverse direction.

18. The expandable intervertebral fusion cage of claim 16, wherein:
the at least one upper ramp surface of the proximal wedge member comprises first and second proximal ramp surfaces opposite each other along the lateral direction, and the at least one lower ramp surface of the proximal wedge member comprises third and fourth proximal ramp surfaces, wherein the first and third proximal ramp surfaces are disposed at the first side of the cage body and define respective first ramp angles that are equal and opposite each with respect to the longitudinal direction, the second and fourth proximal ramp surfaces are disposed at the second side of the cage body and define respective second ramp angles that are equal and opposite each other with respect to the longitudinal direction, the second ramp angles being greater than the first ramp angle.

19. An expandable intervertebral fusion cage for insertion in an intervertebral space defined between a superior vertebral body and an inferior vertebral body, the fusion cage comprising:

a cage body including:
an upper endplate member defining an upper bone contacting surface configured to abut the superior vertebral body, the upper endplate member further including at least one proximal upper ramp surface and at least one distal upper ramp surface that each extend along respective helical paths;
a lower endplate member defining a lower bone contacting surface configured to abut the inferior vertebral body, wherein the upper and lower bone contacting surfaces are opposite each other along a transverse direction;
a proximal wedge member having at least one upper ramp surface that abuts the at least one proximal upper ramp surface of the upper endplate member;
a distal wedge member having at least one upper ramp surface that abuts the at least one distal upper ramp surface of the upper endplate member, wherein the proximal and distal wedge members are opposite each other along a longitudinal direction that is perpendicular to the transverse direction,
wherein the cage body defines a first side and a second side opposite the first side along a lateral direction that is perpendicular to each of the longitudinal direction and the transverse direction; and
an actuator having an actuator shaft that defines a proximal section coupled to the proximal wedge member and a distal section that is coupled to the distal wedge member and aligned with the proximal section along the longitudinal direction, such that movement of the actuator in a first direction causes the proximal and distal wedge members to move in an expansion direction whereby (i) the at least one upper ramp surface of the proximal wedge member rides along the at least one proximal upper ramp surface of the upper endplate member in surface contact with the at least one proximal upper ramp surface of the upper endplate member, and (ii) the at least one upper ramp surface of the distal wedge member rides along the at least one distal upper ramp surface of the upper endplate member in surface contact with the at least one distal upper ramp surface of the upper endplate member, thereby causing an entirety of the upper endplate member to move away from the lower endplate member, wherein movement of the proximal and distal wedge members in the expansion direction causes the upper endplate member at the second side of the fusion cage to move away from the lower endplate at a greater rate than the upper endplate member at the first side of the fusion cage moves away from the lower endplate member, thereby causing lordotic expansion of the intervertebral fusion cage, and wherein the upper and lower endplate members have respective ribs at each of the first and second sides of the cage that engage each other so as to guide movement of the upper and lower endplates away from each other, wherein the ribs define a curvature as they extend along the transverse direction.

20. The expandable intervertebral fusion cage of claim 19, wherein:

the at least one upper ramp surface of the proximal wedge member comprises first and second proximal ramp surfaces opposite each other along the lateral direction, and the at least one lower ramp surface of the proximal wedge member comprises third and fourth proximal ramp surfaces, wherein the first and third proximal ramp surfaces are disposed at the first side of the cage body and define respective first ramp angles that are equal and opposite each with respect to the longitudinal direction, the second and fourth proximal ramp surfaces are disposed at the second side of the cage body and define respective second ramp angles that are equal and opposite each other with respect to the longitudinal direction, the second ramp angles being greater than the first ramp angle.

* * * * *